(12) United States Patent
Russell et al.

(10) Patent No.: US 7,479,541 B2
(45) Date of Patent: Jan. 20, 2009

(54) HUMAN AND MURINE MUS81 PROTEINS

(75) Inventors: Paul R. Russell, San Diego, CA (US); Jorge E. Vialard, Beerse (BE); Michael N. Boddy, San Diego, CA (US); Paul A. Shanahan, San Diego, CA (US); Antonia Lopez-Girona, San Diego, CA (US); Cecile-Marie D. D. Denis, Beerse (BE); Clare H. McGowan, Del Mar, CA (US)

(73) Assignees: The Scripps Research Institute, La Jolla, CA (US); Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/800,929

(22) Filed: May 8, 2007

(65) Prior Publication Data

US 2007/0213256 A1    Sep. 13, 2007

Related U.S. Application Data

(62) Division of application No. 10/229,355, filed on Aug. 27, 2002, now Pat. No. 7,214,790, which is a division of application No. 09/661,711, filed on Sep. 14, 2000, now Pat. No. 6,440,732.

(60) Provisional application No. 60/153,836, filed on Sep. 14, 1999.

(51) Int. Cl.
    *C07K 14/00*    (2006.01)
(52) U.S. Cl. ...................................... 530/350
(58) Field of Classification Search .................. None
    See application file for complete search history.

(56) References Cited

U.S. PATENT DOCUMENTS 7,396,669 B2 *    7/2008    Boddy et al. ................ 435/196

* cited by examiner

*Primary Examiner*—Karen Cochrane Carlson
(74) *Attorney, Agent, or Firm*—Olson & Cepuritis, Ltd.

(57) ABSTRACT

The present invention encompasses novel mammalian cell cycle checkpoint genes/DNA repair genes, cDNA or genomic DNA, isolated nucleic acids corresponding thereto, proteins encoded thereby, expression vectors comprising said nucleic acids, host cells transformed with said expression vectors, and methods for treating a cell using such nucleic acids or proteins.

6 Claims, 15 Drawing Sheets

```
   1 gatatctgca gaattcgccc ttatggcggc cccggtccgc ctgggccgga agcgcccgct
  61 gcctgcctgt cccaacccgc tcttcgttcg ctggctgacc gagtggcggg acgaggcgac
 121 ccgcagcagg caccgcacgc gcttcgtatt tcagaaggcg ctgcgttccc tccgacggta
 181 cccactgccg ctgcgcagcg ggaaggaagc taagatccta cagcacttcg gagacgggct
 241 ctgccggatg ctggacgagc ggctgcagcg gcaccgaaca tcgggcggtg accatgcccc
 301 ggactcacca tctggagaga acagtccagc cccgcagggg cgacttgcgg aagtccagga
 361 ctcttccatg ccagttcctg cccagcccaa agcgggaggc tctggcagct actggccagc
 421 tcggcactca ggagcccgag tgatactgct ggtgctctac cgggagcacc tgaatcctaa
 481 tggtcaccac ttcttaacca aggaggagct gctgcagagg tgtgctcaga gtcccccag
 541 ggtagcccct gggagtgccc caccctggcc agccctccgc tccctccttc acaggaacct
 601 ggtcctcagg acacaccagc cagccaggta ctcattgacc ccagagggcc tggagctggc
 661 ccagaagttg gccgagtcag aaggcctgag cttgctgaat gtgggcatcg ggcccaagga
 721 gccccctggg gaggagacag cagtgccagg agcagcttca gcagagcttg ccagtgaagc
 781 agggggtccag cagcagccac tggagctgag gcctggagag tacagggtgc tgttgtgtgt
 841 ggacattggc gagacccggg gggcgggca caggccggag ctgctccgag agctacagcg
 901 gctgcacgtg acccacacgg tgcgcaagct gcacgttgga gattttgtgt gggtggctca
 961 ggagaccaat cctagagacc cagcaaaccc tggggagttg gtactggatc acattgtgga
1021 gcgcaagcga ctggatgacc tttgcagcag catcatcgac ggccgcttcc gggagcagaa
1081 gttccgactg aagcgctgtg gtctggagcg ccgggtatac ctggtggaag agcatggttc
1141 cgtccacaac ctcagccttc ctgagagcac actgctgcag gctgtcacca acactcaggt
1201 cattgatggc ttttttgtga agcgcacagc agacattaag gagtcagccg cctacctggc
1261 cctcttgact cggggcctgc agagactcta ccagggccac acctacgca gccgccctg
1321 gggaaccct gggaaccctg aatcaggggc catgacctct ccaaaccctc tctgctcact
1381 cctcaccttc agtgacttca acgcaggagc catcaagaat aaggcccagt cggtgcgaga
1441 agtgtttgcc cggcagctga tgcaggtgcg cggagtgagt ggggagaagg cagcagccct
1501 ggtggatcga tacagcaccc ctgccagcct cctggccgcc tatgatgcct gtgccacccc
1561 caaggaacaa gagacactgc tgagcaccat taagtgtggg cgtctacaga ggaatctggg
1621 gcctgctctg agcaggacct tatcccagct ctactgcagc tacggcccct tgacctgagt
1681 caagggcgaa ttc (SEQ ID NO: 1)
```

```
  1 MAAPVRLGRK RPLPACPNPL FVRWLTEWRD EATRSRHRTR FVFQKALRSL RRYPLPLRSG
 61 KEAKILQHFG DGLCRMLDER LQRHRTSGGD HAPDSPSGEN SPAPQGRLAE VQDSSMPVPA
121 QPKAGGSGSY WPARHSGARV ILLVLYREHL NPNGHHFLTK EELLQRCAQK SPRVAPGSAP
181 PWPALRSLLH RNLVLRTHQP ARYSLTPEGL ELAQKLAESE GLSLLNVGIG PKEPPGEETA
241 VPGAASAELA SEAGVQQQPL ELRPGEYRVL LCVDIGETRG GGHRPELIRE LQRLHVTHTV
301 RKLHVGDFVW VAQETNPRDP ANPGELVLDH IVERKRLDDL CSSIIDGRFR EQKFRLKRCG
361 LERRVYLVEE HGSVHNLSLP ESTLLQAVTN TQVIDGFFVK RTADIKESAA YLALLTRGLQ
421 RLYQGHTLRS RPWGTPGNPE SGAMTSPNPL CSLLTFSDFN AGAIKNKAQS VREVFARQLM
481 QVRGVSGEKA AALVDRYSTP ASLLAAYDAC ATPKEQETLL STIKCGRLQR NLGPALSRTL
541 SQLYCSYGPL T (SEQ ID NO: 2)
```

FIG. 1A

```
   1 gcggccgcag gctctcttct cgttagtgcc ccctgtgttt ggggccccgt gatctcaacg
  61 gtcctgccct cggtctccct cttccccgc ccgccctgg gccaggtgtt cgaatcccga
 121 ctccagaact ggcggcgtcc cagtcccgcg ggcgtggagc ccggaggac ccgccctcgg
 181 gctcatggcg gccccggtcc gcctgggccg gaagcgcccg ctgcctgcct gtcccaaccc
 241 gctcttcgtt cgctggctga ccgagtggcg ggacgaggcg acccgcagca ggcaccgcac
 301 gcgcttcgta tttcagaagg cgctgcgttc cctccgacgg tacccactgc cgctgcgcag
 361 cgggaaggaa gctaagatcc tacagcactt cggagacggg ctctgccgga tgctggacga
 421 gcggctgcag cggcaccgaa catcgggcgg tgaccatgcc ccggactcac catctggaga
 481 gaacagtcca gccccgcagg ggcgacttgc ggaagtccag gactcttcca tgccagttcc
 541 tgcccagccc aaagcgggag gctctggcag ctactggcca gctcggcact caggagcccg
 601 agtgatactg ctggtgctct accgggagca cctgaatcct aatggtcacc acttcttaac
 661 caaggaggag ctgctgcaga ggtgtgctca agtccccc agggtagccc tgggagtgc
 721 cccaccctgg ccagccctcc gctccctcct tcacaggaac ctggtcctca ggacacacca
 781 gccagccagg tactcattga ccccagaggg cctggagctg gcccagaagt tggccgagtc
 841 agaaggcctg agcttgctga atgtgggcat cgggcccaag gagcccctg gggaggagac
 901 agcagtgcca ggagcagctt cagcagagct tgccagtgaa gcaggggtcc agcagcagcc
 961 actggagctg aggcctggag agtacagggt gctgttgtgt gtggacattg gcgagacccg
1021 gggggcggg cacaggccgg agctgctccg agagctacag cggctgcacg tgacccacac
1081 ggtgcgcaag ctgcacgttg gagattttgt gtgggtggct caggagacca tcctagaga
1141 cccagcaaac cctggggagt ggtactgga tcacattgtg gagcgcaagc gactggatga
1201 cctttgcagc agcatcatcg acggccgctt ccgggagcag aagttccgac tgaagcgctg
1261 tggtctggag cgccgggtat acctggtgga agagcatggt tccgtccaca acctcagctt
1321 tcttgagagc acacttgtgc aggctgtcac caacactcag gtcattgatg gcttttttgt
1381 gaagcgcaca gcagacatta aggagtcagc cgcctacctg gccctcttga ctcgggcct
1441 gcagagactc taccaggtga gcagaggccc ctttcccagt gtcgggacag agcccacaag
1501 gaattcacct tgcctgggcc ctgtgcatcc ccaaaagaag caaggtgggt gagatcccca
1561 tttctcaggc tggcccccca aggctgagga ctgggcaggg gctggctgga gttgttcctt
1621 cgagctccag cctggcctca gtccttctt ccctcagggc cacacctac gcagccgccc
1681 ctggggaacc cctgggaacc ctgaatcagg ggccatgacc tctccaaacc ctctctgctc
1741 actcctcacc ttcagtgact caacgcagg agccatcaag aataaggccc agtcggtgcg
1801 agaagtgttt gcccggcagc tgatgcaggt gcgcggagtg agtggggaga aggcagcagc
1861 cctggtggat cgatacagca ccctgccag cctcctggcc gcctatgatg cctgtgccac
1921 ccccaaggaa caagagacac tgctgagcac cattaagtgt gggcgtctac agaggaatct
1981 ggggcctgct ctgagcagga ccttatccca gtctactgc agctacggcc ccttgacctg
2041 agcttatgcc gtgaaacagc ccccagcccc cgtctgtccc caacccagg ctagccagcc
2101 ttttaacaac atcttttggg gtacaattag aatctaagtg tttgcagcca tatgtgtcat
2161 gtagaagatg cctagccctg gggaccttgt gaaatacgca ggaaccaggg ataccatctg
2221 gtccagtggt ttttaaacaa agctgcttag cacctggaat tccctggtca gggagatgga
2281 gtcagtgggg cattgcagct tggaatctat tttatgtcac cagttggtcc tcatcaaata
2341 aaatttcctt aggagtgcag agggctcatt gggaaaataa aaataataaa aataaataaa
2401 acttcctaaa agaaaagatt gaaaaccaaa aaaaaaaaaa aaaaaaacct cgtgccgaat
2461 tc (SEQ ID NO: 3)
```

```
   1 MAAPVRLGRK RPLPACPNPL FVRWLTEWRD EATRSRHRTR FVFQKALRSL RRYPLPLRSG
  61 KEAKILQHFG DGLCRMLDER LQRHRTSGGD HAPDSPSGEN SPAPQGRLAE VQDSSMPVPA
 121 QPKAGGSGSY WPARHSGARV ILLVLYREHL NPNGHHFLTK EELLQRCAQK SPRVAPGSAP
 181 PWPALRSLLH RNLVLRTHQP ARYSLTPEGL ELAQKLAESE GLSLLNVGIG PKEPPGEETA
 241 VPGAASAELA SEAGVQQQPL ELRPGEYRVL LCVDIGETRG GGHRPELLRE LQRLHVTHTV
 301 RKLHVGDFVW VAQETNPRDP ANPGELVLDH IVERKRLDDL CSSIIDGRFR EQKFRLKRCG
 361 LERRVYLVEE HGSVHNLSFL ESTLVQAVTN TQVIDGFFVK RTADIKESAA YLALLTRGLQ
 421 RLYQVSRGPF PSVGTEPTRN SPCLGPVHPQ KKQGG (SEQ ID NO: 4)
```

FIG. 1B

```
   1 gatatctgca gaattcgccc ttgacatggc ggccccggtc cgcctgggcc ggaagcgccc
  61 gctgcctgcc tgtcccaacc cgctcttcgt tcgctggctg accgagtggc gggacgaggc
 121 gacccgcagc aggcgccgca cgcgcttcgt atttcagaag gcgctgcgtt ccctccgacg
 181 gtacccactg ccgctgcgca gcgggaagga agctaagatc ctacagcact tcggagacgg
 241 gctctgccgg atgctggacg agcggctgca gcggcaccga acatcgggcg tgaccatgc
 301 ccggactca ccatctggag agaacagtcc agccccgcag gggcgacttg cggaagtcca
 361 ggactcttcc atgccagttc ctgcccagcc caaagcggga ggctctggca gctactggcc
 421 agctcggcac tcaggagccc gagtgatact gctggtgctc taccgggagc acctgaatcc
 481 taatggtcac cacttcttaa ccaaggagga gctgctgcag aggtgtgctc agaagtcccc
 541 cagggtagcc cctgggagtg ctcgaccctg ccagccctc cgctccctcc ttcacaggaa
 601 cctggtcctc aggacacacc agccagccag gtactcattg acccagagg gcctggagct
 661 ggcccagaag ttggccgagt cagaaggcct gagcttgctg aatgtgggca tcgggcccaa
 721 ggagccccct ggggaggaga cagcagtgcc aggagcagct tcagcagagc ttgccagtga
 781 agcaggggtc cagcagcagc cactggagct gaggcctgga gagtacaggg tgctgttgtg
 841 tgtggacatt ggcgagaccc ggggggggcgg gcacaggccg gagctgctcc gagagctaca
 901 gcggctgcac gtgacccaca cggtgcgcaa gctgcacgtt ggagatttg tgtgggtggc
 961 ccaggagacc aatcctagag acccagcaaa ccctggggag ttggtactgg atcacattgt
1021 ggagcgcaag cgactggatg accttgcag cagcatcatc gacggccgct tccgggagca
1081 gaagttccgg ctgaagcgct gtgtctgga gcgccgggta tacctggtgg aagagcatgg
1141 ttccgtccac aacctcagcc ttcctgagag cacactgctg caggctgtca ccaacactca
1201 ggtcattgat ggcttttttg tgaagcgcac agcagacatt aaggagtcag ccgcctacct
1261 ggccctcttg acgcggggcc tgcagagact ctaccagtga cttaacgca ggagccatca
1321 agaataaggc ccagtcggtg cgagaagtgt ttgccccgga gctgatgcag gtgcgcggag
1381 tgagtgggga aaggcagca gccctggtgg atcgatacag caccctgcc agcctcctgg
1441 ccgcctatga tgcctgtgcc accccaagg aacaagagac actgctgagc accattaagt
1501 gtgggcgtct acagaggaat ctggggcctg ctctgagcag gaccttatcc cagctctact
1561 gcagctacgg ccccttgacc tgagtcaagg gcgaattc (SEQ ID NO: 7)
```

```
  1 MAAPVRLGRK RPLPACPNPL FVRWLTEWRD EATRSRRRTR FVFQKALRSL RRYPLPLRSG
 61 KEAKILQHFG DGLCRMLDER LQRHRTSGGD HAPDSPSGEN SPAPQGRLAE VQDSSMPVPA
121 QPKAGGSGSY WPARHSGARV ILLVLYREHL NPNGHHFLTK EELLQRCAQK SPRVAPGSAR
181 PWPALRSLLH RNLVLRTHQP ARYSLTPEGL ELAQKLAESE GLSLLNVGIG PKEPPGEETA
241 VPGAASAELA SEAGVQQQPL ELRPGEYRVL LCVDIGETRG GHRPELLRE LQRLHVTHTV
301 RKLHVGDFVW VAQETNPRDP ANPGELVLDH IVERKRLDDL CSSIIDGRFR EQKFRLKRCG
361 LERRVYLVEE HGSVHNLSLP ESTLLQAVTN TQVIDGFFVK RTADIKESAA YLALLTRGLQ
421 RLYQ (SEQ ID NO: 8)
```

FIG. 1C

```
   1 gatatctgca gaattcgccc ttgacatggc ggccccggtc cgcctgggcc ggaagcgccc
  61 gctgcctgcc tgtcccaacc cgctcttcgt tcgctggctg accgagtggc gggacgaggc
 121 gacccgcagc aggcgccgca cgcgcttcgt atttcagaag gcgctgcgtt ccctccgacg
 181 gtacccactg ccgctgcgca gcgggaagga agctaagatc ctacagcact tcggagacgg
 241 gctctgccgg atgctggacg agcggctgca gcggcaccga acatcgggcg tgaccatgc
 301 cccggactca ccatctggag agaacagtcc agccccgcag gggcgacttg cggaagtcca
 361 ggactcttcc atgccagttc ctgcccagcc caaagcggga ggctctggca gctactggcc
 421 agctcggcac tcaggagccc gagtgatact gctggtgctc taccgggagc acctgaatcc
 481 taatggtcac cacttcttaa ccaaggagga gctgctgcag aggtgtgctc agaagtcccc
 541 cagggtagcc cctgggagtg ctcgaccctg gccagccctc cgctccctcc ttcacaggaa
 601 cctggtcctc aggacacacc agccagccag gtactcattg accccagagg gcctggagct
 661 ggcccagaag ttggccgagt cagaaggcct gagcttgctg aatgtgggca tcgggcccaa
 721 ggagccccct ggggaggaga cagcagtgcc aggagcagct cagcagagc ttgccagtga
 781 agcaggggtc cagcagcagc cactggagct gaggcctgga gagtacaggg tgctgttgtg
 841 tgtggacatt ggcgagaccc ggggggggcgg gcacaggccg gagctgctcc gagagctaca
 901 gcggctgcac gtgacccaca cggtgcgcaa gctgcacgtt ggagattttg tgtgggtggc
 961 ccaggagacc aatcctagag acccagcagc aaaccctggg gagttggtac tggatcacat
1021 tgtggagcgc aagcgactgg atgacctttg cagcagcatc atcgacggcc gcttccggga
1081 gcagaagttc cggctgaagc gctgtggtct ggagcgccgg gtatacctgg tggaagagca
1141 tggttccgtc cacaacctca gccttcctga gcacactg ctgcaggctg tcaccaacac
1201 tcaggtcatt gatggctttt ttgtgaagcg cacagcagac attaaggagt cagccgccta
1261 cctggccctc ttgacgcggg gcctgcagag actctaccag gccacaccc tacgcagccg
1321 cccctgggga accctggga accctgaatc aggggccatg acctctccaa accctctctg
1381 ctcactcctc accttcagtg acttcaacgc aggagccatc aagaataagg cccagtcggt
1441 gcgagaagtg tttgcccggc agctgatgca ggtgcgcgga gtgagtgggg agaaggcagc
1501 agccctggtg gatcgataca gcacccctgc cagcctcctg gccgcctatg atgcctgtgc
1561 cacccccaag gaacaagaga cactgctgag caccattaag tgtgggcgtc tacagaggaa
1621 tctggggcct gctctgagca ggaccttatc ccagctctac tgcagctacg gccccttgac
1681 ctgagtcaag ggcgaattc (SEQ ID NO: 9)
```

```
   1 MAAPVRLGRK RPLPACPNPL FVRWLTEWRD EATRSRRRTR FVFQKALRSL RRYPLPLRSG
  61 KEAKILQHFG DGLCRMLDER LQRHRTSGGD HAPDSPSGEN SPAPQGRLAE VQDSSMPVPA
 121 QPKAGGSGSY WPARHSGARV ILLVLYREHL NPNGHHFLTK EELLQRCAQK SPRVAPGSAR
 181 PWPALRSLLH RNLVLRTHQP ARYSLTPEGL ELAQKLAESE GLSLLNVGIG PKEPPGEETA
 241 VPGAASAELA SEAGVQQQPL ELRPGEYRVL LCVDIGETRG GGHRPELLRE LQRLHVTHTV
 301 RKLHVGDFVW VAQETNPRDP AANPGELVLD HIVERKRLDD LCSSIIDGRF REQKFRLKRC
 361 GLERRVYLVE EHGSVHNLSL PESTLLQAVT NTQVIDGFFV KRTADIKESA AYLALLTRGL
 421 QRLYQGHTLR SRPWGTPGNP ESGAMTSPNP LCSLLTFSDF NAGAIKNKAQ SVREVFARQL
 481 MQVRGVSGEK AAALVDRYST PASLLAAYDA CATPKEQETL LSTIKCGRLQ RNLGPALSRT
 541 LSQLYCSYGP LT (SEQ ID NO: 10)
```

FIG. 1D

```
   1 gaattcgccc ttgagactct gaaggagcca gtctagttct tatggcggag ccggtccgcc
  61 tgggccggaa gcgtccgctg cccgtttgcc ccaacccgct cttcgttcgt tggctgaccg
 121 agtggcggga cgaggcagcc agcaggggcc gccacacgcg tttcgtgttt caaaaggcat
 181 tgcgctccct ccaacggtac ccgctaccat tgcgcagcgg gaaggaagcc aagatactcc
 241 agcacttcgg agacaggctc tgccgcatgc tggacgaaaa gctgaagcag cacctagcat
 301 caggcggtga ccatgccccc agctcaccat ctggaaagaa gggagccagc aaagggccac
 361 ctgagcaagt ccaggactct tccatgccag ttccacccca gcctcaagca ggaagcacca
 421 gtgttggcta ttggccagct cagaactcag gtgctcgaga gatcctgctg caactctaca
 481 gggagcacct gaattctgat ggccacagct tcctaaccaa agaggagctg ctgcagaagt
 541 gtgcccagaa gacccccagg gtagtgcctg gaagttcgaa accctggcct gccctccgga
 601 gcctcctcca taggaacctc atccttggaa cgcatcggcc agccaggtat gcactcacac
 661 cagagggtct ggagctggct cagaagctgg ccgaggcgga aggcctgagc actcggcacg
 721 ctggctttag gccagaggaa catcacggag aggactcagc agttccagaa gccttgtcag
 781 aacctggcac caccgagggg gccgtccagc agagaccact ggagctaagg cctagcgagt
 841 acagagtgct gttgtgtgtg gacattggcg aaaccagagg ggcaggacac aggctagaaa
 901 tgctccgaga gttacaaagg ctgcgtgtgc cccacaccgt acgcaagcta cacgttggag
 961 actttgtgtg ggtggcacag gagaccaggc ccagagaccc agaaagacct ggggagctgg
1021 tcctggacca cattgtggaa cgcaagcggc tagatgacct atgcagcagc atcattgacg
1081 gccgctttcg ggagcagaag ttccgcctga gcgctgtgg cctggggcac cgggtatact
1141 tagtggaaga acatgggtct gtccacaacc ttagccttcc cgagagcacc ttgctgcagg
1201 ctgtcacaaa cacccaggtc attgatggct tttttgtgaa gcgaaccatg gatattaagg
1261 agtcggttgg ctacctggcg cttttgacaa agggcctgga agactgtac cagggccaca
1321 ccctacgcag ccgcccttgg ggggccccag gggctgctga atcagaagca aagccttcca
1381 caaaccctct ctgctcactc ctcaccttca gtgacttcaa tgcagaagct gtcaagaaca
1441 aggcccagtc tgtgcgagaa gtatttgccc ggcagctgat gcaggtgcgt ggactgagtg
1501 gggagaaggc agcagccgtg tggatcgat acagcacccc tgccagtctc ctggctgctt
1561 atgatgcctg tgccaccgcg aaggagcagg agatgctctt gagcaccatc aagtgtgggc
1621 gtctgcagag gaatctggga cccgctctga gcaggaccct gtaccagttg tactgcagcc
1681 acagccctct gagctgagct gtaccaggag acgctcgctc cccagcaccc atcttcatct
1741 ctaccaaggc tggctagcct tttagcaagg gcgaattctg cagatatc (SEQ ID NO: 11)
```

```
  1 MAEPVRLGRK RPLPVCPNPL FVRWLTEWRD EAASRGRHTR FVFQKALRSL QRYPLPLRSG
 61 KEAKILQHFG DRLCRMLDEK LKQHLASGGD HAPSSPSGKK GASKGPPEQV QDSSMPVPTQ
121 PQAGSTSVGY WPAQNSGARE ILLQLYREHL NSDGHSFLTK EELLQKCAQK TPRVVPGSSK
181 PWPALRSLLH RNLILGTHRP ARYALTPEGL ELAQKLAEAE GLSTRHAGFR PEEHHGEDSA
241 VPEALSEPGT TEGAVQQRPL ELRPSEYRVL LCVDIGETRG AGHRLEMLRE LQRLRVPHTV
301 RKLHVGDFVW VAQETRPRDP ERPGELVLDH IVERKRLDDL CSSIIDGRFR EQKFRLKRCG
361 LGHRVYLVEE HGSVHNLSLP ESTLLQAVTN TQVIDGFFVK RTMDIKESVG YLALLTKGLE
421 RLYQGHTLRS RPWGAPGAAE SEAKPSTNPL CSLLTFSDFN AEAVKNKAQS VREVFARQLM
481 QVRGLSGEKA AVVDRYSTP ASLLAAYDAC ATAKEQEMLL STIKCGRLQR NLGPALSRTL
541 YQLYCSHSPL S (SEQ ID NO: 12)
```

FIG. 2A

```
   1 gatatctgca gaattcgccc ttgagactct gaaggagcca gtctagttct tatggcggag
  61 ccggtccgcc tgggccggaa gcgtccgctg cccgtttgcc ccaacccgct cttcgttcgt
 121 tggctgaccg agtggcggga cgaggcagcc agcaggggc gccacacgcg tttcgtgttt
 181 caaaaggcat gcgctccct ccaacggtac ccgctaccat tgcgcagcgg gaaggaagcc
 241 aagatactcc agcacttcgg agacaggctc tgccgcatgc tggacgaaaa gctgaagcag
 301 cacctagcat caggcggtga ccatgccccc agctcaccat ctggaaagaa gggagccagc
 361 aaagggccac ctgagcaagt ccaggactct tccatgccag ttccacccca gcctcaagca
 421 ggaagcacca gtgttggcta ttggccagct cagaactcag gtgctcgaga gatcctgctg
 481 caactctaca gggagcacct gaattctgat ggccacagct tcctaaccaa agaggagctg
 541 ctgcagaagt gtgcccagaa gacccccagg gtagtgcctg gaagttcgaa accctggcct
 601 gccctccgga gcctcctcca taggaacctc atccttggaa cgcatcggcc agccaggtat
 661 gcactcacac cagagggtct ggagctggct cagaagctgg ccgaggcgga aggcctgagc
 721 actcggcacg ctggctttag gccagaggaa catcacggag aggactcagc agttccagaa
 781 gccttgtcag aacctggcac caccgagggg gccgtccagc agagaccact ggagctaagg
 841 cctagcgagt acagagtgct gttgtgtgtg gacattggcg aaaccagagg ggcaggacac
 901 aggccagaaa tgctccgaga gttacaaagg ctgcgtgtgc cccacaccgt acgcaagcta
 961 cacgttggag actttgtgtg ggtggcacag gagaccaggc ccagagaccc agaaagacct
1021 ggggagctgg tcctggacca cattgtggaa cgcaagcggc tagatgacct atgcagcagc
1081 atcattgacg gccgctttcg ggagcagaag ttccgcctga gcgctgtgg cctggggcac
1141 cgggtatact tagtggaaga acatgggtct gtccacaacc ttagccttcc cgagagcacc
1201 ttgctgcagg ctgtcacaaa cacccaggtc attgatggct tttttgtgaa gcgaaccatg
1261 gatattaagg agtcggttgg ctacctggcg cttttgacaa agggcctgga agactgtac
1321 cagtgacttc aatgcagaag ctgtcaagaa caaggtacca ccctgcctc acctctgctc
1381 gggtggccta ggccaaggtc acccttaaca caggcctacc caacccag gccagtctg
1441 tgcgagaagt atttgcccgg cagctgatgc aggtgcgtgg actgagtggg gagaaggcag
1501 cagccgtggt ggatcgatac agcacccctg ccagtctcct ggctgcttat gatgcctgtg
1561 ccaccgcgaa ggagcaggag atgctcttga gcaccatcaa gtgtgggcgt ctgcagagga
1621 atctgggacc cgctctgagc aggaccctgt accagttgta ctgcagccac agccctctga
1681 gctgagctgt accaggagac gctcgctccc cagcacccat cttcatctct accaaggctg
1741 gctagccttt tagcaagggc gaattc (SEQ ID NO: 13)
```

```
   1 MAEPVRLGRK RPLPVCPNPL FVRWLTEWRD EAASRGRHTR FVFQKALRSL QRYPLPLRSG
  61 KEAKILQHFG DRLCRMLDEK LKQHLASGGD HAPSSPSGKK GASKGPPEQV QDSSMPVPTQ
 121 PQAGSTSVGY WPAQNSGARE ILLQLYREHL NSDGHSFLTK EELLQKCAQK TPRVVPGSSK
 181 PWPALRSLLH RNLILGTHRP ARYALTPEGL ELAQKLAEAE GLSTRHAGFR PEEHHGEDSA
 241 VPEALSEPGT TEGAVQQRPL ELRPSEYRVL LCVDIGETRG AGHRPEMLRE LQRLRVPHTV
 301 RKLHVGDFVW VAQETRPRDP ERPGELVLDH IVERKRLDDL CSSIIDGRFR EQKFRLKRCG
 361 LGHRVYLVEE HGSVHNLSLP ESTLLQAVTN TQVIDGFFVK RTMDIKESVG YLALLTKGLE
 421 RLYQ (SEQ ID NO: 14)
```

FIG. 2B

```
   1 gatatctgca gaattcgccc ttgagactct gaaggagcca gtctagttct tatggcggag
  61 ccggtccgcc tgggccggaa gcgtccgctg cccgtttgcc ccaacccgct cttcgttcgt
 121 tggctgaccg agtggcggga cgaggcagcc agcaggggc gccacacgcg tttcgtgttt
 181 caaaaggcat tgcgctccct ccaacggtac ccgctaccat tgcgcagcgg gaaggaagcc
 241 aagatactcc agcacttcgg agacaggctc tgccgcatgc tggacgaaaa gctgaagcag
 301 cacctagcat caggcggtga ccatgccccc agctcaccat ctggaaagaa gggagccagc
 361 aaagggccac tgagcaagt ccaggactct tccatgccag ttcccaccca gcctcaagca
 421 ggaagcacca gtgttggcta ttggccagct cagaactcag gtgctcgaga gatcctgctg
 481 caactctaca gggagcacct gaattctgat ggccacagct tcctaaccaa agaggagctg
 541 ctgcagaagt gtgcccagaa gacccccagg gtagtgcctg gaagttcgaa accctggcct
 601 gccctccgga gcctcctcca taggaacctc atccttggaa cgcatcggcc agccaggtat
 661 gcactcacac cagagggtct ggagctggct cagaagctgg ccgaggcgga aggcctgagc
 721 actcggcacg ctggctttag ccagaggaa catcacggag aggactcagc agttccagaa
 781 gccttgtcag aacctggcac caccgagggg gccgtccagc agagaccact ggagctaagg
 841 cctagcgagt acagagtgct gttgtgtgtg gacattggcg aaaccagagg ggcaggacac
 901 aggccagaaa tgctccgaga gttacaaagg ctgcgtgtgc cccacaccgt acgcaagcta
 961 cacgttggag actttgtgtg ggtggcacag agaccaggc ccagagaccc agaaagacct
1021 ggggagctgg tcctggacca cattgtggaa cgcaagcggc tagatgacct atgcagcagc
1081 atcattgacg gccgctttcg ggagcagaag ttccgcctga gcgctgtgg cctggggcac
1141 cgggtatact tagtggaaga acatgggtct gtccacaacc ttagccttcc cgagagcacc
1201 ttgctgcagg ctgtcacaaa cacccaggtc attgatggct tttttgtgaa gcgaaccatg
1261 gatattaagg agtcggttgg ctacctggcg cttttgacaa agggcctgga agactgtac
1321 cagccttcca caaaccctct ctgctcactc ctccttca gtgacttcaa tgcagaagct
1381 gtcaagaaca aggcccagtc tgtgcagaa gtatttgccc ggcagctgat gcaggtgcgt
1441 ggactgagtg gggagaaggc agcagccgtg gtggatcgat acagcaccc tgccagtctc
1501 ctgctgctt atgatgcctg tgccaccgcg aaggagcagg agatgctctt gagcaccatc
1561 aagtgtgggc gtctgcagag gaatctggga cccgctctga caggacct gtaccagttg
1621 tactgcagcc acagccctct gagctgagct gtaccaggag acgctcgctc cccagcaccc
1681 atcttcatct ctaccaaggc tggctagcct tttagcaagg gcgaattcca gcacactggc
1741 ggccgttact agtggatccg agctcggtac caagcttggc gtaatcatgg tcatagctgt
1801 ttcctgtgtg aaattgttat ccgctcacaa ttccacacaa catacgagcc ggaagcataa
1861 agtgtaaagc ctggggtgcc taatgagtga gctaactcac attaattgcg ttgcgctcac
1921 tgcccgcttt ccagtcggga aacctgtcgt gccagctgca ttaatgaatc ggccaacgcg
1981 cggggagagg cggtttgcgt attgggcgct cttccg (SEQ ID NO: 15)
```

```
   1 MAEPVRLGRK RPLPVCPNPL FVRWLTEWRD EAASRGRHTR FVFQKALRSL QRYPLPLRSG
  61 KEAKILQHFG DRLCRMLDEK LKQHLASGGD HAPSSPSGKK GASKGPPEQV QDSSMPVPTQ
 121 PQAGSTSVGY WPAQNSGARE ILLQLYREHL NSDGHSFLTK EELLQKCAQK TPRVVPGSSK
 181 PWPALRSLLH RNLILGTHRP ARYALTPEGL ELAQKLAEAE GLSTRHAGFR PEEHHGEDSA
 241 VPEALSEPGT TEGAVQQRPL ELRPSEYRVL LCVDIGETRG AGHRPEMLRE LQRLRVPHTV
 301 RKLHVGDFVW VAQETRPRDP ERPGELVLDH IVERKRLDDL CSSIIDGRFR EQKFRLKRCG
 361 LGHRVYLVEE HGSVHNLSLP ESTLLQAVTN TQVIDGFFVK RTMDIKESVG YLALLTKGLE
 421 RLYQPSTNPL CSLLTFSDFN AEAVKNKAQS VREVFARQLM QVRGLSGEKA AAVVDRYSTP
 481 ASLLAAYDAC ATAKEQEMLL STIKCGRLQR NLGPALSRTL YQLYCSHSPL S (SEQ ID NO: 16)
```

FIG. 2C

```
   1 gatatctgca gaattcgccc ttgagactct gaaggagcca gtctagttct tatggcggag
  61 ccggtccgcc tgggccggaa gcgtccgctg cccgtttgcc ccaacccgct cttcgtttgt
 121 tggctgaccg agtggcggga cgaggcagcc agcaggggc gccacacgcg tttcgtgttt
 181 caaaaggcat tgcgctccct ccaacggtac ccgctaccat tgcgcagcgg aaggaagcc
 241 aagatactcc agcacttcgg agacaggctc tgccgcatgc tggacgaaaa gctgaagcag
 301 cacctagcat caggcggtga ccatgccccc agctccacca ctggaaagaa gggagccagc
 361 aaagggccac ctgagcaagt ccaggactct tccatgccag ttcccaccca gcctcaagca
 421 ggaagcacca gtgttggcta ttggccagct cagaactcag gtgctcgaga gatcctgctg
 481 caactctaca gggagcacct gaattctgat ggccacagct cctaaccaa agaggagctg
 541 ctgcagaagt gtgcccagaa gacccccagg gtagtgcctg gaagttcgaa accctggcct
 601 gccctccgga gcctcctcca taggaacctc atccttggaa cgcatcggcc agccaggtat
 661 gcactcacac cagagggtct ggagctggct cagaagctgg ccgaggcgga aggcctgagc
 721 actcggcacg ctggctttag gccagaggaa catcacggag aggactcagc agttccagaa
 781 gccttgtcag aacctggcac caccgagggg gccgtccagc agagaccact ggagctaagg
 841 cctagcgagt acagagtgct gttgtgtgtg gacattggcg aaaccagagg ggcaggacac
 901 aggccagaaa tgctccgaga gttacaaagg ctgcgtgtgc cccacaccgt acgcaagcta
 961 cacgttggag actttgtgtg ggtggcacag agaccaggc cagagaccc agaaagacct
1021 ggggagctgg tcctggacca cattgtggaa cgcaagcggc tagatgacct atgcagcagc
1081 atcattgacg gccgctttcg ggagcagaag ttccgcctga gcgctgtgg cctggggcac
1141 cgggtatact tagtggaaga acatgggtct gtccacaacc ttagccttcc cgagagcacc
1201 ttgctgcagg ctgtcacaaa cacccaggtc attgatggct ttttgtgaa gcgaaccatg
1261 gatattaagg agtcggttgg ctacctggcg cttttgacaa agggcctgga agactgtac
1321 caggccaagg tcaccttaa cacaggccta ccccaacccc aggcccagtc tgtgcgagaa
1381 gtatttgccc ggcagctgat gcaggtgcgt ggactgagtg gggagaaggc agcagccgtg
1441 gtggatcgat acagcacccc tgccagtctc ctggctgctt atgatgcctg tgccaccgcg
1501 aaggagcagg agatgctctt gagcaccatc aagtgtgggc gtctgcagag gaatctggga
1561 cccgctctga caggaccct gtaccagttg tactgcagcc acagccctct gagctgagct
1621 gtaccaggag acgctcgctc cccagcaccc atcttcatct ctaccaaggc tggctagcct
1681 tttagcaagg gcgaattc (SEQ ID NO: 17)
```

```
   1 MAEPVRLGRK RPLPVCPNPL FVCWLTEWRD EAASRGRHTR FVFQKALRSL QRYPLPLRSG
  61 KEAKILQHFG DRLCRMLDEK LKQHLASGGD HAPSSPSGKK GASKGPPEQV QDSSMPVPTQ
 121 PQAGSTSVGY WPAQNSGARE ILLQLYREHL NSDGHSFLTK EELLQKCAQK TPRVVPGSSK
 181 PWPALRSLLH RNLILGTHRP ARYALTPEGL ELAQKLAEAE GLSTRHAGFR PEEHHGEDSA
 241 VPEALSEPGT TEGAVQQRPL ELRPSEYRVL LCVDIGETRG AGHRPEMLRE LQRLRVPHTV
 301 RKLHVGDFVW VAQETRPRDP ERPGELVLDH IVERKRLDDL CSSIIDGRFR EQKFRLKRCG
 361 LGHRVYLVEE HGSVHNLSLP ESTLLQAVTN TQVIDGFFVK RTMDIKESVG YLALLTKGLE
 421 RLYQAKVTLN TGLPQPQAQS VREVFARQLM QVRGLSGEKA AVVDRYSTP ASLLAAYDAC
 481 ATAKEQEMLL STIKCGRLQR NLGPALSRTL YQLYCSHSPL S (SEQ ID NO: 18)
```

FIG. 2D

```
Mm : ----------------------------------------------------------
Hs : ----------------------------------------------------------
Sp : ---------------------------------------MKSCPITFHRPSQALA
Sc : MELSSNLKDLYIEWLQELVDGLTPKQEQLKIAYEKAKRNLQNAEGSFYYPTDLKK

Mm : -----MAEPVRLGRKRPLPVCPNPLF-----------VRWLTEWRDEAASRGRHT   :  39
Hs : -----MAAPVRLGRKRPLPACPNPLF-----------VRWLTEWRDEATRSRHRT   :  39
Sp : LKGIGPTICAKLEKKWNAYCLENNIP-----------ISTHNEQNDSHVNANKSS   :  60
Sc : VKGIGNTIIKRLDTKLRNYCKIHHISPVEAPSLTQTSSTRPPKRTTIALRSIVNS   : 110

Mm : RFVFQKALRSLQRYPLPLRSGKEAKILQHFGDRLCRMLDEK-LKQHLASGGDHAP
Hs : RFVFQKALRSLRRYPLPLRSGKEAKILQHFGDGLCRMLDER-LQRHRTSGGDHAP
Sp : SETSSEKPRSVKKPTTRKRKVYVPSYRSGAYSILCALYMLN-KHEFATKPQIVTM
Sc : CENDKNEAPEEKGTKKRKTRKYIPKKRSGGYAILLSLLELNAIPRGVSKEQIIEV

Mm : SSPSGKKG----ASKGPPEQVQDSSMPVPTQPQAGSTSVGYWPAQNSGAREILLQ   : 144
Hs : DSPSGENSP---APQGRLAEVQDSSMPVPAQPKAGGSG-SYWPARHSGARVILLV   : 144
Sp : AQPYCDSSFGSATDRNMRYTAWSAMKTLITKNLVYQTGHPSKYCLTDDGEEVCIR   : 169
Sc : AGKYSDHCMTPNFSTKEFYGAWSSIAALKKHSLVLEEGRPKRYSLTEEGVELTKS   : 220

Mm : LYREHLNSDGHSFLTKEELLQKCAQKTPRVVPGS--SKPWPALRSLLHRNLILGT
Hs : LYREHLNPNGHHFLTKEELLQRCAQKSPRVAPGS--APPWPALRSLLHRNLVLRT
Sp : LAKVDDSFQRKHTVSNFSVSKSDDHDSSLCQPPNFVTSINKAGSSSDHGGELHVT
Sc : LKTADGISFPKENEEPNEYSVTRNESSEFTANLTDLRGEYGKEEEPCDINNTSFM

Mm : HRPARYALTPEGLELAQKLAEAEGLSTRHAGFRPEEHHGEDSAVPEALSEPGTTE   : 252
Hs : HQPARYSLTPEGLELAQKLAESEGLSLLNVGIGPKEPPGEETAVPGAASAELASE   : 252
Sp : YCPVDHNEVSDGVETDIDVDQVDSLTGIHDHHIINNEQLIDLTEQEKKQPNESNL   : 279
Sc : LDITFQDLSTPQRLQNNVFKNDRLNSQTNISSHKLEEVSDDQTVPDSALKAKSTI   : 330
```

FIG. 3A

```
Mm : GAVQQRPLELR---PSEYRVLLCVDIGETRGAGHRPEMLRELQR-LRVPHTVRKL
Hs : AGVQQQPLELR---PGEYRVLLCVDIGETRGGHRPELLRELQR-LHVTHTVRKL
Sp : SNLKIETVLF-----SNCTVFLLIDTREIRSPLDRNLIIDKLTNDFGVNCQVRSL
Sc : KRRRYNGVSYELWCSGDFEVFPIIDHREIKSQSDREFFSRAFER-KGMKSEIRQL

Mm : HVGDFVWVAQETRPRDPE-RPGELVLDHIVERKRLDDLCSSIIDGRFREQKFRLK : 357
Hs : HVGDFVWVAQETNPRDPAANPGELVLDHIVERKDLDDLCSSIIDGRFREQKFRLK : 358
Sp : ELGDALWVARDMESGQEV-----VLDFVVERKRYDDLVASIKDGRFHEQKARLK : 378
Sc : ALGDIIWVAKNKNTGLQC-----VLNTIVERKRLDDLALSIRDNRFMEQKNRLE : 433

Mm : RCGLGHRVYLVEEHGSVHNLSLPESTLLQAVINTQVIDGFFVKRTMDIKESVGYL
Hs : RCGLERRVYLVEEHGSVHNLSLPESTLLQAVINTQVIDGFFVKRTADIKESAAYL
Sp : KSGIRSVTYILEESSYDESFT---ESIRTAVSNTQVDQLFHVRHIRSLEHSVSLL
Sc : KSGCEHKYYLIEETMSGNIGNM-NEALKTALWVILVYYKFSMIRTCNSDEIVEKI

Mm : ALLTKGLERLYQGHTLRSRPWGAPGAAESEAKPSTNPLC--------SLLTFSD : 458
Hs : ALLTRGLQRLYQGHTLRSRPWGTPGNPESGAMTSPNPLC--------SLLTFSD : 459
Sp : AEMTKQINLFYEKRKTLAVIPDLSIEAKTYESLREQLLKI---DPSTPYHISYHA : 482
Sc : HALHTVISHHYSQKDLIVIFPSDLKSKDDYKKVLLQFRREFERKGGIECCHNLEC : 542

Mm : FNAEAVKNKAQSVREVFARQLMQVRGLSGEKAAAVMDRYSTPASLLAAYDACATA
Hs : FNAGAIKNKAQSVREVFARQLMQVRGVSGEKAAALVDRYSTPASLLAAYDACATP
Sp : FSSVLSKSSTLTVGDIFIRMLMTIKGISASKAIEIQKKYPIFMHLFEAYEKSSSS
Sc : FQELMGKGDLKTVGELTIHVLMLVKGISLEKAVAIQEIFPILNKILMAYKTCSSE

Mm : KEQEMLL-STIKCGRLQRNLGPALSRTLYQLYCSHSPLS : 551 (SEQIDNO. : 12)
Hs : KEQETLL-STIKCGRLQRNLGPALSRTLSQLYCSYGPLT : 552 (SEQIDNO. : 10)
Sp : QERNLLL-NKTCQGYGFQTIGPALSAKVASVFFPES--- : 572 (SEQIDNO. : 6)
Sc : EEAKLLMFNVLGDAPGAKKITKSLSEKIYDAFGKL---- : 632 (SEQIDNO. : 5)
```

FIG. 3B

Co-immunoprecipitation of Mus81-HA and Cds1-FLAG

SEQUENCE LISTING

```
<160> NUMBER OF SEQ ID NOS: 33

<210> SEQ ID NO 1
<211> LENGTH: 1693
<212> TYPE: DNA
<213> ORGANISM: Homo sapiens
<220> FEATURE:
<221> NAME/KEY: CDS
<222> LOCATION: (23)..(1675)
<223> OTHER INFORMATION: Human Mus81(1)

<400> SEQUENCE: 1
gatatctgca gaattcgccc tt atg gcg gcc ccg gtc cgc ctg ggc cgg aag      52
                        Met Ala Ala Pro Val Arg Leu Gly Arg Lys
                         1               5                  10 cgc ccg ctg cct gcc tgt ccc aac ccg ctc ttc gtt cgc tgg ctg acc     100
Arg Pro Leu Pro Ala Cys Pro Asn Pro Leu Phe Val Arg Trp Leu Thr
             15                  20                  25 gag tgg cgg gac gag gcg acc cgc agc agg cac cgc acg cgc ttc gta     148
Glu Trp Arg Asp Glu Ala Thr Arg Ser Arg His Arg Thr Arg Phe Val
         30                  35                  40 ttt cag aag gcg ctg cgt tcc ctc cga cgg tac cca ctg ccg ctg cgc     196
Phe Gln Lys Ala Leu Arg Ser Leu Arg Arg Tyr Pro Leu Pro Leu Arg
     45                  50                  55 agc ggg aag gaa gct aag atc cta cag cac ttc gga gac ggg ctc tgc     244
Ser Gly Lys Glu Ala Lys Ile Leu Gln His Phe Gly Asp Gly Leu Cys
 60                  65                  70 cgg atg ctg gac gag cgg ctg cag cgg cac cga aca tcg ggc ggt gac     292
Arg Met Leu Asp Glu Arg Leu Gln Arg His Arg Thr Ser Gly Gly Asp
 75                  80                  85                  90 cat gcc ccg gac tca cca tct gga gag aac agt cca gcc ccg cag ggg     340
His Ala Pro Asp Ser Pro Ser Gly Glu Asn Ser Pro Ala Pro Gln Gly
                 95                 100                 105 cga ctt gcg gaa gtc cag gac tct tcc atg cca gtt cct gcc cag ccc     388
Arg Leu Ala Glu Val Gln Asp Ser Ser Met Pro Val Pro Ala Gln Pro
             110                 115                 120
```

| | |
|---|---:|
| aaa gcg gga ggc tct ggc agc tac tgg cca gct cgg cac tca gga gcc<br>Lys Ala Gly Gly Ser Gly Ser Tyr Trp Pro Ala Arg His Ser Gly Ala<br>              125                       130                   135 | 436 |
| cga gtg ata ctg ctg gtg ctc tac cgg gag cac ctg aat cct aat ggt<br>Arg Val Ile Leu Leu Val Leu Tyr Arg Glu His Leu Asn Pro Asn Gly<br>    140                       145                     150 | 484 |
| cac cac ttc tta acc aag gag gag ctg ctg cag agg tgt gct cag aag<br>His His Phe Leu Thr Lys Glu Glu Leu Leu Gln Arg Cys Ala Gln Lys<br>155                     160                     165                  170 | 532 |
| tcc ccc agg gta gcc cct ggg agt gcc cca ccc tgg cca gcc ctc cgc<br>Ser Pro Arg Val Ala Pro Gly Ser Ala Pro Pro Trp Pro Ala Leu Arg<br>              175                     180                   185 | 580 |
| tcc ctc ctt cac agg aac ctg gtc ctc agg aca cac cag cca gcc agg<br>Ser Leu Leu His Arg Asn Leu Val Leu Arg Thr His Gln Pro Ala Arg<br>    190                       195                     200 | 628 |
| tac tca ttg acc cca gag ggc ctg gag ctg gcc cag aag ttg gcc gag<br>Tyr Ser Leu Thr Pro Glu Gly Leu Glu Leu Ala Gln Lys Leu Ala Glu<br>              205                     210                   215 | 676 |
| tca gaa ggc ctg agc ttg ctg aat gtg ggc atc ggg ccc aag gag ccc<br>Ser Glu Gly Leu Ser Leu Leu Asn Val Gly Ile Gly Pro Lys Glu Pro<br>    220                       225                     230 | 724 |
| cct ggg gag gag aca gca gtg cca gga gca gct tca gca gag ctt gcc<br>Pro Gly Glu Glu Thr Ala Val Pro Gly Ala Ala Ser Ala Glu Leu Ala<br>235                     240                     245                  250 | 772 |
| agt gaa gca ggg gtc cag cag cag cca ctg gag ctg agg cct gga gag<br>Ser Glu Ala Gly Val Gln Gln Gln Pro Leu Glu Leu Arg Pro Gly Glu<br>              255                     260                   265 | 820 |
| tac agg gtg ctg ttg tgt gtg gac att ggc gag acc cgg ggg ggc ggg<br>Tyr Arg Val Leu Leu Cys Val Asp Ile Gly Glu Thr Arg Gly Gly Gly<br>    270                       275                     280 | 868 |
| cac agg ccg gag ctg ctc cga gag cta cag cgg ctg cac gtg acc cac<br>His Arg Pro Glu Leu Leu Arg Glu Leu Gln Arg Leu His Val Thr His<br>              285                     290                   295 | 916 |
| acg gtg cgc aag ctg cac gtt gga gat ttt gtg tgg gtg gct cag gag<br>Thr Val Arg Lys Leu His Val Gly Asp Phe Val Trp Val Ala Gln Glu<br>    300                       305                     310 | 964 |
| acc aat cct aga gac cca gca aac cct ggg gag ttg gta ctg gat cac<br>Thr Asn Pro Arg Asp Pro Ala Asn Pro Gly Glu Leu Val Leu Asp His<br>315                     320                     325                  330 | 1012 |
| att gtg gag cgc aag cga ctg gat gac ctt tgc agc agc atc atc gac<br>Ile Val Glu Arg Lys Arg Leu Asp Asp Leu Cys Ser Ser Ile Ile Asp<br>              335                     340                   345 | 1060 |
| ggc cgc ttc cgg gag cag aag ttc cga ctg aag cgc tgt ggt ctg gag<br>Gly Arg Phe Arg Glu Gln Lys Phe Arg Leu Lys Arg Cys Gly Leu Glu<br>    350                       355                     360 | 1108 |
| cgc cgg gta tac ctg gtg gaa gag cat ggt tcc gtc cac aac ctc agc<br>Arg Arg Val Tyr Leu Val Glu Glu His Gly Ser Val His Asn Leu Ser<br>              365                     370                   375 | 1156 |
| ctt cct gag agc aca ctg ctg cag gct gtc acc aac act cag gtc att<br>Leu Pro Glu Ser Thr Leu Leu Gln Ala Val Thr Asn Thr Gln Val Ile<br>    380                       385                     390 | 1204 |
| gat ggc ttt ttt gtg aag cgc aca gca gac att aag gag tca gcc gcc<br>Asp Gly Phe Phe Val Lys Arg Thr Ala Asp Ile Lys Glu Ser Ala Ala<br>395                     400                     405                  410 | 1252 |
| tac ctg gcc ctc ttg act cgg ggc ctg cag aga ctc tac cag ggc cac<br>Tyr Leu Ala Leu Leu Thr Arg Gly Leu Gln Arg Leu Tyr Gln Gly His<br>              415                     420                   425 | 1300 |
| acc cta cgc agc cgc ccc tgg gga acc cct ggg aac cct gaa tca ggg<br>Thr Leu Arg Ser Arg Pro Trp Gly Thr Pro Gly Asn Pro Glu Ser Gly<br>    430                       435                     440 | 1348 |

-continued

| | | | | | | | | | | | | | | | | |
|---|---|---|---|---|---|---|---|---|---|---|---|---|---|---|---|---|
| gcc | atg | acc | tct | cca | aac | cct | ctc | tgc | tca | ctc | ctc | acc | ttc | agt | gac | 1396 |
| Ala | Met | Thr | Ser | Pro | Asn | Pro | Leu | Cys | Ser | Leu | Leu | Thr | Phe | Ser | Asp | |
| | 445 | | | | 450 | | | | | 455 | | | | | | |

| | | | | | | | | | | | | | | | | |
|---|---|---|---|---|---|---|---|---|---|---|---|---|---|---|---|---|
| ttc | aac | gca | gga | gcc | atc | aag | aat | aag | gcc | cag | tcg | gtg | cga | gaa | gtg | 1444 |
| Phe | Asn | Ala | Gly | Ala | Ile | Lys | Asn | Lys | Ala | Gln | Ser | Val | Arg | Glu | Val | |
| | 460 | | | | 465 | | | | | 470 | | | | | | |

| | | | | | | | | | | | | | | | | |
|---|---|---|---|---|---|---|---|---|---|---|---|---|---|---|---|---|
| ttt | gcc | cgg | cag | ctg | atg | cag | gtg | cgc | gga | gtg | agt | ggg | gag | aag | gca | 1492 |
| Phe | Ala | Arg | Gln | Leu | Met | Gln | Val | Arg | Gly | Val | Ser | Gly | Glu | Lys | Ala | |
| 475 | | | | 480 | | | | | 485 | | | | | 490 | | |

| | | | | | | | | | | | | | | | | |
|---|---|---|---|---|---|---|---|---|---|---|---|---|---|---|---|---|
| gca | gcc | ctg | gtg | gat | cga | tac | agc | acc | cct | gcc | agc | ctc | ctg | gcc | gcc | 1540 |
| Ala | Ala | Leu | Val | Asp | Arg | Tyr | Ser | Thr | Pro | Ala | Ser | Leu | Leu | Ala | Ala | |
| | | | 495 | | | | | 500 | | | | | 505 | | | |

| | | | | | | | | | | | | | | | | |
|---|---|---|---|---|---|---|---|---|---|---|---|---|---|---|---|---|
| tat | gat | gcc | tgt | gcc | acc | ccc | aag | gaa | caa | gag | aca | ctg | ctg | agc | acc | 1588 |
| Tyr | Asp | Ala | Cys | Ala | Thr | Pro | Lys | Glu | Gln | Glu | Thr | Leu | Leu | Ser | Thr | |
| | | | 510 | | | | | 515 | | | | | 520 | | | |

| | | | | | | | | | | | | | | | | |
|---|---|---|---|---|---|---|---|---|---|---|---|---|---|---|---|---|
| att | aag | tgt | ggg | cgt | cta | cag | agg | aat | ctg | ggg | cct | gct | ctg | agc | agg | 1636 |
| Ile | Lys | Cys | Gly | Arg | Leu | Gln | Arg | Asn | Leu | Gly | Pro | Ala | Leu | Ser | Arg | |
| | | 525 | | | | | 530 | | | | | 535 | | | | |

| | | | | | | | | | | | | | | |
|---|---|---|---|---|---|---|---|---|---|---|---|---|---|---|
| acc | tta | tcc | cag | ctc | tac | tgc | agc | tac | ggc | ccc | ttg | acc | tgagtcaagg | 1685 |
| Thr | Leu | Ser | Gln | Leu | Tyr | Cys | Ser | Tyr | Gly | Pro | Leu | Thr | | |
| 540 | | | | | 545 | | | | | 550 | | | | |

| | |
|---|---|
| gcgaattc | 1693 |

<210> SEQ ID NO 2
<211> LENGTH: 551
<212> TYPE: PRT
<213> ORGANISM: Homo sapiens

<400> SEQUENCE: 2

Met Ala Ala Pro Val Arg Leu Gly Arg Lys Arg Pro Leu Pro Ala Cys
1               5                   10                  15

Pro Asn Pro Leu Phe Val Arg Trp Leu Thr Glu Trp Arg Asp Glu Ala
            20                  25                  30

Thr Arg Ser Arg His Arg Thr Arg Phe Val Phe Gln Lys Ala Leu Arg
        35                  40                  45

Ser Leu Arg Arg Tyr Pro Leu Pro Leu Arg Ser Gly Lys Glu Ala Lys
    50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Pro Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Glu Gly Leu Ser Leu
    210                 215                 220

| Leu | Asn | Val | Gly | Ile | Gly | Pro | Lys | Glu | Pro | Pro | Gly | Glu | Glu | Thr | Ala |
|-----|-----|-----|-----|-----|-----|-----|-----|-----|-----|-----|-----|-----|-----|-----|-----|
| 225 | | | | | 230 | | | | | 235 | | | | | 240 |
| Val | Pro | Gly | Ala | Ala | Ser | Ala | Glu | Leu | Ala | Ser | Glu | Ala | Gly | Val | Gln |
| | | | | 245 | | | | | 250 | | | | | 255 | |
| Gln | Gln | Pro | Leu | Glu | Leu | Arg | Pro | Gly | Glu | Tyr | Arg | Val | Leu | Leu | Cys |
| | | | 260 | | | | | 265 | | | | | 270 | | |
| Val | Asp | Ile | Gly | Glu | Thr | Arg | Gly | Gly | His | Arg | Pro | Glu | Leu | Leu | |
| | | | 275 | | | | | 280 | | | | | 285 | | |
| Arg | Glu | Leu | Gln | Arg | Leu | His | Val | Thr | His | Thr | Val | Arg | Lys | Leu | His |
| | 290 | | | | | 295 | | | | | 300 | | | | |
| Val | Gly | Asp | Phe | Val | Trp | Val | Ala | Gln | Glu | Thr | Asn | Pro | Arg | Asp | Pro |
| 305 | | | | | 310 | | | | | 315 | | | | | 320 |
| Ala | Asn | Pro | Gly | Glu | Leu | Val | Leu | Asp | His | Ile | Val | Glu | Arg | Lys | Arg |
| | | | | 325 | | | | | 330 | | | | | 335 | |
| Leu | Asp | Asp | Leu | Cys | Ser | Ser | Ile | Ile | Asp | Gly | Arg | Phe | Arg | Glu | Gln |
| | | | 340 | | | | | 345 | | | | | 350 | | |
| Lys | Phe | Arg | Leu | Lys | Arg | Cys | Gly | Leu | Glu | Arg | Arg | Val | Tyr | Leu | Val |
| | | 355 | | | | | 360 | | | | | 365 | | | |
| Glu | Glu | His | Gly | Ser | Val | His | Asn | Leu | Ser | Leu | Pro | Glu | Ser | Thr | Leu |
| | 370 | | | | | 375 | | | | | 380 | | | | |
| Leu | Gln | Ala | Val | Thr | Asn | Thr | Gln | Val | Ile | Asp | Gly | Phe | Phe | Val | Lys |
| 385 | | | | | 390 | | | | | 395 | | | | | 400 |
| Arg | Thr | Ala | Asp | Ile | Lys | Glu | Ser | Ala | Ala | Tyr | Leu | Ala | Leu | Leu | Thr |
| | | | | 405 | | | | | 410 | | | | | 415 | |
| Arg | Gly | Leu | Gln | Arg | Leu | Tyr | Gln | Gly | His | Thr | Leu | Arg | Ser | Arg | Pro |
| | | | 420 | | | | | 425 | | | | | 430 | | |
| Trp | Gly | Thr | Pro | Gly | Asn | Pro | Glu | Ser | Gly | Ala | Met | Thr | Ser | Pro | Asn |
| | | | 435 | | | | | 440 | | | | | 445 | | |
| Pro | Leu | Cys | Ser | Leu | Leu | Thr | Phe | Ser | Asp | Phe | Asn | Ala | Gly | Ala | Ile |
| | 450 | | | | | 455 | | | | | 460 | | | | |
| Lys | Asn | Lys | Ala | Gln | Ser | Val | Arg | Glu | Val | Phe | Ala | Arg | Gln | Leu | Met |
| 465 | | | | | 470 | | | | | 475 | | | | | 480 |
| Gln | Val | Arg | Gly | Val | Ser | Gly | Glu | Lys | Ala | Ala | Leu | Val | Asp | Arg | |
| | | | | 485 | | | | | 490 | | | | | 495 | |
| Tyr | Ser | Thr | Pro | Ala | Ser | Leu | Leu | Ala | Ala | Tyr | Asp | Ala | Cys | Ala | Thr |
| | | | 500 | | | | | 505 | | | | | 510 | | |
| Pro | Lys | Glu | Gln | Glu | Thr | Leu | Leu | Ser | Thr | Ile | Lys | Cys | Gly | Arg | Leu |
| | | 515 | | | | | 520 | | | | | 525 | | | |
| Gln | Arg | Asn | Leu | Gly | Pro | Ala | Leu | Ser | Arg | Thr | Leu | Ser | Gln | Leu | Tyr |
| | 530 | | | | | 535 | | | | | 540 | | | | |
| Cys | Ser | Tyr | Gly | Pro | Leu | Thr | | | | | | | | | |
| 545 | | | | | 550 | | | | | | | | | | |

<210> SEQ ID NO 3
<211> LENGTH: 2462
<212> TYPE: DNA
<213> ORGANISM: Homo sapiens
<220> FEATURE:
<221> NAME/KEY: CDS
<222> LOCATION: (185)..(1549)
<223> OTHER INFORMATION: Human Mus81(2)

<400> SEQUENCE: 3

```
gcggccgcag gctctcttct cgttagtgcc ccctgtgttt ggggccccgt gatctcaacg    60
gtcctgccct cggtctccct cttccccgc ccgccctgg gccaggtgtt cgaatcccga    120
```

```
ctccagaact ggcggcgtcc cagtcccgcg ggcgtggagc gccggaggac ccgccctcgg    180 gctc atg gcg gcc ccg gtc cgc ctg ggc cgg aag cgc ccg ctg cct gcc    229
     Met Ala Ala Pro Val Arg Leu Gly Arg Lys Arg Pro Leu Pro Ala
     1               5                   10                  15 tgt ccc aac ccg ctc ttc gtt cgc tgg ctg acc gag tgg cgg gac gag    277
Cys Pro Asn Pro Leu Phe Val Arg Trp Leu Thr Glu Trp Arg Asp Glu
                20                  25                  30 gcg acc cgc agc agg cac cgc acg cgc ttc gta ttt cag aag gcg ctg    325
Ala Thr Arg Ser Arg His Arg Thr Arg Phe Val Phe Gln Lys Ala Leu
                    35                  40                  45 cgt tcc ctc cga cgg tac cca ctg ccg ctg cgc agc ggg aag gaa gct    373
Arg Ser Leu Arg Arg Tyr Pro Leu Pro Leu Arg Ser Gly Lys Glu Ala
                50                  55                  60 aag atc cta cag cac ttc gga gac ggg ctc tgc cgg atg ctg gac gag    421
Lys Ile Leu Gln His Phe Gly Asp Gly Leu Cys Arg Met Leu Asp Glu
65                  70                  75 cgg ctg cag cgg cac cga aca tcg ggc ggt gac cat gcc ccg gac tca    469
Arg Leu Gln Arg His Arg Thr Ser Gly Gly Asp His Ala Pro Asp Ser
80                  85                  90                  95 cca tct gga gag aac agt cca gcc ccg cag ggg cga ctt gcg gaa gtc    517
Pro Ser Gly Glu Asn Ser Pro Ala Pro Gln Gly Arg Leu Ala Glu Val
                    100                 105                 110 cag gac tct tcc atg cca gtt cct gcc cag ccc aaa gcg gga ggc tct    565
Gln Asp Ser Ser Met Pro Val Pro Ala Gln Pro Lys Ala Gly Gly Ser
                115                 120                 125 ggc agc tac tgg cca gct cgg cac tca gga gcc cga gtg ata ctg ctg    613
Gly Ser Tyr Trp Pro Ala Arg His Ser Gly Ala Arg Val Ile Leu Leu
            130                 135                 140 gtg ctc tac cgg gag cac ctg aat cct aat ggt cac cac ttc tta acc    661
Val Leu Tyr Arg Glu His Leu Asn Pro Asn Gly His His Phe Leu Thr
145                 150                 155 aag gag gag ctg ctg cag agg tgt gct cag aag tcc ccc agg gta gcc    709
Lys Glu Glu Leu Leu Gln Arg Cys Ala Gln Lys Ser Pro Arg Val Ala
160                 165                 170                 175 cct ggg agt gcc cca ccc tgg cca gcc ctc cgc tcc ctc ctt cac agg    757
Pro Gly Ser Ala Pro Pro Trp Pro Ala Leu Arg Ser Leu Leu His Arg
            180                 185                 190 aac ctg gtc ctc agg aca cac cag cca gcc agg tac tca ttg acc cca    805
Asn Leu Val Leu Arg Thr His Gln Pro Ala Arg Tyr Ser Leu Thr Pro
                195                 200                 205 gag ggc ctg gag ctg gcc cag aag ttg gcc gag tca gaa ggc ctg agc    853
Glu Gly Leu Glu Leu Ala Gln Lys Leu Ala Glu Ser Glu Gly Leu Ser
            210                 215                 220 ttg ctg aat gtg ggc atc ggg ccc aag gag ccc cct ggg gag gag aca    901
Leu Leu Asn Val Gly Ile Gly Pro Lys Glu Pro Pro Gly Glu Glu Thr
225                 230                 235 gca gtg cca gga gca gct tca gca gag ctt gcc agt gaa gca ggg gtc    949
Ala Val Pro Gly Ala Ala Ser Ala Glu Leu Ala Ser Glu Ala Gly Val
240                 245                 250                 255 cag cag cag cca ctg gag ctg agg cct gga gag tac agg gtg ctg ttg    997
Gln Gln Gln Pro Leu Glu Leu Arg Pro Gly Glu Tyr Arg Val Leu Leu
                260                 265                 270 tgt gtg gac att ggc gag acc cgg ggg ggc ggg cac agg ccg gag ctg   1045
Cys Val Asp Ile Gly Glu Thr Arg Gly Gly Gly His Arg Pro Glu Leu
            275                 280                 285 ctc cga gag cta cag cgg ctg cac gtg acc cac acg gtg cgc aag ctg   1093
Leu Arg Glu Leu Gln Arg Leu His Val Thr His Thr Val Arg Lys Leu
                290                 295                 300
```

```
cac gtt gga gat ttt gtg tgg gtg gct cag gag acc aat cct aga gac    1141
His Val Gly Asp Phe Val Trp Val Ala Gln Glu Thr Asn Pro Arg Asp
    305                 310                 315 cca gca aac cct ggg gag ttg gta ctg gat cac att gtg gag cgc aag    1189
Pro Ala Asn Pro Gly Glu Leu Val Leu Asp His Ile Val Glu Arg Lys
320                 325                 330                 335 cga ctg gat gac ctt tgc agc agc atc atc gac ggc cgc ttc cgg gag    1237
Arg Leu Asp Asp Leu Cys Ser Ser Ile Ile Asp Gly Arg Phe Arg Glu
                340                 345                 350 cag aag ttc cga ctg aag cgc tgt ggt ctg gag cgc cgg gta tac ctg    1285
Gln Lys Phe Arg Leu Lys Arg Cys Gly Leu Glu Arg Arg Val Tyr Leu
            355                 360                 365 gtg gaa gag cat ggt tcc gtc cac aac ctc agc ttt ctt gag agc aca    1333
Val Glu Glu His Gly Ser Val His Asn Leu Ser Phe Leu Glu Ser Thr
        370                 375                 380 ctt gtg cag gct gtc acc aac act cag gtc att gat ggc ttt ttt gtg    1381
Leu Val Gln Ala Val Thr Asn Thr Gln Val Ile Asp Gly Phe Phe Val
    385                 390                 395 aag cgc aca gca gac att aag gag tca gcc gcc tac ctg gcc ctc ttg    1429
Lys Arg Thr Ala Asp Ile Lys Glu Ser Ala Ala Tyr Leu Ala Leu Leu
400                 405                 410                 415 act cgg ggc ctg cag aga ctc tac cag gtg agc aga ggc ccc ttt ccc    1477
Thr Arg Gly Leu Gln Arg Leu Tyr Gln Val Ser Arg Gly Pro Phe Pro
                420                 425                 430 agt gtc ggg aca gag ccc aca agg aat tca cct tgc ctg ggc cct gtg    1525
Ser Val Gly Thr Glu Pro Thr Arg Asn Ser Pro Cys Leu Gly Pro Val
            435                 440                 445 cat ccc caa aag aag caa ggt ggg tgagatcccc atttctcagg ctggccccc    1579
His Pro Gln Lys Lys Gln Gly Gly
        450                 455 aaggctgagg actgggcagg ggctggctgg agttgttcct tcgagctcca gcctggcctc    1639
agtcccttct tccctcaggg ccacaccta cgcagccgcc cctggggaac ccctgggaac    1699
cctgaatcag gggccatgac ctctccaaac cctctctgct cactcctcac cttcagtgac    1759
ttcaacgcag gagccatcaa gaataaggcc cagtcggtgc gagaagtgtt tgcccggcag    1819
ctgatgcagg tgcgcggagt gagtggggag aaggcagcag ccctggtgga tcgatacagc    1879 accctgcca gcctcctggc cgcctatgat gcctgtgcca ccccaagga caagagaca    1939 ctgctgagca ccattaagtg tgggcgtcta cagaggaatc tggggcctgc tctgagcagg    1999
accttatccc agctctactg cagctacggc cccttgacct gagcttatgc cgtgaaacag    2059
cccccagccc ccgtctgtcc cccaaccag gctagccagc ctttaacaa catcttttgg    2119 ggtacaatta gaatctaagt gtttgcagcc atatgtgtca tgtagaagat gcctagccct    2179
ggggaccttg tgaaatacgc aggaaccagg gataccatct ggtccagtgg tttttaaaca    2239
aagctgctta gcacctggaa ttccctggtc agggagatgg agtcagtggg gcattgcagc    2299
ttggaatcta ttttatgtca ccagttggtc ctcatcaaat aaaatttcct taggagtgca    2359
gagggctcat tggaaaaata aaataataa aaataaataa aacttcctaa aagaaaagat    2419
tgaaaaccaa aaaaaaaaaa aaaaaaaacc tcgtgccgaa ttc                     2462

<210> SEQ ID NO 4
<211> LENGTH: 455
<212> TYPE: PRT
<213> ORGANISM: Homo sapiens
```

<400> SEQUENCE: 4

```
Met Ala Ala Pro Val Arg Leu Gly Arg Lys Arg Pro Leu Pro Ala Cys
 1               5                  10                  15

Pro Asn Pro Leu Phe Val Arg Trp Leu Thr Glu Trp Arg Asp Glu Ala
                20                  25                  30

Thr Arg Ser Arg His Arg Thr Arg Phe Val Phe Gln Lys Ala Leu Arg
            35                  40                  45

Ser Leu Arg Arg Tyr Pro Leu Pro Leu Arg Ser Gly Lys Glu Ala Lys
        50                  55                  60

Ile Leu Gln His Phe Gly Asp Gly Leu Cys Arg Met Leu Asp Glu Arg
 65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Pro Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Gly Leu Ser Leu
    210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly His Arg Pro Glu Leu Leu
        275                 280                 285

Arg Glu Leu Gln Arg Leu His Val Thr His Thr Val Arg Lys Leu His
    290                 295                 300

Val Gly Asp Phe Val Trp Val Ala Gln Glu Thr Asn Pro Arg Asp Pro
305                 310                 315                 320

Ala Asn Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Glu Arg Val Tyr Leu Val
        355                 360                 365

Glu Glu His Gly Ser Val His Asn Leu Ser Phe Leu Glu Ser Thr Leu
    370                 375                 380

Val Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
                405                 410                 415
```

```
Arg Gly Leu Gln Arg Leu Tyr Gln Val Ser Arg Gly Pro Phe Pro Ser
            420                 425                 430

Val Gly Thr Glu Pro Thr Arg Asn Ser Pro Cys Leu Gly Pro Val His
        435                 440                 445

Pro Gln Lys Lys Gln Gly Gly
    450                 455

<210> SEQ ID NO 5
<211> LENGTH: 632
<212> TYPE: PRT
<213> ORGANISM: Saccharomyces cerevisiae
<220> FEATURE:
<223> OTHER INFORMATION: S. Cerevisiae mus81

<400> SEQUENCE: 5

Met Glu Leu Ser Ser Asn Leu Lys Asp Leu Tyr Ile Glu Trp Leu Gln
  1               5                  10                  15

Glu Leu Val Asp Gly Leu Thr Pro Lys Gln Glu Gln Leu Lys Ile Ala
             20                  25                  30

Tyr Glu Lys Ala Lys Arg Asn Leu Gln Asn Ala Glu Gly Ser Phe Tyr
         35                  40                  45

Tyr Pro Thr Asp Leu Lys Lys Val Lys Gly Ile Gly Asn Thr Ile Ile
     50                  55                  60

Lys Arg Leu Asp Thr Lys Leu Arg Asn Tyr Cys Lys Ile His His Ile
 65                  70                  75                  80

Ser Pro Val Glu Ala Pro Ser Leu Thr Gln Thr Ser Ser Thr Arg Pro
                 85                  90                  95

Pro Lys Arg Thr Thr Thr Ala Leu Arg Ser Ile Val Asn Ser Cys Glu
            100                 105                 110

Asn Asp Lys Asn Glu Ala Pro Glu Glu Lys Gly Thr Lys Lys Arg Lys
        115                 120                 125

Thr Arg Lys Tyr Ile Pro Lys Lys Arg Ser Gly Gly Tyr Ala Ile Leu
    130                 135                 140

Leu Ser Leu Leu Glu Leu Asn Ala Ile Pro Arg Gly Val Ser Lys Glu
145                 150                 155                 160

Gln Ile Ile Glu Val Ala Gly Lys Tyr Ser Asp His Cys Met Thr Pro
                165                 170                 175

Asn Phe Ser Thr Lys Glu Phe Tyr Gly Ala Trp Ser Ser Ile Ala Ala
            180                 185                 190

Leu Lys Lys His Ser Leu Val Leu Glu Glu Gly Arg Pro Lys Arg Tyr
        195                 200                 205

Ser Leu Thr Glu Glu Gly Val Glu Leu Thr Lys Ser Leu Lys Thr Ala
    210                 215                 220

Asp Gly Ile Ser Phe Pro Lys Glu Asn Glu Glu Pro Asn Glu Tyr Ser
225                 230                 235                 240

Val Thr Arg Asn Glu Ser Ser Glu Phe Thr Ala Asn Leu Thr Asp Leu
                245                 250                 255

Arg Gly Glu Tyr Gly Lys Glu Glu Pro Cys Asp Ile Asn Asn Thr
            260                 265                 270

Ser Phe Met Leu Asp Ile Thr Phe Gln Asp Leu Ser Thr Pro Gln Arg
        275                 280                 285

Leu Gln Asn Asn Val Phe Lys Asn Asp Arg Leu Asn Ser Gln Thr Asn
    290                 295                 300

Ile Ser Ser His Lys Leu Glu Glu Val Ser Asp Asp Gln Thr Val Pro
305                 310                 315                 320
```

-continued

```
Asp Ser Ala Leu Lys Ala Lys Ser Thr Ile Lys Arg Arg Arg Tyr Asn
            325                 330                 335

Gly Val Ser Tyr Glu Leu Trp Cys Ser Gly Asp Phe Glu Val Phe Pro
            340                 345                 350

Ile Ile Asp His Arg Glu Ile Lys Ser Gln Ser Asp Arg Glu Phe Phe
            355                 360                 365

Ser Arg Ala Phe Glu Arg Lys Gly Met Lys Ser Glu Ile Arg Gln Leu
370                 375                 380

Ala Leu Gly Asp Ile Ile Trp Val Ala Lys Asn Lys Asn Thr Gly Leu
385                 390                 395                 400

Gln Cys Val Leu Asn Thr Ile Val Glu Arg Lys Arg Leu Asp Asp Leu
            405                 410                 415

Ala Leu Ser Ile Arg Asp Asn Arg Phe Met Glu Gln Lys Asn Arg Leu
            420                 425                 430

Glu Lys Ser Gly Cys Glu His Lys Tyr Tyr Leu Ile Glu Glu Thr Met
            435                 440                 445

Ser Gly Asn Ile Gly Asn Met Asn Glu Ala Leu Lys Thr Ala Leu Trp
450                 455                 460

Val Ile Leu Val Tyr Tyr Lys Phe Ser Met Ile Arg Thr Cys Asn Ser
465                 470                 475                 480

Asp Glu Thr Val Glu Lys Ile His Ala Leu His Thr Val Ile Ser His
            485                 490                 495

His Tyr Ser Gln Lys Asp Leu Ile Val Ile Phe Pro Ser Asp Leu Lys
            500                 505                 510

Ser Lys Asp Asp Tyr Lys Lys Val Leu Leu Gln Phe Arg Arg Glu Phe
            515                 520                 525

Glu Arg Lys Gly Gly Ile Glu Cys Cys His Asn Leu Glu Cys Phe Gln
530                 535                 540

Glu Leu Met Gly Lys Gly Asp Leu Lys Thr Val Gly Glu Leu Thr Ile
545                 550                 555                 560

His Val Leu Met Leu Val Lys Gly Ile Ser Leu Glu Lys Ala Val Ala
            565                 570                 575

Ile Gln Glu Ile Phe Pro Thr Leu Asn Lys Ile Leu Met Ala Tyr Lys
            580                 585                 590

Thr Cys Ser Ser Glu Glu Glu Ala Lys Leu Leu Met Phe Asn Val Leu
            595                 600                 605

Gly Asp Ala Pro Gly Ala Lys Lys Ile Thr Lys Ser Leu Ser Glu Lys
            610                 615                 620

Ile Tyr Asp Ala Phe Gly Lys Leu
625                 630

<210> SEQ ID NO 6
<211> LENGTH: 572
<212> TYPE: PRT
<213> ORGANISM: Schizosaccharomyces pombe
<220> FEATURE:
<223> OTHER INFORMATION: S. pombe mus81

<400> SEQUENCE: 6

Met Lys Ser Cys Pro Ile Thr Phe His Arg Pro Ser Gln Ala Leu Ala
1               5                   10                  15

Leu Lys Gly Ile Gly Pro Thr Ile Cys Ala Lys Leu Glu Lys Lys Trp
            20                  25                  30

Asn Ala Tyr Cys Leu Glu Asn Asn Ile Pro Ile Ser Thr His Asn Glu
        35                  40                  45
```

-continued

```
Gln Asn Asp Ser His Val Asn Ala Asn Lys Ser Ser Glu Thr Ser
     50                  55                  60
Ser Glu Lys Pro Arg Ser Val Lys Lys Pro Thr Thr Arg Lys Arg Lys
 65                  70                  75                  80
Val Tyr Val Pro Ser Tyr Arg Ser Gly Ala Tyr Ser Ile Leu Cys Ala
                 85                  90                  95
Leu Tyr Met Leu Asn Lys His Glu Phe Ala Thr Lys Pro Gln Ile Val
             100                 105                 110
Thr Met Ala Gln Pro Tyr Cys Asp Ser Ser Phe Gly Ser Ala Thr Asp
             115                 120                 125
Arg Asn Met Arg Tyr Thr Ala Trp Ser Ala Met Lys Thr Leu Ile Thr
         130                 135                 140
Lys Asn Leu Val Tyr Gln Thr Gly His Pro Ser Lys Tyr Cys Leu Thr
145                 150                 155                 160
Asp Asp Gly Glu Glu Val Cys Ile Arg Leu Ala Lys Val Asp Asp Ser
                 165                 170                 175
Phe Gln Arg Lys His Thr Val Ser Asn Phe Ser Val Ser Lys Ser Asp
             180                 185                 190
Asp His Asp Ser Ser Leu Cys Gln Pro Pro Asn Phe Val Thr Ser Ile
         195                 200                 205
Asn Lys Ala Gly Ser Ser Ser Asp His Gly Gly Glu Leu His Val Thr
     210                 215                 220
Tyr Cys Pro Val Asp His Asn Glu Val Ser Asp Gly Val Glu Thr Asp
225                 230                 235                 240
Ile Asp Val Asp Gln Val Asp Ser Leu Thr Gly Ile His Asp His His
                 245                 250                 255
Ile Ile Asn Asn Glu Gln Leu Ile Asp Leu Thr Glu Gln Glu Lys Lys
             260                 265                 270
Gln Pro Asn Glu Ser Asn Leu Ser Asn Leu Lys Ile Glu Thr Val Leu
         275                 280                 285
Phe Ser Asn Cys Thr Val Phe Leu Leu Ile Asp Thr Arg Glu Ile Arg
     290                 295                 300
Ser Pro Leu Asp Arg Asn Leu Ile Ile Asp Lys Leu Thr Asn Asp Phe
305                 310                 315                 320
Gly Val Asn Cys Gln Val Arg Ser Leu Glu Leu Gly Asp Ala Leu Trp
                 325                 330                 335
Val Ala Arg Asp Met Glu Ser Gly Gln Glu Val Val Leu Asp Phe Val
             340                 345                 350
Val Glu Arg Lys Arg Tyr Asp Asp Leu Val Ala Ser Ile Lys Asp Gly
         355                 360                 365
Arg Phe His Glu Gln Lys Ala Arg Leu Lys Lys Ser Gly Ile Arg Ser
     370                 375                 380
Val Thr Tyr Ile Leu Glu Glu Ser Ser Tyr Asp Glu Ser Phe Thr Glu
385                 390                 395                 400
Ser Ile Arg Thr Ala Val Ser Asn Thr Gln Val Asp Gln Leu Phe His
                 405                 410                 415
Val Arg His Thr Arg Ser Leu Glu His Ser Val Ser Leu Leu Ala Glu
             420                 425                 430
Met Thr Lys Gln Ile Asn Leu Phe Tyr Glu Lys Arg Lys Thr Leu Ala
         435                 440                 445
Val Ile Pro Asp Leu Ser Ile Glu Ala Lys Thr Tyr Glu Ser Leu Arg
     450                 455                 460
```

```
Glu Gln Leu Leu Lys Ile Asp Pro Ser Thr Pro Tyr His Ile Ser Tyr
465                 470                 475                 480

His Ala Phe Ser Ser Val Leu Ser Lys Ser Ser Thr Leu Thr Val Gly
            485                 490                 495

Asp Ile Phe Ile Arg Met Leu Met Thr Ile Lys Gly Ile Ser Ala Ser
                500                 505                 510

Lys Ala Ile Glu Ile Gln Lys Lys Tyr Pro Thr Phe Met His Leu Phe
            515                 520                 525

Glu Ala Tyr Glu Lys Ser Ser Ser Gln Glu Arg Asn Leu Leu Leu
530                 535                 540

Asn Lys Thr Cys Gln Gly Tyr Gly Phe Gln Thr Ile Gly Pro Ala Leu
545                 550                 555                 560

Ser Ala Lys Val Ala Ser Val Phe Phe Pro Glu Ser
                565                 570

<210> SEQ ID NO 7
<211> LENGTH: 1598
<212> TYPE: DNA
<213> ORGANISM: Homo sapiens
<220> FEATURE:
<221> NAME/KEY: CDS
<222> LOCATION: (26)..(1297)
<223> OTHER INFORMATION: Human Mus81(3)

<400> SEQUENCE: 7
gatatctgca gaattcgccc ttgac atg gcg gcc ccg gtc cgc ctg ggc cgg      52
                            Met Ala Ala Pro Val Arg Leu Gly Arg
                             1               5 aag cgc ccg ctg cct gcc tgt ccc aac ccg ctc ttc gtt cgc tgg ctg     100
Lys Arg Pro Leu Pro Ala Cys Pro Asn Pro Leu Phe Val Arg Trp Leu
 10                  15                  20                  25 acc gag tgg cgg gac gag gcg acc cgc agc agg cgc cgc acg cgc ttc     148
Thr Glu Trp Arg Asp Glu Ala Thr Arg Ser Arg Arg Arg Thr Arg Phe
                 30                  35                  40 gta ttt cag aag gcg ctg cgt tcc ctc cga cgg tac cca ctg ccg ctg     196
Val Phe Gln Lys Ala Leu Arg Ser Leu Arg Arg Tyr Pro Leu Pro Leu
             45                  50                  55 cgc agc ggg aag gaa gct aag atc cta cag cac ttc gga gac ggg ctc     244
Arg Ser Gly Lys Glu Ala Lys Ile Leu Gln His Phe Gly Asp Gly Leu
         60                  65                  70 tgc cgg atg ctg gac gag cgg ctg cag cgg cac cga aca tcg ggc ggt     292
Cys Arg Met Leu Asp Glu Arg Leu Gln Arg His Arg Thr Ser Gly Gly
 75                  80                  85 gac cat gcc ccg gac tca cca tct gga gag aac agt cca gcc ccg cag     340
Asp His Ala Pro Asp Ser Pro Ser Gly Glu Asn Ser Pro Ala Pro Gln
 90                  95                 100                 105 ggg cga ctt gcg gaa gtc cag gac tct tcc atg cca gtt cct gcc cag     388
Gly Arg Leu Ala Glu Val Gln Asp Ser Ser Met Pro Val Pro Ala Gln
                110                 115                 120 ccc aaa gcg gga ggc tct ggc agc tac tgg cca gct cgg cac tca gga     436
Pro Lys Ala Gly Gly Ser Gly Ser Tyr Trp Pro Ala Arg His Ser Gly
            125                 130                 135 gcc cga gtg ata ctg ctg gtg ctc tac cgg gag cac ctg aat cct aat     484
Ala Arg Val Ile Leu Leu Val Leu Tyr Arg Glu His Leu Asn Pro Asn
        140                 145                 150 ggt cac cac ttc tta acc aag gag gag ctg ctg cag agg tgt gct cag     532
Gly His His Phe Leu Thr Lys Glu Glu Leu Leu Gln Arg Cys Ala Gln
    155                 160                 165
```

| | |
|---|---|
| aag tcc ccc agg gta gcc cct ggg agt gct cga ccc tgg cca gcc ctc<br>Lys Ser Pro Arg Val Ala Pro Gly Ser Ala Arg Pro Trp Pro Ala Leu<br>170                         175                     180                    185 | 580 |
| cgc tcc ctc ctt cac agg aac ctg gtc ctc agg aca cac cag cca gcc<br>Arg Ser Leu Leu His Arg Asn Leu Val Leu Arg Thr His Gln Pro Ala<br>                     190                     195                     200 | 628 |
| agg tac tca ttg acc cca gag ggc ctg gag ctg gcc cag aag ttg gcc<br>Arg Tyr Ser Leu Thr Pro Glu Gly Leu Glu Leu Ala Gln Lys Leu Ala<br>               205                     210                     215 | 676 |
| gag tca gaa ggc ctg agc ttg ctg aat gtg ggc atc ggg ccc aag gag<br>Glu Ser Glu Gly Leu Ser Leu Leu Asn Val Gly Ile Gly Pro Lys Glu<br>    220                     225                     230 | 724 |
| ccc cct ggg gag gag aca gca gtg cca gga gca gct tca gca gag ctt<br>Pro Pro Gly Glu Glu Thr Ala Val Pro Gly Ala Ala Ser Ala Glu Leu<br>235                         240                     245 | 772 |
| gcc agt gaa gca ggg gtc cag cag cag cca ctg gag ctg agg cct gga<br>Ala Ser Glu Ala Gly Val Gln Gln Gln Pro Leu Glu Leu Arg Pro Gly<br>250                         255                     260                     265 | 820 |
| gag tac agg gtg ctg ttg tgt gtg gac att ggc gag acc cgg ggg ggc<br>Glu Tyr Arg Val Leu Leu Cys Val Asp Ile Gly Glu Thr Arg Gly Gly<br>                     270                     275                     280 | 868 |
| ggg cac agg ccg gag ctg ctc cga gag cta cag cgg ctg cac gtg acc<br>Gly His Arg Pro Glu Leu Leu Arg Glu Leu Gln Arg Leu His Val Thr<br>               285                     290                     295 | 916 |
| cac acg gtg cgc aag ctg cac gtt gga gat ttt gtg tgg gtg gcc cag<br>His Thr Val Arg Lys Leu His Val Gly Asp Phe Val Trp Val Ala Gln<br>    300                     305                     310 | 964 |
| gag acc aat cct aga gac cca gca aac cct ggg gag ttg gta ctg gat<br>Glu Thr Asn Pro Arg Asp Pro Ala Asn Pro Gly Glu Leu Val Leu Asp<br>315                         320                     325 | 1012 |
| cac att gtg gag cgc aag cga ctg gat gac ctt tgc agc agc atc atc<br>His Ile Val Glu Arg Lys Arg Leu Asp Asp Leu Cys Ser Ser Ile Ile<br>330                         335                     340                     345 | 1060 |
| gac ggc cgc ttc cgg gag cag aag ttc cgg ctg aag cgc tgt ggt ctg<br>Asp Gly Arg Phe Arg Glu Gln Lys Phe Arg Leu Lys Arg Cys Gly Leu<br>                     350                     355                     360 | 1108 |
| gag cgc cgg gta tac ctg gtg gaa gag cat ggt tcc gtc cac aac ctc<br>Glu Arg Arg Val Tyr Leu Val Glu Glu His Gly Ser Val His Asn Leu<br>               365                     370                     375 | 1156 |
| agc ctt cct gag agc aca ctg ctg cag gct gtc acc aac act cag gtc<br>Ser Leu Pro Glu Ser Thr Leu Leu Gln Ala Val Thr Asn Thr Gln Val<br>    380                     385                     390 | 1204 |
| att gat ggc ttt ttt gtg aag cgc aca gca gac att aag gag tca gcc<br>Ile Asp Gly Phe Phe Val Lys Arg Thr Ala Asp Ile Lys Glu Ser Ala<br>395                         400                     405 | 1252 |
| gcc tac ctg gcc ctc ttg acg cgg ggc ctg cag aga ctc tac cag<br>Ala Tyr Leu Ala Leu Leu Thr Arg Gly Leu Gln Arg Leu Tyr Gln<br>410                         415                     420 | 1297 |
| tgacttcaac gcaggagcca tcaagaataa ggcccagtcg gtgcgagaag tgtttgcccg | 1357 |
| gcagctgatg caggtgcgcg gagtgagtgg ggagaaggca gcagccctgg tggatcgata | 1417 |
| cagcacccct gccagcctcc tggccgccta tgatgcctgt gccaccccca aggaacaaga | 1477 |
| gacactgctg agcaccatta agtgtgggcg tctacagagg aatctggggc ctgctctgag | 1537 |
| caggaccttg tcccagctct actgcagcta cggcccttg acctgagtca agggcgaatt | 1597 |
| c | 1598 |

<210> SEQ ID NO 8
<211> LENGTH: 424
<212> TYPE: PRT
<213> ORGANISM: Homo sapiens

<400> SEQUENCE: 8

```
Met Ala Ala Pro Val Arg Leu Gly Arg Lys Arg Pro Leu Pro Ala Cys
  1               5                  10                  15

Pro Asn Pro Leu Phe Val Arg Trp Leu Thr Glu Trp Arg Asp Glu Ala
             20                  25                  30

Thr Arg Ser Arg Arg Thr Arg Phe Val Phe Gln Lys Ala Leu Arg
         35                  40                  45

Ser Leu Arg Arg Tyr Pro Leu Pro Leu Arg Ser Gly Lys Glu Ala Lys
     50                  55                  60

Ile Leu Gln His Phe Gly Asp Gly Leu Cys Arg Met Leu Asp Glu Arg
 65                  70                  75                  80

Leu Gln Arg His Arg Thr Ser Gly Gly Asp His Ala Pro Asp Ser Pro
                 85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Arg Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Glu Gly Leu Ser Leu
    210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly Gly His Arg Pro Glu Leu Leu
        275                 280                 285

Arg Glu Leu Gln Arg Leu His Val Thr His Thr Val Arg Lys Leu His
    290                 295                 300

Val Gly Asp Phe Val Trp Val Ala Gln Glu Thr Asn Pro Arg Asp Pro
305                 310                 315                 320

Ala Asn Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Glu Arg Val Tyr Leu Val
    355                 360                 365

Glu Glu His Gly Ser Val His Asn Leu Ser Leu Pro Glu Ser Thr Leu
    370                 375                 380
```

-continued

```
Leu Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
            405                 410                 415

Arg Gly Leu Gln Arg Leu Tyr Gln
            420

<210> SEQ ID NO 9
<211> LENGTH: 1699
<212> TYPE: DNA
<213> ORGANISM: Homo sapiens
<220> FEATURE:
<221> NAME/KEY: CDS
<222> LOCATION: (26)..(1681)
<223> OTHER INFORMATION: Human Mus81(4)

<400> SEQUENCE: 9
gatatctgca gaattcgccc ttgac atg gcg gcc ccg gtc cgc ctg ggc cgg         52
                              Met Ala Ala Pro Val Arg Leu Gly Arg
                               1               5 aag cgc ccg ctg cct gcc tgt ccc aac ccg ctc ttc gtt cgc tgg ctg        100
Lys Arg Pro Leu Pro Ala Cys Pro Asn Pro Leu Phe Val Arg Trp Leu
 10                  15                  20                  25 acc gag tgg cgg gac gag gcg acc cgc agc agg cgc acg cgc ttc            148
Thr Glu Trp Arg Asp Glu Ala Thr Arg Ser Arg Arg Thr Arg Phe
                 30                  35                  40 gta ttt cag aag gcg ctg cgt tcc ctc cga cgg tac cca ctg ccg ctg        196
Val Phe Gln Lys Ala Leu Arg Ser Leu Arg Arg Tyr Pro Leu Pro Leu
                 45                  50                  55 cgc agc ggg aag gaa gct aag atc cta cag cac ttc gga gac ggg ctc        244
Arg Ser Gly Lys Glu Ala Lys Ile Leu Gln His Phe Gly Asp Gly Leu
             60                  65                  70 tgc cgg atg ctg gac gag cgg ctg cag cgg cac cga aca tcg ggc ggt        292
Cys Arg Met Leu Asp Glu Arg Leu Gln Arg His Arg Thr Ser Gly Gly
         75                  80                  85 gac cat gcc ccg gac tca cca tct gga gag aac agt cca gcc ccg cag        340
Asp His Ala Pro Asp Ser Pro Ser Gly Glu Asn Ser Pro Ala Pro Gln
 90                  95                 100                 105 ggg cga ctt gcg gaa gtc cag gac tct tcc atg cca gtt cct gcc cag        388
Gly Arg Leu Ala Glu Val Gln Asp Ser Ser Met Pro Val Pro Ala Gln
                110                 115                 120 ccc aaa gcg gga ggc tct ggc agc tac tgg cca gct cgg cac tca gga        436
Pro Lys Ala Gly Gly Ser Gly Ser Tyr Trp Pro Ala Arg His Ser Gly
                125                 130                 135 gcc cga gtg ata ctg ctg gtg ctc tac cgg gag cac ctg aat cct aat        484
Ala Arg Val Ile Leu Leu Val Leu Tyr Arg Glu His Leu Asn Pro Asn
            140                 145                 150 ggt cac cac ttc tta acc aag gag gag ctg ctg cag agg tgt gct cag        532
Gly His His Phe Leu Thr Lys Glu Glu Leu Leu Gln Arg Cys Ala Gln
        155                 160                 165 aag tcc ccc agg gta gcc cct ggg agt gct cga ccc tgg cca gcc ctc        580
Lys Ser Pro Arg Val Ala Pro Gly Ser Ala Arg Pro Trp Pro Ala Leu
170                 175                 180                 185 cgc tcc ctc ctt cac agg aac ctg gtc ctc agg aca cac cag cca gcc        628
Arg Ser Leu Leu His Arg Asn Leu Val Leu Arg Thr His Gln Pro Ala
                190                 195                 200 agg tac tca ttg acc cca gag ggc ctg gag ctg gcc cag aag ttg gcc        676
Arg Tyr Ser Leu Thr Pro Glu Gly Leu Glu Leu Ala Gln Lys Leu Ala
                205                 210                 215
```

-continued

| | | |
|---|---|---|
| gag tca gaa ggc ctg agc ttg ctg aat gtg ggc atc ggg ccc aag gag<br>Glu Ser Glu Gly Leu Ser Leu Leu Asn Val Gly Ile Gly Pro Lys Glu<br>220                       225                     230 | | 724 |
| ccc cct ggg gag gag aca gca gtg cca gga gca gct tca gca gag ctt<br>Pro Pro Gly Glu Glu Thr Ala Val Pro Gly Ala Ala Ser Ala Glu Leu<br>235                       240                     245 | | 772 |
| gcc agt gaa gca ggg gtc cag cag cag cca ctg gag ctg agg cct gga<br>Ala Ser Glu Ala Gly Val Gln Gln Gln Pro Leu Glu Leu Arg Pro Gly<br>250                       255                     260                     265 | | 820 |
| gag tac agg gtg ctg ttg tgt gtg gac att ggc gag acc cgg ggg ggc<br>Glu Tyr Arg Val Leu Leu Cys Val Asp Ile Gly Glu Thr Arg Gly Gly<br>                     270                     275                     280 | | 868 |
| ggg cac agg ccg gag ctg ctc cga gag cta cag cgg ctg cac gtg acc<br>Gly His Arg Pro Glu Leu Leu Arg Glu Leu Gln Arg Leu His Val Thr<br>                   285                     290                     295 | | 916 |
| cac acg gtg cgc aag ctg cac gtt gga gat ttt gtg tgg gtg gcc cag<br>His Thr Val Arg Lys Leu His Val Gly Asp Phe Val Trp Val Ala Gln<br>               300                     305                     310 | | 964 |
| gag acc aat cct aga gac cca gca gca aac cct ggg gag ttg gta ctg<br>Glu Thr Asn Pro Arg Asp Pro Ala Ala Asn Pro Gly Glu Leu Val Leu<br>315                       320                     325 | | 1012 |
| gat cac att gtg gag cgc aag cga ctg gat gac ctt tgc agc agc atc<br>Asp His Ile Val Glu Arg Lys Arg Leu Asp Asp Leu Cys Ser Ser Ile<br>330                       335                     340                     345 | | 1060 |
| atc gac ggc cgc ttc cgg gag cag aag ttc cgg ctg aag cgc tgt ggt<br>Ile Asp Gly Arg Phe Arg Glu Gln Lys Phe Arg Leu Lys Arg Cys Gly<br>                     350                     355                     360 | | 1108 |
| ctg gag cgc cgg gta tac ctg gtg gaa gag cat ggt tcc gtc cac aac<br>Leu Glu Arg Arg Val Tyr Leu Val Glu Glu His Gly Ser Val His Asn<br>               365                     370                     375 | | 1156 |
| ctc agc ctt cct gag agc aca ctg ctg cag gct gtc acc aac act cag<br>Leu Ser Leu Pro Glu Ser Thr Leu Leu Gln Ala Val Thr Asn Thr Gln<br>380                       385                     390 | | 1204 |
| gtc att gat ggc ttt ttt gtg aag cgc aca gca gac att aag gag tca<br>Val Ile Asp Gly Phe Phe Val Lys Arg Thr Ala Asp Ile Lys Glu Ser<br>395                       400                     405 | | 1252 |
| gcc gcc tac ctg gcc ctc ttg acg cgg ggc ctg cag aga ctc tac cag<br>Ala Ala Tyr Leu Ala Leu Leu Thr Arg Gly Leu Gln Arg Leu Tyr Gln<br>410                       415                     420                     425 | | 1300 |
| ggc cac acc cta cgc agc cgc ccc tgg gga acc cct ggg aac cct gaa<br>Gly His Thr Leu Arg Ser Arg Pro Trp Gly Thr Pro Gly Asn Pro Glu<br>                     430                     435                     440 | | 1348 |
| tca ggg gcc atg acc tct cca aac cct ctc tgc tca ctc ctc acc ttc<br>Ser Gly Ala Met Thr Ser Pro Asn Pro Leu Cys Ser Leu Leu Thr Phe<br>               445                     450                     455 | | 1396 |
| agt gac ttc aac gca gga gcc atc aag aat aag gcc cag tcg gtg cga<br>Ser Asp Phe Asn Ala Gly Ala Ile Lys Asn Lys Ala Gln Ser Val Arg<br>               460                     465                     470 | | 1444 |
| gaa gtg ttt gcc cgg cag ctg atg cag gtg cgc gga gtg agt ggg gag<br>Glu Val Phe Ala Arg Gln Leu Met Gln Val Arg Gly Val Ser Gly Glu<br>475                       480                     485 | | 1492 |
| aag gca gca gcc ctg gtg gat cga tac agc acc cct gcc agc ctc ctg<br>Lys Ala Ala Ala Leu Val Asp Arg Tyr Ser Thr Pro Ala Ser Leu Leu<br>490                       495                     500                     505 | | 1540 |
| gcc gcc tat gat gcc tgt gcc acc ccc aag gaa caa gag aca ctg ctg<br>Ala Ala Tyr Asp Ala Cys Ala Thr Pro Lys Glu Gln Glu Thr Leu Leu<br>                     510                     515                     520 | | 1588 |
| agc acc att aag tgt ggg cgt cta cag agg aat ctg ggg cct gct ctg<br>Ser Thr Ile Lys Cys Gly Arg Leu Gln Arg Asn Leu Gly Pro Ala Leu<br>               525                     530                     535 | | 1636 |

```
agc agg acc tta tcc cag ctc tac tgc agc tac ggc ccc ttg acc        1681
Ser Arg Thr Leu Ser Gln Leu Tyr Cys Ser Tyr Gly Pro Leu Thr
    540                 545                 550 tgagtcaagg gcgaattc                                                 1699
```

<210> SEQ ID NO 10
<211> LENGTH: 552
<212> TYPE: PRT
<213> ORGANISM: Homo sapiens

<400> SEQUENCE: 10

```
Met Ala Ala Pro Val Arg Leu Gly Arg Lys Arg Pro Leu Pro Ala Cys
 1               5                  10                  15

Pro Asn Pro Leu Phe Val Arg Trp Leu Thr Glu Trp Arg Asp Glu Ala
            20                  25                  30

Thr Arg Ser Arg Arg Thr Arg Phe Val Phe Gln Lys Ala Leu Arg
        35                  40                  45

Ser Leu Arg Arg Tyr Pro Leu Pro Leu Arg Ser Gly Lys Glu Ala Lys
    50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Arg Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Gly Leu Ser Leu
    210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly His Arg Pro Glu Leu Leu
        275                 280                 285

Arg Glu Leu Gln Arg Leu His Val Thr His Thr Val Arg Lys Leu His
    290                 295                 300

Val Gly Asp Phe Val Trp Val Ala Gln Glu Thr Asn Pro Arg Asp Pro
305                 310                 315                 320

Ala Ala Asn Pro Gly Glu Leu Val Leu Asp His Ile Val Glu Arg Lys
                325                 330                 335

Arg Leu Asp Asp Leu Cys Ser Ser Ile Ile Asp Gly Arg Phe Arg Glu
            340                 345                 350
```

```
Gln Lys Phe Arg Leu Lys Arg Cys Gly Leu Glu Arg Arg Val Tyr Leu
        355                 360                 365

Val Glu Glu His Gly Ser Val His Asn Leu Ser Leu Pro Glu Ser Thr
370                 375                 380

Leu Leu Gln Ala Val Thr Asn Thr Gln Val Ile Asp Gly Phe Phe Val
385                 390                 395                 400

Lys Arg Thr Ala Asp Ile Lys Glu Ser Ala Ala Tyr Leu Ala Leu Leu
                405                 410                 415

Thr Arg Gly Leu Gln Arg Leu Tyr Gln Gly His Thr Leu Arg Ser Arg
            420                 425                 430

Pro Trp Gly Thr Pro Gly Asn Pro Glu Ser Gly Ala Met Thr Ser Pro
        435                 440                 445

Asn Pro Leu Cys Ser Leu Leu Thr Phe Ser Asp Phe Asn Ala Gly Ala
    450                 455                 460

Ile Lys Asn Lys Ala Gln Ser Val Arg Glu Val Phe Ala Arg Gln Leu
465                 470                 475                 480

Met Gln Val Arg Gly Val Ser Gly Glu Lys Ala Ala Ala Leu Val Asp
                485                 490                 495

Arg Tyr Ser Thr Pro Ala Ser Leu Leu Ala Ala Tyr Asp Ala Cys Ala
            500                 505                 510

Thr Pro Lys Glu Gln Glu Thr Leu Leu Ser Thr Ile Lys Cys Gly Arg
        515                 520                 525

Leu Gln Arg Asn Leu Gly Pro Ala Leu Ser Arg Thr Leu Ser Gln Leu
    530                 535                 540

Tyr Cys Ser Tyr Gly Pro Leu Thr
545                 550

<210> SEQ ID NO 11
<211> LENGTH: 1788
<212> TYPE: DNA
<213> ORGANISM: Muscari sp.
<220> FEATURE:
<221> NAME/KEY: CDS
<222> LOCATION: (42)..(1694)
<223> OTHER INFORMATION: Mouse Mus81(1)

<400> SEQUENCE: 11
gaattcgccc ttgagactct gaaggagcca gtctagttct t atg gcg gag ccg gtc    56
                                              Met Ala Glu Pro Val
                                              1               5 cgc ctg ggc cgg aag cgt ccg ctg ccc gtt tgc ccc aac ccg ctc ttc    104
Arg Leu Gly Arg Lys Arg Pro Leu Pro Val Cys Pro Asn Pro Leu Phe
        10                  15                  20 gtt cgt tgg ctg acc gag tgg cgg gac gag gca gcc agc agg ggg cgc    152
Val Arg Trp Leu Thr Glu Trp Arg Asp Glu Ala Ala Ser Arg Gly Arg
        25                  30                  35 cac acg cgt ttc gtg ttt caa aag gca ttg cgc tcc ctc caa cgg tac    200
His Thr Arg Phe Val Phe Gln Lys Ala Leu Arg Ser Leu Gln Arg Tyr
    40                  45                  50 ccg cta cca ttg cgc agc ggg aag gaa gcc aag ata ctc cag cac ttc    248
Pro Leu Pro Leu Arg Ser Gly Lys Glu Ala Lys Ile Leu Gln His Phe
55                  60                  65 gga gac agg ctc tgc cgc atg ctg gac gaa aag ctg aag cag cac cta    296
Gly Asp Arg Leu Cys Arg Met Leu Asp Glu Lys Leu Lys Gln His Leu
70                  75                  80                  85 gca tca ggc ggt gac cat gcc ccc agc tca cca tct gga aag aag gga    344
Ala Ser Gly Gly Asp His Ala Pro Ser Ser Pro Ser Gly Lys Lys Gly
            90                  95                  100
```

```
gcc agc aaa ggg cca cct gag caa gtc cag gac tct tcc atg cca gtt     392
Ala Ser Lys Gly Pro Pro Glu Gln Val Gln Asp Ser Ser Met Pro Val
        105                 110                 115 ccc acc cag cct caa gca gga agc acc agt gtt ggc tat tgg cca gct     440
Pro Thr Gln Pro Gln Ala Gly Ser Thr Ser Val Gly Tyr Trp Pro Ala
        120                 125                 130 cag aac tca ggt gct cga gag atc ctg ctg caa ctc tac agg gag cac     488
Gln Asn Ser Gly Ala Arg Glu Ile Leu Leu Gln Leu Tyr Arg Glu His
        135                 140                 145 ctg aat tct gat ggc cac agc ttc cta acc aaa gag gag ctg ctg cag     536
Leu Asn Ser Asp Gly His Ser Phe Leu Thr Lys Glu Glu Leu Leu Gln
150                 155                 160                 165 aag tgt gcc cag aag acc ccc agg gta gtg cct gga agt tcg aaa ccc     584
Lys Cys Ala Gln Lys Thr Pro Arg Val Val Pro Gly Ser Ser Lys Pro
                170                 175                 180 tgg cct gcc ctc cgg agc ctc ctc cat agg aac ctc atc ctt gga acg     632
Trp Pro Ala Leu Arg Ser Leu Leu His Arg Asn Leu Ile Leu Gly Thr
                185                 190                 195 cat cgg cca gcc agg tat gca ctc aca cca gag ggt ctg gag ctg gct     680
His Arg Pro Ala Arg Tyr Ala Leu Thr Pro Glu Gly Leu Glu Leu Ala
                200                 205                 210 cag aag ctg gcc gag gcg gaa ggc ctg agc act cgg cac gct ggc ttt     728
Gln Lys Leu Ala Glu Ala Glu Gly Leu Ser Thr Arg His Ala Gly Phe
215                 220                 225 agg cca gag gaa cat cac gga gag gac tca gca gtt cca gaa gcc ttg     776
Arg Pro Glu Glu His His Gly Glu Asp Ser Ala Val Pro Glu Ala Leu
230                 235                 240                 245 tca gaa cct ggc acc acc gag ggg gcc gtc cag cag aga cca ctg gag     824
Ser Glu Pro Gly Thr Thr Glu Gly Ala Val Gln Gln Arg Pro Leu Glu
                250                 255                 260 cta agg cct agc gag tac aga gtg ctg ttg tgt gtg gac att ggc gaa     872
Leu Arg Pro Ser Glu Tyr Arg Val Leu Leu Cys Val Asp Ile Gly Glu
                265                 270                 275 acc aga ggg gca gga cac agg cta gaa atg ctc cga gag tta caa agg     920
Thr Arg Gly Ala Gly His Arg Leu Glu Met Leu Arg Glu Leu Gln Arg
                280                 285                 290 ctg cgt gtg ccc cac acc gta cgc aag cta cac gtt gga gac ttt gtg     968
Leu Arg Val Pro His Thr Val Arg Lys Leu His Val Gly Asp Phe Val
295                 300                 305 tgg gtg gca cag gag acc agg ccc aga gac cca gaa aga cct ggg gag    1016
Trp Val Ala Gln Glu Thr Arg Pro Arg Asp Pro Glu Arg Pro Gly Glu
310                 315                 320                 325 ctg gtc ctg gac cac att gtg gaa cgc aag cgg cta gat gac cta tgc    1064
Leu Val Leu Asp His Ile Val Glu Arg Lys Arg Leu Asp Asp Leu Cys
                330                 335                 340 agc agc atc att gac ggc cgc ttt cgg gag cag aag ttc cgc ctg aag    1112
Ser Ser Ile Ile Asp Gly Arg Phe Arg Glu Gln Lys Phe Arg Leu Lys
                345                 350                 355 cgc tgt ggc ctg ggg cac cgg gta tac tta gtg gaa gaa cat ggg tct    1160
Arg Cys Gly Leu Gly His Arg Val Tyr Leu Val Glu Glu His Gly Ser
                360                 365                 370 gtc cac aac ctt agc ctt ccc gag agc acc ttg ctg cag gct gtc aca    1208
Val His Asn Leu Ser Leu Pro Glu Ser Thr Leu Leu Gln Ala Val Thr
375                 380                 385 aac acc cag gtc att gat ggc ttt ttt gtg aag cga acc atg gat att    1256
Asn Thr Gln Val Ile Asp Gly Phe Phe Val Lys Arg Thr Met Asp Ile
390                 395                 400                 405 aag gag tcg gtt ggc tac ctg gcg ctt ttg aca aag ggc ctg gaa aga    1304
Lys Glu Ser Val Gly Tyr Leu Ala Leu Leu Thr Lys Gly Leu Glu Arg
                410                 415                 420
```

| | | | | | | | | | | | | | | | |
|---|---|---|---|---|---|---|---|---|---|---|---|---|---|---|---|
| ctg | tac | cag | ggc | cac | acc | cta | cgc | agc | cgc | cct | tgg | ggg | gcc | cca | ggg | 1352 |
| Leu | Tyr | Gln | Gly | His | Thr | Leu | Arg | Ser | Arg | Pro | Trp | Gly | Ala | Pro | Gly | |
| | | | 425 | | | | | 430 | | | | | 435 | | | |

```
ctg tac cag ggc cac acc cta cgc agc cgc cct tgg ggg gcc cca ggg      1352
Leu Tyr Gln Gly His Thr Leu Arg Ser Arg Pro Trp Gly Ala Pro Gly
            425                 430                 435 gct gct gaa tca gaa gca aag cct tcc aca aac cct ctc tgc tca ctc      1400
Ala Ala Glu Ser Glu Ala Lys Pro Ser Thr Asn Pro Leu Cys Ser Leu
            440                 445                 450 ctc acc ttc agt gac ttc aat gca gaa gct gtc aag aac aag gcc cag      1448
Leu Thr Phe Ser Asp Phe Asn Ala Glu Ala Val Lys Asn Lys Ala Gln
            455                 460                 465 tct gtg cga gaa gta ttt gcc cgg cag ctg atg cag gtg cgt gga ctg      1496
Ser Val Arg Glu Val Phe Ala Arg Gln Leu Met Gln Val Arg Gly Leu
470                 475                 480                 485 agt ggg gag aag gca gca gcc gtg gtg gat cga tac agc acc cct gcc      1544
Ser Gly Glu Lys Ala Ala Ala Val Val Asp Arg Tyr Ser Thr Pro Ala
                490                 495                 500 agt ctc ctg gct gct tat gat gcc tgt gcc acc gcg aag gag cag gag      1592
Ser Leu Leu Ala Ala Tyr Asp Ala Cys Ala Thr Ala Lys Glu Gln Glu
            505                 510                 515 atg ctc ttg agc acc atc aag tgt ggg cgt ctg cag agg aat ctg gga      1640
Met Leu Leu Ser Thr Ile Lys Cys Gly Arg Leu Gln Arg Asn Leu Gly
            520                 525                 530 ccc gct ctg agc agg acc ctg tac cag ttg tac tgc agc cac agc cct      1688
Pro Ala Leu Ser Arg Thr Leu Tyr Gln Leu Tyr Cys Ser His Ser Pro
535                 540                 545 ctg agc tgagctgtac caggagacgc tcgctcccca gcaccatct tcatctctac       1744
Leu Ser
550 caaggctggc tagccttta gcaagggcga attctgcaga tatc                     1788

<210> SEQ ID NO 12
<211> LENGTH: 551
<212> TYPE: PRT
<213> ORGANISM: Muscari sp.

<400> SEQUENCE: 12

Met Ala Glu Pro Val Arg Leu Gly Arg Lys Arg Pro Leu Pro Val Cys
  1               5                  10                  15

Pro Asn Pro Leu Phe Val Arg Trp Leu Thr Glu Trp Arg Asp Glu Ala
                 20                  25                  30

Ala Ser Arg Gly Arg His Thr Arg Phe Val Phe Gln Lys Ala Leu Arg
             35                  40                  45

Ser Leu Gln Arg Tyr Pro Leu Pro Leu Arg Ser Gly Lys Glu Ala Lys
         50                  55                  60

Ile Leu Gln His Phe Gly Asp Arg Leu Cys Arg Met Leu Asp Glu Lys
 65                  70                  75                  80

Leu Lys Gln His Leu Ala Ser Gly Gly Asp His Ala Pro Ser Ser Pro
                 85                  90                  95

Ser Gly Lys Lys Gly Ala Ser Lys Gly Pro Pro Glu Gln Val Gln Asp
            100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175
```

```
Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Glu Gly Leu Ser Thr
    210                 215                 220

Arg His Ala Gly Phe Arg Pro Glu Glu His His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Leu Glu Met Leu
        275                 280                 285

Arg Glu Leu Gln Arg Leu Arg Val Pro His Thr Val Arg Lys Leu His
    290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln Gly His Thr Leu Arg Ser Arg Pro
            420                 425                 430

Trp Gly Ala Pro Gly Ala Ala Glu Ser Glu Ala Lys Pro Ser Thr Asn
        435                 440                 445

Pro Leu Cys Ser Leu Leu Thr Phe Ser Asp Phe Asn Ala Glu Ala Val
    450                 455                 460

Lys Asn Lys Ala Gln Ser Val Arg Glu Val Phe Ala Arg Gln Leu Met
465                 470                 475                 480

Gln Val Arg Gly Leu Ser Gly Glu Lys Ala Ala Ala Val Val Asp Arg
                485                 490                 495

Tyr Ser Thr Pro Ala Ser Leu Leu Ala Ala Tyr Asp Ala Cys Ala Thr
            500                 505                 510

Ala Lys Glu Gln Glu Met Leu Leu Ser Thr Ile Lys Cys Gly Arg Leu
        515                 520                 525

Gln Arg Asn Leu Gly Pro Ala Leu Ser Arg Thr Leu Tyr Gln Leu Tyr
    530                 535                 540

Cys Ser His Ser Pro Leu Ser
545                 550

<210> SEQ ID NO 13
<211> LENGTH: 1766
<212> TYPE: DNA
<213> ORGANISM: Muscari sp.
```

```
<220> FEATURE:
<221> NAME/KEY: CDS
<222> LOCATION: (52)..(1323)
<223> OTHER INFORMATION: Mouse Mus81(2)

<400> SEQUENCE: 13
gatatctgca gaattcgccc ttgagactct gaaggagcca gtctagttct t atg gcg        57
                                                        Met Ala
                                                         1 gag ccg gtc cgc ctg ggc cgg aag cgt ccg ctg ccc gtt tgc ccc aac        105
Glu Pro Val Arg Leu Gly Arg Lys Arg Pro Leu Pro Val Cys Pro Asn
        5                  10                  15 ccg ctc ttc gtt cgt tgg ctg acc gag tgg cgg gac gag gca gcc agc        153
Pro Leu Phe Val Arg Trp Leu Thr Glu Trp Arg Asp Glu Ala Ala Ser
 20                  25                  30 agg ggg cgc cac acg cgt ttc gtg ttt caa aag gca ttg cgc tcc ctc        201
Arg Gly Arg His Thr Arg Phe Val Phe Gln Lys Ala Leu Arg Ser Leu
 35                  40                  45                  50 caa cgg tac ccg cta cca ttg cgc agc ggg aag gaa gcc aag ata ctc        249
Gln Arg Tyr Pro Leu Pro Leu Arg Ser Gly Lys Glu Ala Lys Ile Leu
                 55                  60                  65 cag cac ttc gga gac agg ctc tgc cgc atg ctg gac gaa aag ctg aag        297
Gln His Phe Gly Asp Arg Leu Cys Arg Met Leu Asp Glu Lys Leu Lys
             70                  75                  80 cag cac cta gca tca ggc ggt gac cat gcc ccc agc tca cca tct gga        345
Gln His Leu Ala Ser Gly Gly Asp His Ala Pro Ser Ser Pro Ser Gly
         85                  90                  95 aag aag gga gcc agc aaa ggg cca cct gag caa gtc cag gac tct tcc        393
Lys Lys Gly Ala Ser Lys Gly Pro Pro Glu Gln Val Gln Asp Ser Ser
    100                 105                 110 atg cca gtt ccc acc cag cct caa gca gga agc acc agt gtt ggc tat        441
Met Pro Val Pro Thr Gln Pro Gln Ala Gly Ser Thr Ser Val Gly Tyr
115                 120                 125                 130 tgg cca gct cag aac tca ggt gct cga gag atc ctg ctg caa ctc tac        489
Trp Pro Ala Gln Asn Ser Gly Ala Arg Glu Ile Leu Leu Gln Leu Tyr
                135                 140                 145 agg gag cac ctg aat tct gat ggc cac agc ttc cta acc aaa gag gag        537
Arg Glu His Leu Asn Ser Asp Gly His Ser Phe Leu Thr Lys Glu Glu
            150                 155                 160 ctg ctg cag aag tgt gcc cag aag acc ccc agg gta gtg cct gga agt        585
Leu Leu Gln Lys Cys Ala Gln Lys Thr Pro Arg Val Val Pro Gly Ser
        165                 170                 175 tcg aaa ccc tgg cct gcc ctc cgg agc ctc ctc cat agg aac ctc atc        633
Ser Lys Pro Trp Pro Ala Leu Arg Ser Leu Leu His Arg Asn Leu Ile
    180                 185                 190 ctt gga acg cat cgg cca gcc agg tat gca ctc aca cca gag ggt ctg        681
Leu Gly Thr His Arg Pro Ala Arg Tyr Ala Leu Thr Pro Glu Gly Leu
195                 200                 205                 210 gag ctg gct cag aag ctg gcc gag gcg gaa ggc ctg agc act cgg cac        729
Glu Leu Ala Gln Lys Leu Ala Glu Ala Glu Gly Leu Ser Thr Arg His
                215                 220                 225 gct ggc ttt agg cca gag gaa cat cac gga gag gac tca gca gtt cca        777
Ala Gly Phe Arg Pro Glu Glu His His Gly Glu Asp Ser Ala Val Pro
            230                 235                 240 gaa gcc ttg tca gaa cct ggc acc acc gag ggg gcc gtc cag cag aga        825
Glu Ala Leu Ser Glu Pro Gly Thr Thr Glu Gly Ala Val Gln Gln Arg
        245                 250                 255 cca ctg gag cta agg cct agc gag tac aga gtg ctg ttg tgt gtg gac        873
Pro Leu Glu Leu Arg Pro Ser Glu Tyr Arg Val Leu Leu Cys Val Asp
    260                 265                 270
```

```
att ggc gaa acc aga ggg gca gga cac agg cca gaa atg ctc cga gag      921
Ile Gly Glu Thr Arg Gly Ala Gly His Arg Pro Glu Met Leu Arg Glu
275                 280                 285                 290 tta caa agg ctg cgt gtg ccc cac acc gta cgc aag cta cac gtt gga      969
Leu Gln Arg Leu Arg Val Pro His Thr Val Arg Lys Leu His Val Gly
                295                 300                 305 gac ttt gtg tgg gtg gca cag gag acc agg ccc aga gac cca gaa aga     1017
Asp Phe Val Trp Val Ala Gln Glu Thr Arg Pro Arg Asp Pro Glu Arg
            310                 315                 320 cct ggg gag ctg gtc ctg gac cac att gtg gaa cgc aag cgg cta gat     1065
Pro Gly Glu Leu Val Leu Asp His Ile Val Glu Arg Lys Arg Leu Asp
325                 330                 335 gac cta tgc agc agc atc att gac ggc cgc ttt cgg gag cag aag ttc     1113
Asp Leu Cys Ser Ser Ile Ile Asp Gly Arg Phe Arg Glu Gln Lys Phe
        340                 345                 350 cgc ctg aag cgc tgt ggc ctg ggg cac cgg gta tac tta gtg gaa gaa     1161
Arg Leu Lys Arg Cys Gly Leu Gly His Arg Val Tyr Leu Val Glu Glu
355                 360                 365                 370 cat ggg tct gtc cac aac ctt agc ctt ccc gag agc acc ttg ctg cag     1209
His Gly Ser Val His Asn Leu Ser Leu Pro Glu Ser Thr Leu Leu Gln
                375                 380                 385 gct gtc aca aac acc cag gtc att gat ggc ttt ttt gtg aag cga acc     1257
Ala Val Thr Asn Thr Gln Val Ile Asp Gly Phe Phe Val Lys Arg Thr
            390                 395                 400 atg gat att aag gag tcg gtt ggc tac ctg gcg ctt ttg aca aag ggc     1305
Met Asp Ile Lys Glu Ser Val Gly Tyr Leu Ala Leu Leu Thr Lys Gly
        405                 410                 415 ctg gaa aga ctg tac cag tgacttcaat gcagaagctg tcaagaacaa            1353
Leu Glu Arg Leu Tyr Gln
    420 ggtaccaccc ctgcctcacc tctgctcggg tggcctaggc caaggtcacc cttaacacag   1413 gcctacccca accccaggcc cagtctgtgc gagaagtatt tgcccggcag ctgatgcagg   1473 tgcgtggact gagtggggag aaggcagcag ccgtggtgga tcgatacagc acccctgcca   1533 gtctcctggc tgcttatgat gcctgtgcca ccgcgaagga gcaggagatg ctcttgagca   1593 ccatcaagtg tgggcgtctg cagaggaatc tgggacccgc tctgagcagg accctgtacc   1653 agttgtactg cagccacagc cctctgagct gagctgtacc aggagacgct cgctccccag   1713 cacccatctt catctctacc aaggctggct agccttttag caagggcgaa ttc          1766

<210> SEQ ID NO 14
<211> LENGTH: 424
<212> TYPE: PRT
<213> ORGANISM: Muscari sp.

<400> SEQUENCE: 14

Met Ala Glu Pro Val Arg Leu Gly Arg Lys Arg Pro Leu Pro Val Cys
1               5                   10                  15

Pro Asn Pro Leu Phe Val Arg Trp Leu Thr Glu Trp Arg Asp Glu Ala
            20                  25                  30

Ala Ser Arg Gly Arg His Thr Arg Phe Val Phe Gln Lys Ala Leu Arg
        35                  40                  45

Ser Leu Gln Arg Tyr Pro Leu Pro Leu Arg Ser Gly Lys Glu Ala Lys
    50                  55                  60

Ile Leu Gln His Phe Gly Asp Arg Leu Cys Arg Met Leu Asp Glu Lys
65                  70                  75                  80

Leu Lys Gln His Leu Ala Ser Gly Gly Asp His Ala Pro Ser Ser Pro
                85                  90                  95
```

```
Ser Gly Lys Lys Gly Ala Ser Lys Gly Pro Pro Glu Gln Val Gln Asp
            100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Glu Gly Leu Ser Thr
    210                 215                 220

Arg His Ala Gly Phe Arg Pro Glu Glu His His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Pro Glu Met Leu
        275                 280                 285

Arg Glu Leu Gln Arg Leu Arg Val Pro His Thr Val Arg Lys Leu His
    290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln
            420

<210> SEQ ID NO 15
<211> LENGTH: 2016
<212> TYPE: DNA
<213> ORGANISM: Muscari sp.
<220> FEATURE:
<221> NAME/KEY: CDS
<222> LOCATION: (52)..(1644)
<223> OTHER INFORMATION: Mouse Mus81(3)

<400> SEQUENCE: 15
gatatctgca gaattcgccc ttgagactct gaaggagcca gtctagttct t atg gcg      57
                                                         Met Ala
                                                           1
```

```
gag ccg gtc cgc ctg ggc cgg aag cgt ccg ctg ccc gtt tgc ccc aac      105
Glu Pro Val Arg Leu Gly Arg Lys Arg Pro Leu Pro Val Cys Pro Asn
      5              10                  15 ccg ctc ttc gtt cgt tgg ctg acc gag tgg cgg gac gag gca gcc agc      153
Pro Leu Phe Val Arg Trp Leu Thr Glu Trp Arg Asp Glu Ala Ala Ser
     20                  25                  30 agg ggg cgc cac acg cgt ttc gtg ttt caa aag gca ttg cgc tcc ctc      201
Arg Gly Arg His Thr Arg Phe Val Phe Gln Lys Ala Leu Arg Ser Leu
 35                  40                  45                  50 caa cgg tac ccg cta cca ttg cgc agc ggg aag gaa gcc aag ata ctc      249
Gln Arg Tyr Pro Leu Pro Leu Arg Ser Gly Lys Glu Ala Lys Ile Leu
                 55                  60                  65 cag cac ttc gga gac agg ctc tgc cgc atg ctg gac gaa aag ctg aag      297
Gln His Phe Gly Asp Arg Leu Cys Arg Met Leu Asp Glu Lys Leu Lys
             70                  75                  80 cag cac cta gca tca ggc ggt gac cat gcc ccc agc tca cca tct gga      345
Gln His Leu Ala Ser Gly Gly Asp His Ala Pro Ser Ser Pro Ser Gly
         85                  90                  95 aag aag gga gcc agc aaa ggg cca cct gag caa gtc cag gac tct tcc      393
Lys Lys Gly Ala Ser Lys Gly Pro Pro Glu Gln Val Gln Asp Ser Ser
    100                 105                 110 atg cca gtt ccc acc cag cct caa gca gga agc acc agt gtt ggc tat      441
Met Pro Val Pro Thr Gln Pro Gln Ala Gly Ser Thr Ser Val Gly Tyr
115                 120                 125                 130 tgg cca gct cag aac tca ggt gct cga gag atc ctg ctg caa ctc tac      489
Trp Pro Ala Gln Asn Ser Gly Ala Arg Glu Ile Leu Leu Gln Leu Tyr
                135                 140                 145 agg gag cac ctg aat tct gat ggc cac agc ttc cta acc aaa gag gag      537
Arg Glu His Leu Asn Ser Asp Gly His Ser Phe Leu Thr Lys Glu Glu
            150                 155                 160 ctg ctg cag aag tgt gcc cag aag acc ccc agg gta gtg cct gga agt      585
Leu Leu Gln Lys Cys Ala Gln Lys Thr Pro Arg Val Val Pro Gly Ser
        165                 170                 175 tcg aaa ccc tgg cct gcc ctc cgg agc ctc ctc cat agg aac ctc atc      633
Ser Lys Pro Trp Pro Ala Leu Arg Ser Leu Leu His Arg Asn Leu Ile
    180                 185                 190 ctt gga acg cat cgg cca gcc agg tat gca ctc aca cca gag ggt ctg      681
Leu Gly Thr His Arg Pro Ala Arg Tyr Ala Leu Thr Pro Glu Gly Leu
195                 200                 205                 210 gag ctg gct cag aag ctg gcc gag gcg gaa ggc ctg agc act cgg cac      729
Glu Leu Ala Gln Lys Leu Ala Glu Ala Glu Gly Leu Ser Thr Arg His
                215                 220                 225 gct ggc ttt agg cca gag gaa cat cac gga gag gac tca gca gtt cca      777
Ala Gly Phe Arg Pro Glu Glu His His Gly Glu Asp Ser Ala Val Pro
            230                 235                 240 gaa gcc ttg tca gaa cct ggc acc acc gag ggg gcc gtc cag cag aga      825
Glu Ala Leu Ser Glu Pro Gly Thr Thr Glu Gly Ala Val Gln Gln Arg
        245                 250                 255 cca ctg gag cta agg cct agc gag tac aga gtg ctg ttg tgt gtg gac      873
Pro Leu Glu Leu Arg Pro Ser Glu Tyr Arg Val Leu Leu Cys Val Asp
    260                 265                 270 att ggc gaa acc aga ggg gca gga cac agg cca gaa atg ctc cga gag      921
Ile Gly Glu Thr Arg Gly Ala Gly His Arg Pro Glu Met Leu Arg Glu
275                 280                 285                 290 tta caa agg ctg cgt gtg ccc cac acc gta cgc aag cta cac gtt gga      969
Leu Gln Arg Leu Arg Val Pro His Thr Val Arg Lys Leu His Val Gly
                295                 300                 305 gac ttt gtg tgg gtg gca cag gag acc agg ccc aga gac cca gaa aga     1017
Asp Phe Val Trp Val Ala Gln Glu Thr Arg Pro Arg Asp Pro Glu Arg
            310                 315                 320
```

```
cct ggg gag ctg gtc ctg gac cac att gtg gaa cgc aag cgg cta gat         1065
Pro Gly Glu Leu Val Leu Asp His Ile Val Glu Arg Lys Arg Leu Asp
            325                 330                 335 gac cta tgc agc agc atc att gac ggc cgc ttt cgg gag cag aag ttc         1113
Asp Leu Cys Ser Ser Ile Ile Asp Gly Arg Phe Arg Glu Gln Lys Phe
    340                 345                 350 cgc ctg aag cgc tgt ggc ctg ggg cac cgg gta tac tta gtg gaa gaa         1161
Arg Leu Lys Arg Cys Gly Leu Gly His Arg Val Tyr Leu Val Glu Glu
355                 360                 365                 370 cat ggg tct gtc cac aac ctt agc ctt ccc gag agc acc ttg ctg cag         1209
His Gly Ser Val His Asn Leu Ser Leu Pro Glu Ser Thr Leu Leu Gln
                375                 380                 385 gct gtc aca aac acc cag gtc att gat ggc ttt ttt gtg aag cga acc         1257
Ala Val Thr Asn Thr Gln Val Ile Asp Gly Phe Phe Val Lys Arg Thr
            390                 395                 400 atg gat att aag gag tcg gtt ggc tac ctg gcg ctt ttg aca aag ggc         1305
Met Asp Ile Lys Glu Ser Val Gly Tyr Leu Ala Leu Leu Thr Lys Gly
        405                 410                 415 ctg gaa aga ctg tac cag cct tcc aca aac cct ctc tgc tca ctc ctc         1353
Leu Glu Arg Leu Tyr Gln Pro Ser Thr Asn Pro Leu Cys Ser Leu Leu
    420                 425                 430 acc ttc agt gac ttc aat gca gaa gct gtc aag aac aag gcc cag tct         1401
Thr Phe Ser Asp Phe Asn Ala Glu Ala Val Lys Asn Lys Ala Gln Ser
435                 440                 445                 450 gtg cga gaa gta ttt gcc cgg cag ctg atg cag gtg cgt gga ctg agt         1449
Val Arg Glu Val Phe Ala Arg Gln Leu Met Gln Val Arg Gly Leu Ser
                455                 460                 465 ggg gag aag gca gca gcc gtg gtg gat cga tac agc acc cct gcc agt         1497
Gly Glu Lys Ala Ala Ala Val Val Asp Arg Tyr Ser Thr Pro Ala Ser
            470                 475                 480 ctc ctg gct gct tat gat gcc tgt gcc acc gcg aag gag cag gag atg         1545
Leu Leu Ala Ala Tyr Asp Ala Cys Ala Thr Ala Lys Glu Gln Glu Met
        485                 490                 495 ctc ttg agc acc atc aag tgt ggg cgt ctg cag agg aat ctg gga ccc         1593
Leu Leu Ser Thr Ile Lys Cys Gly Arg Leu Gln Arg Asn Leu Gly Pro
    500                 505                 510 gct ctg agc agg acc ctg tac cag ttg tac tgc agc cac agc cct ctg         1641
Ala Leu Ser Arg Thr Leu Tyr Gln Leu Tyr Cys Ser His Ser Pro Leu
515                 520                 525                 530 agc tgagctgtac caggagacgc tcgctcccca gcacccatct tcatctctac              1694
Ser caaggctggc tagccttta gcaagggcga attccagcac actggcggcc gttactagtg         1754
gatccgagct cggtaccaag cttggcgtaa tcatggtcat agctgtttcc tgtgtgaaat       1814
tgttatccgc tcacaattcc acacaacata cgagccggaa gcataaagtg taaagcctgg       1874
ggtgcctaat gagtgagcta actcacatta ttgcgttgc gctcactgcc cgctttccag        1934
tcgggaaacc tgtcgtgcca gctgcattaa tgaatcggcc aacgcgcggg gagaggcggt       1994
ttgcgtattg ggcgctcttc cg                                                2016

<210> SEQ ID NO 16
<211> LENGTH: 531
<212> TYPE: PRT
<213> ORGANISM: Muscari sp.

<400> SEQUENCE: 16

Met Ala Glu Pro Val Arg Leu Gly Arg Lys Arg Pro Leu Pro Val Cys
1               5                   10                  15
```

-continued

```
Pro Asn Pro Leu Phe Val Arg Trp Leu Thr Glu Trp Arg Asp Glu Ala
         20                  25                  30

Ala Ser Arg Gly Arg His Thr Arg Phe Val Phe Gln Lys Ala Leu Arg
         35                  40                  45

Ser Leu Gln Arg Tyr Pro Leu Pro Leu Arg Ser Gly Lys Glu Ala Lys
 50                  55                  60

Ile Leu Gln His Phe Gly Asp Arg Leu Cys Arg Met Leu Asp Glu Lys
 65                  70                  75                  80

Leu Lys Gln His Leu Ala Ser Gly Gly Asp His Ala Pro Ser Ser Pro
                 85                  90                  95

Ser Gly Lys Lys Gly Ala Ser Lys Gly Pro Pro Glu Gln Val Gln Asp
                100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Gly Leu Ser Thr
210                 215                 220

Arg His Ala Gly Phe Arg Pro Glu Glu His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Pro Glu Met Leu
        275                 280                 285

Arg Glu Leu Gln Arg Leu Arg Val Pro His Thr Val Arg Lys Leu His
290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln Pro Ser Thr Asn Pro Leu Cys Ser
            420                 425                 430
```

```
Leu Leu Thr Phe Ser Asp Phe Asn Ala Glu Ala Val Lys Asn Lys Ala
            435                 440                 445

Gln Ser Val Arg Glu Val Phe Ala Arg Gln Leu Met Gln Val Arg Gly
    450                 455                 460

Leu Ser Gly Glu Lys Ala Ala Val Val Asp Arg Tyr Ser Thr Pro
465                 470                 475                 480

Ala Ser Leu Leu Ala Ala Tyr Asp Ala Cys Ala Thr Ala Lys Glu Gln
            485                 490                 495

Glu Met Leu Leu Ser Thr Ile Lys Cys Gly Arg Leu Gln Arg Asn Leu
            500                 505                 510

Gly Pro Ala Leu Ser Arg Thr Leu Tyr Gln Leu Tyr Cys Ser His Ser
            515                 520                 525

Pro Leu Ser
    530
```

<210> SEQ ID NO 17
<211> LENGTH: 1698
<212> TYPE: DNA
<213> ORGANISM: Muscari sp.
<220> FEATURE:
<221> NAME/KEY: CDS
<222> LOCATION: (52)..(1614)
<223> OTHER INFORMATION: Mouse Mus81(4)

<400> SEQUENCE: 17

```
gatatctgca gaattcgccc ttgagactct gaaggagcca gtctagttct t atg gcg    57
                                                         Met Ala
                                                           1 gag ccg gtc cgc ctg ggc cgg aag cgt ccg ctg ccc gtt tgc ccc aac   105
Glu Pro Val Arg Leu Gly Arg Lys Arg Pro Leu Pro Val Cys Pro Asn
         5                  10                  15 ccg ctc ttc gtt tgt tgg ctg acc gag tgg cgg gac gag gca gcc agc   153
Pro Leu Phe Val Cys Trp Leu Thr Glu Trp Arg Asp Glu Ala Ala Ser
         20                  25                  30 agg ggg cgc cac acg cgt ttc gtg ttt caa aag gca ttg cgc tcc ctc   201
Arg Gly Arg His Thr Arg Phe Val Phe Gln Lys Ala Leu Arg Ser Leu
 35                  40                  45                  50 caa cgg tac ccg cta cca ttg cgc agc ggg aag gaa gcc aag ata ctc   249
Gln Arg Tyr Pro Leu Pro Leu Arg Ser Gly Lys Glu Ala Lys Ile Leu
                 55                  60                  65 cag cac ttc gga gac agg ctc tgc cgc atg ctg gac gaa aag ctg aag   297
Gln His Phe Gly Asp Arg Leu Cys Arg Met Leu Asp Glu Lys Leu Lys
             70                  75                  80 cag cac cta gca tca ggc ggt gac cat gcc ccc agc tca cca tct gga   345
Gln His Leu Ala Ser Gly Gly Asp His Ala Pro Ser Ser Pro Ser Gly
             85                  90                  95 aag aag gga gcc agc aaa ggg cca cct gag caa gtc cag gac tct tcc   393
Lys Lys Gly Ala Ser Lys Gly Pro Pro Glu Gln Val Gln Asp Ser Ser
            100                 105                 110 atg cca gtt ccc acc cag cct caa gca gga agc acc agt gtt ggc tat   441
Met Pro Val Pro Thr Gln Pro Gln Ala Gly Ser Thr Ser Val Gly Tyr
115                 120                 125                 130 tgg cca gct cag aac tca ggt gct cga gag atc ctg ctg caa ctc tac   489
Trp Pro Ala Gln Asn Ser Gly Ala Arg Glu Ile Leu Leu Gln Leu Tyr
                135                 140                 145 agg gag cac ctg aat tct gat ggc cac agc ttc cta acc aaa gag gag   537
Arg Glu His Leu Asn Ser Asp Gly His Ser Phe Leu Thr Lys Glu Glu
            150                 155                 160
```

```
ctg ctg cag aag tgt gcc cag aag acc ccc agg gta gtg cct gga agt        585
Leu Leu Gln Lys Cys Ala Gln Lys Thr Pro Arg Val Val Pro Gly Ser
            165                 170                 175 tcg aaa ccc tgg cct gcc ctc cgg agc ctc ctc cat agg aac ctc atc        633
Ser Lys Pro Trp Pro Ala Leu Arg Ser Leu Leu His Arg Asn Leu Ile
        180                 185                 190 ctt gga acg cat cgg cca gcc agg tat gca ctc aca cca gag ggt ctg        681
Leu Gly Thr His Arg Pro Ala Arg Tyr Ala Leu Thr Pro Glu Gly Leu
195                 200                 205                 210 gag ctg gct cag aag ctg gcc gag gcg gaa ggc ctg agc act cgg cac        729
Glu Leu Ala Gln Lys Leu Ala Glu Ala Glu Gly Leu Ser Thr Arg His
                215                 220                 225 gct ggc ttt agg cca gag gaa cat cac gga gag gac tca gca gtt cca        777
Ala Gly Phe Arg Pro Glu Glu His His Gly Glu Asp Ser Ala Val Pro
            230                 235                 240 gaa gcc ttg tca gaa cct ggc acc acc gag ggg gcc gtc cag cag aga        825
Glu Ala Leu Ser Glu Pro Gly Thr Thr Glu Gly Ala Val Gln Gln Arg
        245                 250                 255 cca ctg gag cta agg cct agc gag tac aga gtg ctg ttg tgt gtg gac        873
Pro Leu Glu Leu Arg Pro Ser Glu Tyr Arg Val Leu Leu Cys Val Asp
260                 265                 270 att ggc gaa acc aga ggg gca gga cac agg cca gaa atg ctc cga gag        921
Ile Gly Glu Thr Arg Gly Ala Gly His Arg Pro Glu Met Leu Arg Glu
275                 280                 285                 290 tta caa agg ctg cgt gtg ccc cac acc gta cgc aag cta cac gtt gga        969
Leu Gln Arg Leu Arg Val Pro His Thr Val Arg Lys Leu His Val Gly
                295                 300                 305 gac ttt gtg tgg gtg gca cag gag acc agg ccc aga gac cca gaa aga       1017
Asp Phe Val Trp Val Ala Gln Glu Thr Arg Pro Arg Asp Pro Glu Arg
            310                 315                 320 cct ggg gag ctg gtc ctg gac cac att gtg gaa cgc aag cgg cta gat       1065
Pro Gly Glu Leu Val Leu Asp His Ile Val Glu Arg Lys Arg Leu Asp
        325                 330                 335 gac cta tgc agc agc atc att gac ggc cgc ttt cgg gag cag aag ttc       1113
Asp Leu Cys Ser Ser Ile Ile Asp Gly Arg Phe Arg Glu Gln Lys Phe
340                 345                 350 cgc ctg aag cgc tgt ggc ctg ggg cac cgg gta tac tta gtg gaa gaa       1161
Arg Leu Lys Arg Cys Gly Leu Gly His Arg Val Tyr Leu Val Glu Glu
355                 360                 365                 370 cat ggg tct gtc cac aac ctt agc ctt ccc gag agc acc ttg ctg cag       1209
His Gly Ser Val His Asn Leu Ser Leu Pro Glu Ser Thr Leu Leu Gln
                375                 380                 385 gct gtc aca aac acc cag gtc att gat ggc ttt ttt gtg aag cga acc       1257
Ala Val Thr Asn Thr Gln Val Ile Asp Gly Phe Phe Val Lys Arg Thr
            390                 395                 400 atg gat att aag gag tcg gtt ggc tac ctg gcg ctt ttg aca aag ggc       1305
Met Asp Ile Lys Glu Ser Val Gly Tyr Leu Ala Leu Leu Thr Lys Gly
        405                 410                 415 ctg gaa aga ctg tac cag gcc aag gtc acc ctt aac aca ggc tac ccc       1353
Leu Glu Arg Leu Tyr Gln Ala Lys Val Thr Leu Asn Thr Gly Leu Pro
420                 425                 430 caa ccc cag gcc cag tct gtg cga gaa gta ttt gcc cgg cag ctg atg       1401
Gln Pro Gln Ala Gln Ser Val Arg Glu Val Phe Ala Arg Gln Leu Met
435                 440                 445                 450 cag gtg cgt gga ctg agt ggg gag aag gca gca gcc gtg gtg gat cga       1449
Gln Val Arg Gly Leu Ser Gly Glu Lys Ala Ala Ala Val Val Asp Arg
                455                 460                 465 tac agc acc cct gcc agt ctc ctg gct gct tat gat gcc tgt gcc acc       1497
Tyr Ser Thr Pro Ala Ser Leu Leu Ala Ala Tyr Asp Ala Cys Ala Thr
            470                 475                 480
```

-continued

```
gcg aag gag cag gag atg ctc ttg agc acc atc aag tgt ggg cgt ctg    1545
Ala Lys Glu Gln Glu Met Leu Leu Ser Thr Ile Lys Cys Gly Arg Leu
485                 490                 495 cag agg aat ctg gga ccc gct ctg agc agg acc ctg tac cag ttg tac    1593
Gln Arg Asn Leu Gly Pro Ala Leu Ser Arg Thr Leu Tyr Gln Leu Tyr
    500                 505                 510 tgc agc cac agc cct ctg agc tgagctgtac caggagacgc tcgctcccca       1644
Cys Ser His Ser Pro Leu Ser
515                 520 gcacccatct tcatctctac caaggctggc tagccttta gcaagggcga attc          1698
```

<210> SEQ ID NO 18
<211> LENGTH: 521
<212> TYPE: PRT
<213> ORGANISM: Muscari sp.

<400> SEQUENCE: 18

```
Met Ala Glu Pro Val Arg Leu Gly Arg Lys Arg Pro Leu Pro Val Cys
 1               5                  10                  15

Pro Asn Pro Leu Phe Val Cys Trp Leu Thr Glu Trp Arg Asp Glu Ala
             20                  25                  30

Ala Ser Arg Gly Arg His Thr Arg Phe Val Phe Gln Lys Ala Leu Arg
         35                  40                  45

Ser Leu Gln Arg Tyr Pro Leu Pro Leu Arg Ser Gly Lys Glu Ala Lys
     50                  55                  60

Ile Leu Gln His Phe Gly Asp Arg Leu Cys Arg Met Leu Asp Glu Lys
 65                  70                  75                  80

Leu Lys Gln His Leu Ala Ser Gly Gly Asp His Ala Pro Ser Ser Pro
                 85                  90                  95

Ser Gly Lys Lys Gly Ala Ser Lys Gly Pro Pro Glu Val Gln Asp
            100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Gly Leu Ser Thr
    210                 215                 220

Arg His Ala Gly Phe Arg Pro Glu Glu His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Pro Glu Met Leu
        275                 280                 285

Arg Glu Leu Gln Arg Leu Arg Val Pro His Thr Val Arg Lys Leu His
    290                 295                 300
```

```
Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
            325                 330                 335

Leu Asp Asp Leu Cys Ser Ser Ile Ile Asp Gly Arg Phe Arg Glu Gln
        340                 345                 350

Lys Phe Arg Leu Lys Arg Cys Gly Leu Gly His Arg Val Tyr Leu Val
    355                 360                 365

Glu Glu His Gly Ser Val His Asn Leu Ser Leu Pro Glu Ser Thr Leu
370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln Ala Lys Val Thr Leu Asn Thr Gly
            420                 425                 430

Leu Pro Gln Pro Gln Ala Gln Ser Val Arg Glu Val Phe Ala Arg Gln
        435                 440                 445

Leu Met Gln Val Arg Gly Leu Ser Gly Glu Lys Ala Ala Ala Val Val
    450                 455                 460

Asp Arg Tyr Ser Thr Pro Ala Ser Leu Leu Ala Ala Tyr Asp Ala Cys
465                 470                 475                 480

Ala Thr Ala Lys Glu Gln Glu Met Leu Leu Ser Thr Ile Lys Cys Gly
                485                 490                 495

Arg Leu Gln Arg Asn Leu Gly Pro Ala Leu Ser Arg Thr Leu Tyr Gln
            500                 505                 510

Leu Tyr Cys Ser His Ser Pro Leu Ser
            515                 520

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:5' primer

<400> SEQUENCE: 19
atggcggccc cggtccg                                                  17

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:3' primer

<400> SEQUENCE: 20
ctacggcccc ttgacctga                                                19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:5' primer

<400> SEQUENCE: 21
gacatggcgg ccccggtccg                                               20
```

```
<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:3' primer

<400> SEQUENCE: 22
gactcaggtc aagggccgt ag                                        22

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:5' primer

<400> SEQUENCE: 23
gagactctga aggagccag                                           19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:3' primer

<400> SEQUENCE: 24
gctaaaaggc tagccagcc                                           19

<210> SEQ ID NO 25
<211> LENGTH: 2439
<212> TYPE: DNA
<213> ORGANISM: Homo sapiens
<220> FEATURE:
<221> NAME/KEY: CDS
<222> LOCATION: (1)..(1365)
<220> FEATURE:
<221> NAME/KEY: mat_peptide
<222> LOCATION: (1)..(1368)
<223> OTHER INFORMATION: Short Hmus81
<220> FEATURE:
<221> NAME/KEY: CDS
<222> LOCATION: (1)..(1857)
<223> OTHER INFORMATION: long Hmus81 protein
<220> FEATURE:
<221> NAME/KEY: gene
<222> LOCATION: (1)..(1273)
<220> FEATURE:
<221> NAME/KEY: CDS
<222> LOCATION: (1)..(1275)
<220> FEATURE:
<221> NAME/KEY: mat_peptide
<222> LOCATION: (1)..(1273)
<223> OTHER INFORMATION: first part of long Hmus81 protein
<220> FEATURE:
<221> NAME/KEY: CDS
<222> LOCATION: (1475)..(1855)
<220> FEATURE:
<221> NAME/KEY: mat_peptide
<222> LOCATION: (1475)..(1854)
<223> OTHER INFORMATION: second part of long Hmus81 protein
<220> FEATURE:
<221> NAME/KEY: mat_peptide
<222> LOCATION: (1)..(1273)
<220> FEATURE:
<221> NAME/KEY: mat_peptide
<222> LOCATION: (1475)..(1854)
<220> FEATURE:
<221> NAME/KEY: misc_feature
<222> LOCATION: ()..()
<223> OTHER INFORMATION: Human Mus81 encoding gene with insert
```

```
<400> SEQUENCE: 25 atg gcg gcc ccg gtc cgc ctg ggc cgg aag cgc ccg ctg cct gcc tgt       48
Met Ala Ala Pro Val Arg Leu Gly Arg Lys Arg Pro Leu Pro Ala Cys
 1               5                  10                  15 ccc aac ccg ctc ttc gtt cgc tgg ctg acc gag tgg cgg gac gag gcg       96
Pro Asn Pro Leu Phe Val Arg Trp Leu Thr Glu Trp Arg Asp Glu Ala
             20                  25                  30 acc cgc agc agg cac cgc acg cgc ttc gta ttt cag aag gcg ctg cgt      144
Thr Arg Ser Arg His Arg Thr Arg Phe Val Phe Gln Lys Ala Leu Arg
         35                  40                  45 tcc ctc cga cgg tac cca ctg ccg ctg cgc agc ggg aag gaa gct aag      192
Ser Leu Arg Arg Tyr Pro Leu Pro Leu Arg Ser Gly Lys Glu Ala Lys
 50                  55                  60 atc cta cag cac ttc gga gac ggg ctc tgc cgg atg ctg gac gag cgg      240
Ile Leu Gln His Phe Gly Asp Gly Leu Cys Arg Met Leu Asp Glu Arg
 65                  70                  75                  80 ctg cag cgg cac cga aca tcg ggc ggt gac cat gcc ccg gac tca cca      288
Leu Gln Arg His Arg Thr Ser Gly Gly Asp His Ala Pro Asp Ser Pro
                 85                  90                  95 tct gga gag aac agt cca gcc ccg cag ggg cga ctt gcg gaa gtc cag      336
Ser Gly Glu Asn Ser Pro Ala Pro Gln Gly Arg Leu Ala Glu Val Gln
            100                 105                 110 gac tct tcc atg cca gtt cct gcc cag ccc aaa gcg gga ggc tct ggc      384
Asp Ser Ser Met Pro Val Pro Ala Gln Pro Lys Ala Gly Gly Ser Gly
        115                 120                 125 agc tac tgg cca gct cgg cac tca gga gcc cga gtg ata ctg ctg gtg      432
Ser Tyr Trp Pro Ala Arg His Ser Gly Ala Arg Val Ile Leu Leu Val
    130                 135                 140 ctc tac cgg gag cac ctg aat cct aat ggt cac cac ttc tta acc aag      480
Leu Tyr Arg Glu His Leu Asn Pro Asn Gly His His Phe Leu Thr Lys
145                 150                 155                 160 gag gag ctg ctg cag agg tgt gct cag aag tcc ccc agg gta gcc cct      528
Glu Glu Leu Leu Gln Arg Cys Ala Gln Lys Ser Pro Arg Val Ala Pro
                165                 170                 175 ggg agt gcc cca ccc tgg cca gcc ctc cgc tcc ctc ctt cac agg aac      576
Gly Ser Ala Pro Pro Trp Pro Ala Leu Arg Ser Leu Leu His Arg Asn
            180                 185                 190 ctg gtc ctc agg aca cac cag cca gcc agg tac tca ttg acc cca gag      624
Leu Val Leu Arg Thr His Gln Pro Ala Arg Tyr Ser Leu Thr Pro Glu
        195                 200                 205 ggc ctg gag ctg gcc cag aag ttg gcc gag tca gaa ggc ctg agc ttg      672
Gly Leu Glu Leu Ala Gln Lys Leu Ala Glu Ser Glu Gly Leu Ser Leu
    210                 215                 220 ctg aat gtg ggc atc ggg ccc aag gag ccc cct ggg gag gag aca gca      720
Leu Asn Val Gly Ile Gly Pro Lys Glu Pro Pro Gly Glu Glu Thr Ala
225                 230                 235                 240 gtg cca gga gca gct tca gca gag ctt gcc agt gaa gca ggg gtc cag      768
Val Pro Gly Ala Ala Ser Ala Glu Leu Ala Ser Glu Ala Gly Val Gln
                245                 250                 255 cag cag cca ctg gag ctg agg cct gga gag tac agg gtg ctg ttg tgt      816
Gln Gln Pro Leu Glu Leu Arg Pro Gly Glu Tyr Arg Val Leu Leu Cys
            260                 265                 270 gtg gac att ggc gag acc cgg ggg ggc cac agg ccg gag ctg ctc          864
Val Asp Ile Gly Glu Thr Arg Gly Gly His Arg Pro Glu Leu Leu
        275                 280                 285 cga gag cta cag cgg ctg cac gtg acc cac acg gtg cgc aag ctg cac      912
Arg Glu Leu Gln Arg Leu His Val Thr His Thr Val Arg Lys Leu His
    290                 295                 300
```

```
gtt gga gat ttt gtg tgg gtg gct cag gag acc aat cct aga gac cca     960
Val Gly Asp Phe Val Trp Val Ala Gln Glu Thr Asn Pro Arg Asp Pro
305                 310                 315                 320 gca aac cct ggg gag ttg gta ctg gat cac att gtg gag cgc aag cga    1008
Ala Asn Pro Gly Glu Leu Val Leu Asp His Ile Val Glu Arg Lys Arg
                325                 330                 335 ctg gat gac ctt tgc agc agc atc atc gac ggc cgc ttc cgg gag cag    1056
Leu Asp Asp Leu Cys Ser Ser Ile Ile Asp Gly Arg Phe Arg Glu Gln
340                 345                 350 aag ttc cga ctg aag cgc tgt ggt ctg gag cgc cgg gta tac ctg gtg    1104
Lys Phe Arg Leu Lys Arg Cys Gly Leu Glu Arg Arg Val Tyr Leu Val
        355                 360                 365 gaa gag cat ggt tcc gtc cac aac ctc agc ctt cct gag agc aca ctg    1152
Glu Glu His Gly Ser Val His Asn Leu Ser Leu Pro Glu Ser Thr Leu
370                 375                 380 ctg cag gct gtc acc aac act cag gtc att gat ggc ttt ttt gtg aag    1200
Leu Gln Ala Val Thr Asn Thr Gln Val Ile Asp Gly Phe Phe Val Lys
385                 390                 395                 400 cgc aca gca gac att aag gag tca gcc gcc tac ctg gcc ctc ttg act    1248
Arg Thr Ala Asp Ile Lys Glu Ser Ala Ala Tyr Leu Ala Leu Leu Thr
                405                 410                 415 cgg ggc ctg cag aga ctc tac cag gtg agc aga ggc ccc ttt ccc agt    1296
Arg Gly Leu Gln Arg Leu Tyr Gln Val Ser Arg Gly Pro Phe Pro Ser
        420                 425                 430 gtc ggg aca gag ccc aca agg aat tca cct tgc ctg ggc cct gtg cat    1344
Val Gly Thr Glu Pro Thr Arg Asn Ser Pro Cys Leu Gly Pro Val His
435                 440                 445 ccc caa aag aag caa ggt ggg tga gat ccc cat ttc tca ggc tgg ccc    1392
Pro Gln Lys Lys Gln Gly Gly     Asp Pro His Phe Ser Gly Trp Pro
450                 455             460 ccc aag gct gag gac tgg gca ggg gct ggc tgg agt tgt tcc ttc gag    1440
Pro Lys Ala Glu Asp Trp Ala Gly Ala Gly Trp Ser Cys Ser Phe Glu
465                 470                 475                 480 ctc cag cct ggc ctc agt ccc ttc ttc cct cag ggc cac acc cta cgc    1488
Leu Gln Pro Gly Leu Ser Pro Phe Phe Pro Gln Gly His Thr Leu Arg
                485                 490                 495 agc cgc ccc tgg gga acc cct ggg aac cct gaa tca ggg gcc atg acc    1536
Ser Arg Pro Trp Gly Thr Pro Gly Asn Pro Glu Ser Gly Ala Met Thr
        500                 505                 510 tct cca aac cct ctc tgc tca ctc ctc acc ttc agt gac ttc aac gca    1584
Ser Pro Asn Pro Leu Cys Ser Leu Leu Thr Phe Ser Asp Phe Asn Ala
515                 520                 525 gga gcc atc aag aat aag gcc cag tcg gtg cga gaa gtg ttt gcc cgg    1632
Gly Ala Ile Lys Asn Lys Ala Gln Ser Val Arg Glu Val Phe Ala Arg
                530                 535                 540 cag ctg atg cag gtg cgc gga gtg agt ggg gag aag gca gca gcc ctg    1680
Gln Leu Met Gln Val Arg Gly Val Ser Gly Glu Lys Ala Ala Ala Leu
545                 550                 555                 560 gtg gat cga tac agc acc cct gcc agc ctc ctg gcc gcc tat gat gcc    1728
Val Asp Arg Tyr Ser Thr Pro Ala Ser Leu Leu Ala Ala Tyr Asp Ala
                565                 570                 575 tgt gcc acc ccc aag gaa caa gag aca ctg ctg agc acc att aag tgt    1776
Cys Ala Thr Pro Lys Glu Gln Glu Thr Leu Leu Ser Thr Ile Lys Cys
        580                 585                 590 ggg cgt cta cag agg aat ctg ggg cct gct ctg agc agg acc tta tcc    1824
Gly Arg Leu Gln Arg Asn Leu Gly Pro Ala Leu Ser Arg Thr Leu Ser
595                 600                 605 cag ctc tac tgc agc tac ggc ccc ttg acc tga     agcagaggcc         1867
Gln Leu Tyr Cys Ser Tyr Gly Pro Leu Thr
        610                 615
```

```
cctttcccag tgtcgggaca gagcccacaa ggaattcacc ttgcctgggc cctgtgcatc      1927
cccaaaagaa gcaaggtggg tgagatcccc atttctcagg ctggcccccc aaggctgagg      1987
actgggcagg ggctggctgg agttgttcct tcgagctcca gcctggcctc agtcccttct      2047 tccctcagg gcc aca ccc tac gca gcc gcc cct ggg gaa ccc ctg gga acc      2098
         Ala Thr Pro Tyr Ala Ala Ala Pro Gly Glu Pro Leu Gly Thr
             620             625                 630 ctg aat cag ggg cca tga cct ctc caa acc ctc tct gct cac tcc tca        2146
Leu Asn Gln Gly Pro     Pro Leu Gln Thr Leu Ser Ala His Ser Ser
635                 640                 645 cct tca gtg act tca acg cag gag cca tca aga ata agg ccc agt cgg        2194
Pro Ser Val Thr Ser Thr Gln Glu Pro Ser Arg Ile Arg Pro Ser Arg
650                 655                 660                 665 tgc gag aag tgt ttg ccc ggc agc tga tgc agg tgc gcg gag tga gtg        2242
Cys Glu Lys Cys Leu Pro Gly Ser     Cys Arg Cys Ala Glu     Val
                670             675                 680 ggg aga agg cag cag ccc tgg tgg atc gat aca gca ccc ctg cca gcc        2290
Gly Arg Arg Gln Gln Pro Trp Trp Ile Asp Thr Ala Pro Leu Pro Ala
            685                 690                 695 tcc tgg ccg cct atg atg cct gtg cca ccc cca agg aac aag aga cac        2338
Ser Trp Pro Pro Met Met Pro Val Pro Pro Arg Asn Lys Arg His
        700                 705                 710 tgc tga gca cca tta agt gtg ggc gtc tac aga gga atc tgg ggc ctg        2386
Cys     Ala Pro Leu Ser Val Gly Val Tyr Arg Gly Ile Trp Gly Leu
    715                 720                 725 ctc tga gca gga cct tat ccc agc tct act gca gct acg gcc cct tga        2434
Leu     Ala Gly Pro Tyr Pro Ser Ser Thr Ala Ala Thr Ala Pro Pro
730                 735                 740                 745 cct ga                                                                 2439

<210> SEQ ID NO 26
<211> LENGTH: 455
<212> TYPE: PRT
<213> ORGANISM: Homo sapiens

<400> SEQUENCE: 26

Met Ala Ala Pro Val Arg Leu Gly Arg Lys Arg Pro Leu Pro Ala Cys
1               5                   10                  15

Pro Asn Pro Leu Phe Val Arg Trp Leu Thr Glu Trp Arg Asp Glu Ala
            20                  25                  30

Thr Arg Ser Arg His Arg Thr Arg Phe Val Phe Gln Lys Ala Leu Arg
        35                  40                  45

Ser Leu Arg Arg Tyr Pro Leu Pro Leu Arg Ser Gly Lys Glu Ala Lys
    50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160
```

```
Glu Glu Leu Leu Gln Arg Cys Ala Gln Lys Ser Pro Arg Val Ala Pro
            165                 170                 175

Gly Ser Ala Pro Pro Trp Pro Ala Leu Arg Ser Leu Leu His Arg Asn
        180                 185                 190

Leu Val Leu Arg Thr His Gln Pro Ala Arg Tyr Ser Leu Thr Pro Glu
            195                 200                 205

Gly Leu Glu Leu Ala Gln Lys Leu Ala Glu Ser Glu Gly Leu Ser Leu
        210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
            245                 250                 255

Gln Gln Pro Leu Glu Leu Arg Pro Gly Glu Tyr Arg Val Leu Leu Cys
        260                 265                 270

Val Asp Ile Gly Glu Thr Arg Gly Gly His Arg Pro Glu Leu Leu
            275                 280                 285

Arg Glu Leu Gln Arg Leu His Val Thr His Thr Val Arg Lys Leu His
        290                 295                 300

Val Gly Asp Phe Val Trp Val Ala Gln Glu Thr Asn Pro Arg Asp Pro
305                 310                 315                 320

Ala Asn Pro Gly Glu Leu Val Leu Asp His Ile Val Glu Arg Lys Arg
            325                 330                 335

Leu Asp Asp Leu Cys Ser Ser Ile Ile Asp Gly Arg Phe Arg Glu Gln
        340                 345                 350

Lys Phe Arg Leu Lys Arg Cys Gly Leu Glu Arg Arg Val Tyr Leu Val
        355                 360                 365

Glu Glu His Gly Ser Val His Asn Leu Ser Leu Pro Glu Ser Thr Leu
        370                 375                 380

Leu Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
            405                 410                 415

Arg Gly Leu Gln Arg Leu Tyr Gln Val Ser Arg Gly Pro Phe Pro Ser
        420                 425                 430

Val Gly Thr Glu Pro Thr Arg Asn Ser Pro Cys Leu Gly Pro Val His
        435                 440                 445

Pro Gln Lys Lys Gln Gly Gly
    450                 455

<210> SEQ ID NO 27
<211> LENGTH: 162
<212> TYPE: PRT
<213> ORGANISM: Homo sapiens

<400> SEQUENCE: 27

Asp Pro His Phe Ser Gly Trp Pro Pro Lys Ala Glu Asp Trp Ala Gly
1               5                   10                  15

Ala Gly Trp Ser Cys Ser Phe Glu Leu Gln Pro Gly Leu Ser Pro Phe
            20                  25                  30

Phe Pro Gln Gly His Thr Leu Arg Ser Arg Pro Trp Gly Thr Pro Gly
        35                  40                  45

Asn Pro Glu Ser Gly Ala Met Thr Ser Pro Asn Pro Leu Cys Ser Leu
    50                  55                  60

Leu Thr Phe Ser Asp Phe Asn Ala Gly Ala Ile Lys Asn Lys Ala Gln
65                  70                  75                  80
```

```
Ser Val Arg Glu Val Phe Ala Arg Gln Leu Met Gln Val Arg Gly Val
                85                  90                  95

Ser Gly Glu Lys Ala Ala Ala Leu Val Asp Arg Tyr Ser Thr Pro Ala
            100                 105                 110

Ser Leu Leu Ala Ala Tyr Asp Ala Cys Ala Thr Pro Lys Glu Gln Glu
        115                 120                 125

Thr Leu Leu Ser Thr Ile Lys Cys Gly Arg Leu Gln Arg Asn Leu Gly
130                 135                 140

Pro Ala Leu Ser Arg Thr Leu Ser Gln Leu Tyr Cys Ser Tyr Gly Pro
145                 150                 155                 160

Leu Thr

<210> SEQ ID NO 28
<211> LENGTH: 19
<212> TYPE: PRT
<213> ORGANISM: Homo sapiens

<400> SEQUENCE: 28

Ala Thr Pro Tyr Ala Ala Ala Pro Gly Glu Pro Leu Gly Thr Leu Asn
1               5                   10                  15

Gln Gly Pro

<210> SEQ ID NO 29
<211> LENGTH: 34
<212> TYPE: PRT
<213> ORGANISM: Homo sapiens

<400> SEQUENCE: 29

Pro Leu Gln Thr Leu Ser Ala His Ser Ser Pro Ser Val Thr Ser Thr
1               5                   10                  15

Gln Glu Pro Ser Arg Ile Arg Pro Ser Arg Cys Glu Lys Cys Leu Pro
            20                  25                  30

Gly Ser

<210> SEQ ID NO 30
<211> LENGTH: 5
<212> TYPE: PRT
<213> ORGANISM: Homo sapiens

<400> SEQUENCE: 30

Cys Arg Cys Ala Glu
1               5

<210> SEQ ID NO 31
<211> LENGTH: 34
<212> TYPE: PRT
<213> ORGANISM: Homo sapiens

<400> SEQUENCE: 31

Val Gly Arg Arg Gln Gln Pro Trp Trp Ile Asp Thr Ala Pro Leu Pro
1               5                   10                  15

Ala Ser Trp Pro Pro Met Met Pro Val Pro Pro Arg Asn Lys Arg
            20                  25                  30

His Cys

<210> SEQ ID NO 32
<211> LENGTH: 15
<212> TYPE: PRT
<213> ORGANISM: Homo sapiens
```

```
-continued

<400> SEQUENCE: 32

Ala Pro Leu Ser Val Gly Val Tyr Arg Gly Ile Trp Gly Leu Leu
 1               5                  10                  15

<210> SEQ ID NO 33
<211> LENGTH: 13
<212> TYPE: PRT
<213> ORGANISM: Homo sapiens

<400> SEQUENCE: 33

Ala Gly Pro Tyr Pro Ser Ser Thr Ala Ala Thr Ala Pro
 1               5                  10
```

HUMAN AND MURINE MUS81 PROTEINS

REFERENCE TO RELATED APPLICATIONS

The present application is a division of U.S. patent application Ser. No. 10/229,355, filed on Aug. 27, 2002, now U.S. Pat. No. 7,214,790, which is a division of U.S. patent application Ser. No. 09/661,711, filed on Sep. 14, 2000, now U.S. Pat. No. 6,440,732, which claims the benefit of U.S. Provisional Application for Patent Ser. No. 60/153,836, filed on Sep. 14, 1999, each of which is incorporated herein by reference.

GOVERNMENTAL RIGHTS

This invention was made with government support under Grant Nos. CA77325 and GM19234 from the National Institutes of Health. The United States government has certain rights in this invention.

FIELD OF THE INVENTION

The present invention relates generally to the field of medicine, and relates specifically to methods and compositions for modulating cell growth and death, including cell formation of tissues, using novel proteins, variants of these proteins and nucleic acids encoding them.

BACKGROUND OF THE INVENTION

The integrity of the genome is of prime importance to a dividing cell. In response to DNA damage, eukaryotic cells rely upon a complex system of controls to delay cell-cycle progression. The normal eukaryotic cell-cycle is divided into 4 phases (sequentially G1, S, G2, M) which correlate with distinct cell morphology and biochemical activity. Cells withdrawn from the cell-cycle are said to be in G0, or non-cycling state. When cells within the cell-cycle are actively replicating, duplication of DNA occurs in the S phase, and active division of the cell occurs in M phase. See generally Benjamin Lewin, *GENES VI* (Oxford University Press, Oxford, GB, Chapter 36, 1997). DNA is organized in the eukaryotic cell into successively higher levels of order that result in the formation of chromosomes. Non-sex chromosomes are normally present in pairs, and during cell division, the DNA of each chromosome replicates resulting in paired chromatids. (See generally Benjamin Lewin, *GENES VI* (Oxford University Press, Oxford, GB, Chapter 5, 1997).

The eukaryotic cell cycle is tightly regulated by intrinsic mechanisms that ensure ordered progression through its various phases and surveillance mechanisms that prevent cycling in the presence of aberrant or incompletely assembled structures. These negative regulatory surveillance mechanisms have been termed checkpoints (Hartwell and Weinert, 1989, "Checkpoints: controls that ensure the order of cell cycle events" *Science,* 246: 629-634). The mitotic checkpoint prevents cells from undergoing mitosis until all chromosomes have been attached to the mitotic spindle whereas the DNA structure checkpoint, which can be subdivided into the replication and DNA damage checkpoint, result in arrests at various points in the cell cycle in the presence of DNA damage or incompletely replicated DNA (Elledge, 1996, "Cell cycle checkpoints: preventing an identity crisis." *Science,* 274: 1664-1672). These arrests are believed to allow time for replication to be completed or DNA repair to take place. Cell cycling in the presence of DNA damage, incompletely replicated DNA or improper mitotic spindle assembly can lead to genomic instability, an early step in tumorigenesis. Defective checkpoint mechanisms, resulting from inactivation of the p53, ATM, and Bub1 checkpoint gene products have been implicated in several human cancers.

Checkpoint delays provide time for repair of damaged DNA prior to its replication in S-phase and prior to segregation of chromatids in M-phase (Hartwell and Weinert, 1989, supra.). In many cases the DNA-damage response pathways cause arrest by inhibiting the activity of the cyclin-dependent kinases (Elledge, 1997, supra.). In human cells the DNA-damage induced G2 delay is largely dependent on inhibitory phosphorylation of Cdc2 (Blasina et al., 1997, "The role of inhibitory phosphorylation of cdc2 following DNA replication block and radiation induced damage in Human cells." *Mol. Biol. Cell* 8: 1013-1023; Jin et al., 1997, "Role of inhibiting cdc2 phosphorylation in radiation-induced G2 arrest in human cells." *J. Cell Biol.,* 134: 963-970), and is therefore likely to result from a change in the activity of the opposing kinases and phosphatases that act on Cdc2. However, evidence that the activity of these enzymes is substantially altered in response to DNA damage is lacking (Poon et al., 1997, "The role of cdc2 feedback loop control in the DNA damage checkpoint in mammalian cells." *Cancer Res.,* 57: 5168-5178).

Three distinct Cdc25 proteins are expressed in human cells. Cdc25A is specifically required for the G1-S transition (Hoffmann et al., 1994, "Activation of the phosphatase activity of human CDC25A by a cdk2-cyclin E dependent phosphorylation at the G-1/S transition." *EMBO J.,* 13: 4302-4310; Jinno et al., 1994, "Cdc25A is a novel phosphatase functioning early in the cell cycle" *EMBO J.,* 13: 1549-1556), whereas Cdc25B and Cdc25C are required for the G2-M transition (Gabrielli et al., 1996, "Cytoplasmic accumulation of cdc25B phosphatase in mitosis triggers centrosomal microtubule mucleation in HeLa cells" *J. Cell Sci.,* 109(5): 1081-1093; Galaktionov et al., 1991, "Specific activation of cdc25 tyrosine phosphatases by B-type cyclins: evidence for multiple roles of mitotic cyclins" *Cell,* 67: 1181-1194; Millar et al., 1991, "p55CDC25 is a nuclear protein required for the initiation of mitosis in human cells" *Proc. Natl. Acad. Sci. USA,* 88: 10500-10504; Nishijima et al., 1997, *J. Cell Biol.,* 138: 1105-1116). The exact contribution of Cdc25B and Cdc25C to M-phase progression is not known.

Much of our current knowledge about checkpoint control has been obtained from studies using budding (*Saccharomyces cerevisiae*) and fission (*Schizosaccharomyces pombe*) yeast. A number of reviews of our current understanding of cell cycle checkpoint in yeast and higher eukaryotes have recently been published (Hartwell & Kastan, 1994, "Cell cycle control and Cancer" *Science* 266: 1821-1828; Murray, 1994, "Cell cycle checkpoints" *Current Opinions in Cell Biology,* 6: 872-876; Elledge, 1996, supra; Kaufmann & Paules, 1996, "DNA damage and cell cycle checkpoints" *FASEB J.,* 10: 238-247). In the fission yeast six gene products, rad1$^+$, rad3$^+$, rad9$^+$, rad17$^+$, rad26$^+$, and hus1$^+$ have been identified as components of both the DNA-damage dependent and DNA-replication dependent checkpoint pathways. In addition cds1$^+$ has been identified as being required for the DNA-replication dependent checkpoint and rad27$^+$/chk1$^+$ has been identified as required for the DNA-damage dependent checkpoint in yeast.

Several of these genes have structural homologues in the budding yeast. Further conservation across eukaryotes has recently been suggested with the cloning of several human homologues of *S. pombe* checkpoint genes, including two related to *S. pombe* rad3$^+$: ATM (ataxia telangiectasia mutated) (Savitsky et al., 1995, "A single ataxia telangiectasia gene with a product similar to PI-3 kinase" *Science*, 268: 1749-1753) and ATR (ataxia telangiectasia and rad3+ related) (Bentley et al., 1996, "The *Schizosaccharomyces pombe* rad3 checkpoint genes" *EMBO J.*, 15: 6641-6651; Cimprich et al., "cDNA cloning and gene mapping of a candidate human cell cycle checkpoint protein" 1996, *Proc. Natl. Acad. Sci. USA*, 93: 2850-2855); and human homologues of *S. pombe* rad9+, Hrad9 (Lieberman et al., 1996, "A human homolog of the *Schizosaccharomyces pombe* rad9+ checkpoint control gene" *Proc. Natl. Acad. Sci. USA* 93: 13890-13895), Hrad1 (Parker et al., 1998, "Identification of a human homologue of the *Schizosaccharomyces pombe* rad17+ checkpoint gene" *J. Biol. Chem.* 273:18340-18346; Freire et al., 1998, "Human and mouse homologs of *Schizosaccharomyces pombe* rad1 (+) and *Saccharomyces cerevisia* RAD17: linkage to checkpoint control and mammalian meiosis" *Genes Dev.* 12:2560-2573; Udell et al., 1998, "Hrad1 and Mrad1 encode mammalian homologues of the fission yeast rad1(+) cell cycle checkpoint control gene" *Nucleic Acids Res.* 26:2971-3976), Hrad17 (Parker et al., 1998, supra), Hhus1 (Kostrub et al., 1998, "Hus1p, a conserved fission yeast checkpoint protein, interacts with Rad1p and is phosphorylated in response to DNA damage" *EMBO J.* 17:2055-2066), Hchk1 (Sanchez et al., 1997, "Conservation of the Chk1 checkpoint pathway in mammals: linkage of DNA damage to Cdk regulation through Cdc25" *Science* 277:1497-1501) and Hcds1 (Matusoka et al., 1998, "Linkage of ATM to cell cycle regulation by the Chk2 protein kinase" *Science* 282(5395):1893-1897; Blasina et al., 1999, "A human homologue of the checkpoint kinase Cds1 directly inhibits Cdc25 phosphatase" *Curr. Biology* 9(1):1-10).

Genetic and biochemical analysis of the checkpoint proteins in yeast and mammalian cells suggests that the checkpoint response is transmitted through a conventional signal transduction pathway. Hrad1, Hrad9, Hrad17, and Hhus1 transmit the signal emanating from damaged or incompletely replicated DNA to the central kinases ATM and ATR, which in turn activate the downstream kinases, Chk1 and Cds1. The DNA structure checkpoint responses ultimately lead to phosphorylation of the mitosis inducing phosphatase Cdc25 by Chk1 or Cds1. This phosphorylation event creates a binding site for 14-3-3 proteins that target Cdc25 for export from the nucleus to the cytoplasm, thus preventing it from removing an inhibitory phosphate from the cyclin dependent kinase, Cdc2. Removal of this inhibitory phosphate is required for passage from G2 to mitosis in every cell cycle. The DNA structure checkpoint responses prevent this from occurring and result in a G2/M arrest.

Whereas the Chk1 protein has been shown to be required for the G2/M DNA damage checkpoint in *S. pombe*, the replication checkpoint requires the activity of both Cds1 and Chk1. When replication is blocked by treatment with the ribonucleotide reductase inhibitor hydroxyurea (HU), wild type cells arrest prior to mitosis. A cds1chk1 double mutant fails to arrest in the presence of HU while both single mutants arrest normally (Russell, 1998, "Checkpoints on the road to mitosis" *Trends in Biochemical Sciences* 23(10):399-402). *S. pombe* Chk1 and Cds1 are both capable of phosphorylating Cdc25 and targeting it for binding by 14-3-3 proteins. Activation of the *S. pombe* Cds1 protein kinase by HU also results in enhanced binding to and phosphorylation of Wee1, and accumulation of Mik1. These two protein kinases are required for the inhibitory phosphorylation of Cdc2 that prevents cells from entering mitosis suggesting an alternative to Cdc25C phosphorylation for checkpoint mediated cell cycle arrest. Recently, Cds1 has also been shown to be required for a DNA damage checkpoint in S-phase (Rhind and Russell, 1998, "The *Schizosaccharomyces pombe* S-phase checkpoint differentiates between different types of DNA damage" *Genetics* 149(4):1729-1737; Lindsay et al., 1998, "S-phase-specific activation of Cds1 kinase defines a subpathway of the checkpoint response in *Schizosaccharomyces pombe*" *Genes Dev.* 12(3):382-395). A human homologue of *S. pombe* Cds1 that is activated by DNA damage and HU in an ATM-dependent manner and is capable of phosphorylating Cdc25C in vitro was recently identified (Matsuoka et al., 1998, supra; Blasina et al., 1999, supra). The human cDNA encodes a 543 amino acid protein which like its *S. pombe* homologue, contains a forkhead associated (FHA) domain N-terminal to the kinase domain. FHA domains are found in several other proteins including the *S. cerevisiae* Cds1 orthologue Rad53. Rad53 contains two FHA domains, one of which is required for interaction with the DNA damage checkpoint protein Rad9 in the presence of DNA damage (Sun et al., 1998, "Rad53 FHA domain associated with phosphorylated Rad9 in the DNA damage checkpoint" *Science* 281(5374):272-274).

In order to develop new and more effective treatments and therapeutics for the amelioration of the effects of aging or disease such as cancer, it is important to identify and characterize mammalian, and in particular human, checkpoint proteins and to identify mediators of their activity. The present invention teaches the identification and characterization of human and murine nucleic acids encoding human Mus81 (Hmus81) and murine Mus81 (Mmus81) protein with significant homology to the *S. pombe* Mus81 protein that interacts with the *S. pombe* Cds1 FHA domain. The *S. cerevisiae* orthologue is reported to be involved in meiosis and DNA repair.

As described below, a Hmus81 gene acts as a checkpoint/repair gene and is involved with DNA repair. The checkpoint/repair delays provide time for repair of damaged DNA prior to its replication in S-phase and prior to segregation of chromatids in M-phase, and Hmus81 appears to act in both aspects, similarly to other known checkpoint/repair genes. In many cases, the DNA-damage response pathways will cause arrest, and the cell will fail to divide. However, a functional DNA repair mechanism will allow the damage to be corrected, and thus allow eventual cell division to occur.

In humans, excision repair is an important defense mechanism against two major carcinogens, sunlight and cigarette smoke. It has been found that individuals defective in excision repair exhibit a high incidence of cancer. (see Sancar, A, 1996, "DNA Excision Repair" *Ann. Rev. Biochem.* 65:43-81). Other mechanisms also act in a simiar manner to repair DNA, such as mismatch repair which stabilizes the cellular genome by correcting DNA replication errors and by blocking recombination events between divergent DNA sequences. Inactivation of genes encoding these activities results in a large increase in spontaneous mutability and predisposition to tumor development. (see Modrich & Lahue, 1996, "Mismatch Repair in Replication Fidelity, Genetic Recombination and Cancer Biology" *Ann. Rev. Biochem.* 65:101-33). The importance of maintaining fidelity in the DNA is amply illustrated by the many mechanisms for repair, and if unrepairable, arrest of cell division. (see Wood, R D, 1996, "DNA Repair in Eukaryotes" *Ann. Rev. Biochem.* 65:135-67).

Many chemotherapeutic agents are designed to disrupt or otherwise cause damage to the DNA of the targeted malignant cells. Antineoplastic agents such as alkylating agents, antimetabolites, and other chemical analogs and substances typically act by inhibiting nucleotide biosynthesis or protein synthesis, cross-linking DNA, or intercalating with DNA to inhibit replication or gene expression. Bleomycin and etoposide for example, specifically damage DNA and prevent repair.

The inhibition of Hmus81 gene or protein activity amplifies the potency of antineoplastic agents, and enhances the efficacy of their use as chemotherapeutic agents. This enhancement is beneficial in not only more thoroughly affecting the targeted cells, but by allowing for reduced dosages to be used in proportion to the increased efficacy, thus reducing unwanted side effects. Inhibition of Hmus81 or Mmus81 gene activity via anti-sense nucleic acid pharmaceuticals can be effected using the nucleic acids of the invention as the template for constructing the anti-sense nucleic acids. It is preferred to target the amino terminal end of the nucleic acid for anti-sense binding, and thus inhibition, as this reduces translation of the mRNA. Inhibition of Hmus81 protein activity can be effected by the use of altered or fragments of Hmus81 or Mmus81 protein to competitively inhibit the biochemical cascade that results in the repair of damaged DNA, or to cause cell arrest.

Disease can also result from defective DNA repair mechanisms, and include hereditary nonpolyposis colorectal cancer (defect in mismatch repair), Nijmegen breakage syndrome (defect in double strand break repair), Xeroderma pigmentosum, Cockayne syndrome, and Trocothiodystrophy (defect in nuclear excision repair). (see for example Lengauer et al., 1998, "Genetic instabilities in human cancers" *Nature* 396 (6712):643-649; Kanaar et al., 1998, "Molecular mechanisms of DNA double stranded repair" *Trends Cell Biol.* 8(12):483-489).

It is further envisioned that the transient inhibition of Hmus81 gene or protein activity can be sufficient to effect improved treatment of cell behavior due to aging or disease. For example, the transient inhibition of DNA checkpoint/DNA damage arrest of cell division may allow the combined use of lower doses of chemotherapeutic agents to effect greater damage to targeted cells in the treatment of diseases such as cancer.

SUMMARY OF THE INVENTION

Novel genes and proteins encoded thereby are useful for modifying cell growth, division and death. One aspect of the invention is a novel mammalian, e.g., human or murine checkpoint/repair protein, the nucleic acids which encode for it and its protein variants, nucleic acid constructs, and methods for the production and use of mammalian Mus81 encoding gene and protein. As used herein, "checkpoint gene" means a gene which encodes for a protein which acts in the checkpoint/repair regulation of cell division. Such protein can effect both replication and DNA damage checkpoint activity, ie. having checkpoint/repair activity. Specific characterization of the mammalian Mus81 protein encoding nucleic acids and their role in cell cycle regulation provides for novel and useful compounds for modulating the mammalian cell cycle in a target cell.

As used herein, the terms "human Mus81 gene", "Hmus81 encoding gene" and "Hmus81 gene" encompas human Mus81 encoding genes, including the allelic variants of the gene which will occur in a human population, but still encode for the same protein, splice variants of the gene, as well as the transcripts from such genomic genes, cDNA encoding for the transcript, and other nucleic acids which will encode a Hmus81 protein. As used herein, the terms "human Mus81 protein", "Hmus81" and "Hmus81 protein" refer generally to the protein expressed from a Hmus81 encoding nucleic acid, and includes splice variants and glycosylation variants of the protein which are generated by the translation and processing of the protein encoded by a Hmus81 encoding gene, and in particular to a human Mus81 protein having an amino acid sequence corresponding to that depicted as SEQ ID NO: 2, 4, 8, and 10. In a preferred embodiment, the isolated nucleic acids of the invention correspond to a cDNA that encodes for a human Mus81 protein. Any particular isolated nucleic acid of the invention, preferably encodes for only one form of a human Mus81 protein.

As described in detail below, the human Mus81 encoding nucleic acids of the invention encompasses isolated nucleic acids comprising a nucleotide sequence corresponding to the nucleotide sequences disclosed herein and specifically identified as Human Mus81$_1$ ("Hmus81(1)"; SEQ ID NO: 1), Human Mus81$_2$ ("Hmus81(2)"; SEQ ID NO: 3), Human Mus81$_3$ ("Hmus81(3)"; SEQ ID NO: 7), and Human Mus81$_4$ ("Hmus81(4)"; SEQ ID NO: 9). All of the foregoing nucleic acids encode for a human Mus81 protein, and its equivalents. Thus, the present invention encompasses a nucleic acid having a nucleotide sequence which encodes for a Hmus81 protein and specifically encompasses a nucleotide sequence corresponding to the coding domain segment of the sequences that are depicted as SEQ ID NO: 1, 3, 7, 9 and 25.

The present invention also encompasses a nucleic acid which encodes for two versions of Hmus81 protein having a nucleotide sequence corresponding to that depicted as SEQ ID NO:25. This nucleic acid encodes for a Hmus81 protein having an amino acid residue sequence depicted as SEQ ID NO: 4, wherein the 201 nucleotides from position 1274 to 1474 of the sequence of SEQ ID NO: 25 containing a stop codon, have been deleted, thus allowing translation of the longer coding domain segment sequence of DNA. The nucleic acid having a corresponding nucleotide sequence as that depicted as SEQ ID NO: 25 also encodes for the shorter Hmus81 protein having the amino acid sequence depicted as SEQ ID NO: 2, from a shorter coding domain segment, leaving the intron in place.

Thus, in a preferred embodiment, the present invention encompasses nucleic acids which encode for human Mus81 proteins, and in particular, nucleic acids having a coding domain segment sequence corresponding to that represented by nucleotides 23-1675 of the nucleotide sequence depicted as SEQ ID NO:1; to that represented by nucleotides 185-1549 of the nucleotide sequence depicted as SEQ ID NO:3; to that represented by nucleotides 26-1297 of the nucleotide sequence depicted as SEQ ID NO:7; to that represented by nucleotides 26-1681 of the nucleotide sequence depicted as SEQ ID NO:9; or as identified in SEQ ID NO: 25.

The terms "murine Mus81 gene" and "Mmus81 gene" are used herein to refer to the novel murine Mus81 encoding genes. The terms "murine Mus81 protein", "Mmus81" and "Mmus81 protein" refer generally to the protein product of the Mmus81 genes and in particular, to murine Mus81 proteins having an amino acid residue sequence corresponding to that depicted as SEQ ID NO: 12, 14, 16, and 18.

The terms "murine Mus81 gene", "Mmus81 gene" and "Mmus81 encoding gene" encompass the Mmus81 genes, and in particular isolated nucleic acids comprising a nucleotide sequence corresponding to the nucleotide sequences disclosed herein and identified as Mouse (murine) Mus81$_1$ ("Mmus81(1)"; SEQ ID NO: 11), Mouse Mus81$_2$ ("Mmus81 (2)"; SEQ ID NO: 13), Mouse Mus81$_3$ ("Mmus81(3)"; SEQ ID NO: 15), and Mouse Mus81$_4$ ("Mmus81(4)"; SEQ ID NO: 17), and the protein coding domain segments encoded for therein. In a preferred embodiment, the isolated nucleic acids of the invention correspond to a cDNA that encodes for a murine Mus81 protein. Any particular isolated nucleic acid of the invention, preferably encodes for only one form of a murine Mus81 protein.

In another preferred embodiment, the present invention encompasses nucleic acids which encode for murine Mus81 proteins, and in particular, nucleic acids which have a coding domain segment sequence corresponding to that represented by nucleotides 42-1694 of the nucleotide sequence depicted as SEQ ID NO:11; to that represented by nucleotides 15-1323 of the nucleotide sequence depicted as SEQ ID NO:13; to that represented by nucleotides 52-1644 of the nucleotide sequence depicted as SEQ ID NO:15; or to that represented by nucleotides 52-1614 of the nucleotide sequence depicted as SEQ ID NO:17.

The present invention also encompasses nucleic acid constructs, vectors, plasmids, cosmids, retrovirus or viral constructs and the like which contain a nucleotide sequence encoding for a human Mus81 or murine Mus81 protein. In particular, the present invention provides for nucleic acid vector constructs which contain the nucleotide sequence of the Hmus81 coding domain segments of the nucleic acid depicted as SEQ ID NO: 1, 3, 7, 9 or 25 and which are expressible as a protein. The present invention also provides for nucleic acid vector constructs which contain the Mmus81 coding domain segments of the nucleic acids depicted as SEQ ID NO: 11, 13, 15, or 17.

The term "transgene capable of expression" as used herein means a suitable nucleotide sequence which leads to expression of Hmus81 or Mmus81 proteins, having the same function and/or the same or similar biological activity as such protein. The transgene can include, for example, genomic nucleic acid isolated from mammalian cells (e.g. human or mouse) or synthetic nucleic acid, including DNA integrated into the genome or in an extrachromosomal state. Preferably, the transgene comprises the nucleotide sequence encoding the proteins according to the invention as described herein, or a biologically active portion of said protein. A biologically active protein should be taken to mean, and not limited to, a fusion product, fragment, digestion fragment, segment, domain or the like of a Mus81 protein having some if not all of the protein activity as a whole Mus81 protein. A biologically active protein thus contains a biologically functional portion of a mammalian Mus81 protein conveying a biochemical function thereof.

The present invention encompasses nucleic acid vectors that are suitable for the transformation of host cells, whether eukaryotic or prokaryotic, suitable for incorporation into viral vectors, or suitable for in vivo or in vitro protein expression. Particularly preferred host cells for prokaryotic expression of protein include, and are not limited to bacterial cells such as *E. coli*. Suitable host cells for eukaryotic expression of protein include, and are not limited to mammalian cells of human or murine origin and the like, or yeast cells. In a preferred embodiment, expression of protein, as described below, is accomplished by viral vector transformation of immortalized human cells.

The present invention further embodies a nucleotide sequence which encodes for a human Mus81 or murine Mus81 protein, in tandem with, or otherwise in conjunction with additional nucleic acids for the generation of fusion protein products. Human Mus81 fusion proteins will contain at least one segment of the protein encoded for by the nucleic acid depicted as the coding domain segment depicted in the nucleotide sequence described as SEQ ID NO: 1, 3, 7, and 9. Similarly, murine Mus81 fusion protein will contain at least one segment of protein encoded for by the coding domain segments of the nucleic acid depicted as SEQ ID NO: 11, 13, 15, and 17.

The present invention also encompasses isolated nucleic acids or nucleic acid vector constructs containing nucleic acid segments, adapted for use as naked DNA transformant vectors for incorporation and expression in target cells. Also provided are inhibitors of human Mus81 or murine Mus81 encoding nucleic acid transcripts, such as anti-sense DNA, triple-helix nucleic acid, double-helix RNA or the like. Biologically active anti-sense DNA molecule formulations are those which are the complement to the nucleotide sequence of the human Mus81 or murine Mus81 encoding genes or fragments thereof, whether complementary to contiguous or discontinuous portions of the targeted nucleotide sequence, and are inhibitors of the human Mus81 or murine Mus81 protein expression in cells. Such inhibitors and inhibition are useful for many purposes including and not limited to, in vitro analysis of the cell-cycle checkpoint pathway, detection and/or evaluation of inhibiting or potentiating compounds, and for in vivo therapy.

The present invention also provides for compositions incorporating modified nucleotides or substitute backbone components which encode for the nucleotide sequence of a human Mus81 or murine Mus81 encoding gene, or fragments thereof.

The present invention encompasses the use of anti-sense nucleic acids which comprise a nucleic acid that is the complement of at least a portion of a nucleic acid encoding for a human Mus81 or murine Mus81 protein. Also envisioned are biologically active analogs of this antisense molecule selected from the group consisting of peptide nucleic acids, methylphosphonates and 2-O-methyl ribonucleic acids. An antisense molecule of the invention can also be a phosphorothioate analog.

Also encompassed are pharmaceutical preparations for inhibiting Hmus81 protein expression or function in a cell which comprises an antisense nucleic acid analog which is capable of entering said cell and binding specifically to a nucleic acid molecule encoding for Hmus81 protein. The antisense nucleic acid is present in a pharmaceutically acceptable carrier and has a nucleotide sequence complementary to at least a portion of the nucleic acid of SEQ ID NO: 1, 3, 7, 9 or 25. It is also envisioned that this pharmaceutical preparation can comprise a nucleic acid having a sequence complementary to at least the nucleotides encoding for amino acid residues 1-50 of the amino acid residue sequence of SEQ ID NO: 2, 4, 8, or 10. In a preferred embodiment, the pharmaceutical preparation comprises a nucleic acid having a nucleotide sequence complementary to at least nucleotides 1-20 of a coding domain segment in the nucleotide sequence depicted as SEQ ID NO: 1, 3, 7, 9 or 25. In a most preferred embodiment, the antisense nucleic acid comprises a nucleic acid having a sequence complementary to at least nucleotides 1-10 of a coding domain segment in the nucleotide sequence depicted as SEQ ID NO: 1, 3, 7, 9 or 25.

The present invention also encompasses nucleotide sequences which would encode for the Hmus81 protein having an amino acid sequence as that depicted by that of SEQ ID NO: 2, 4, 8 or 10 based upon synonymous codon substitution given the knowledge of the triplet codons and which amino acids they encode, based upon the coding domain segment of the nucleotide sequence depicted in SEQ ID NO. 1, 3, 7, 9 or 25. The equivalent synonymous nucleic acid code for generating any nucleotide sequence which will encode for a protein having a particular amino acid sequence is known and predictable to one of skill in the art.

In a preferred embodiment codon usage is optimized to increase protein expression as desired for the target host cell, such as where a nucleic acid is modified so that it comprises a protein coding domain segment of the nucleotide sequence depicted in SEQ ID NO:1, 3, 7, 9, 11, 13, 15, 17 or 25, wherein the least preferred codons are substituted with those that are most preferred in the target host cell. In the case of human target host cells, the least preferred codons are ggg, att, ctc, tcc, and gtc.

The invention also provides for methods of generating human Mus81 or murine Mus81 protein, fusion proteins, or fragments thereof by using recombinant DNA technology and the appropriate nucleic acid encoding for human Mus81 or murine Mus81 protein. The invention provides for incorporating an appropriate nucleotide sequence into a suitable expression vector, the incorporation of suitable control elements such as a ribosome binding site, promoter, and/or enhancer element, either inducible or constitutively expressed. The invention provides for the use of expression vectors with or without at least one additional selectable marker or expressible protein. The invention provides for methods wherein a suitably constructed expression vector is transformed or otherwise introduced into a suitable host cell, and protein is expressed by such a host cell. The present invention also provides transformed host cells, which are capable of producing human Mus81 or murine Mus81 protein, fusion protein, or fragments thereof. The expression vector including said nucleic acid according to the invention may advantageously be used in vivo, such as in, for example, gene therapy.

The invention encompasses mammalian, e.g. human or murine Mus81 protein, fusion products, and biologically active portions thereof produced by recombinant DNA technology and expressed in vivo or in vitro. A biologically active portion of a protein is protein segment or fragment having the enzymatic activity of, or at least a some enzymatic activity of the whole mammalian Mus81 protein, when compared under similar conditions. For example, it will be readily apparent to persons skilled in the art that nucleotide substitutions or deletions may be introduced using routine techniques, which do not affect the protein sequence encoded by said nucleic acid, or which encode a biologically active, functional protein according to the invention. Manipulation of the protein to generate fragments as a result of enzyme digestion, or the modification of nucleic acids encoding for the protein can similarly result in biologically active portions of the mammalian Mus81 protein.

Complete protein, fusion products and biologically active portions thereof of the mammalian Mus81 protein are useful for therapeutic formulations, diagnostic testing, and as immunogens, as for example to generate antibodies thereto. The invention thus encompasses Hmus81 and Mmus81 protein produced by transformed host cells in small-scale or large-scale production. The invention encompasses complete Hmus81 and Mmus81 protein, in either glycosylated or unglycosylated forms, produced by either eukaryotic or prokaryotic cells. The present invention provides for Hmus81 and Mmus81 protein expressed from mammalian, insect, plant, bacterial, fungal, or any other suitable host cell using the appropriate transformation vector as known in the art. The present invention encompasses Hmus81 and Mmus81 protein that is produced as a fusion protein product, conjugated to a solid support, or Hmus81 and Mmus81 protein which is labeled with any chemical, radioactive, fluorescent, chemiluminescent or otherwise detectable marker.

The present invention also provides Hmus81 and Mmus81 proteins isolated from natural sources and enriched in purity over that found in nature. Also provided are pharmaceutical formulations of Hmus81 and Mmus81 protein as well as formulations of the Hmus81 and Mmus81 protein in pharmaceutically acceptable carriers or excipients.

The present invention also encompasses the use of human Mus81 or murine Mus81 protein, fusion protein, or biologically active fragments thereof to generate specific antibodies which bind specifically to the human Mus81 or murine Mus81 protein, or both, as either polyclonal or monoclonal antibodies generated by the immunization of a mammal with human Mus81 protein having the amino acid residue sequence, or an immunogenic fragment of the amino acid residue sequence shown as SEQ ID NO: 2, 4, 8, or 10, or the murine Mus81 protein having the amino acid residue sequence shown as SEQ ID NO: 12, 14, 16 or 18. An immunogenic fragment is one which will elicit an immune response, when injected into a immunologically competent host under immunogenic conditions, and generate antibodies specific for the immunogenic fragment.

The present invention also encompasses equivalent proteins where substitutions of amino acids for amino acid residues as shown in the amino acid sequence encoding for human Mus81 protein (SEQ ID NO: 2, 4, 8, 10) or murine Mus81 protein (SEQ ID NO:12, 14, 16, 18) are made. Such amino acid substitutions include conservative substitutions of similar amino acid residues that are reasonably predictable as being equivalent, or semi-conservative substitutions which have a reasonably predictable effect on solubility, glycosylation, or protein expression. For example, non-polar (hydrophobic side-chain) amino acids alanine, valine, leucine, isoleucine, proline, phenylalanine, tryptophan, methionine; uncharged polar amino acids glycine, serine, threonine, cysteine, tyrosine, asparagine, glutamine; charged polar amino acids aspartic acid, glutamic acid; basic amino acids lysine, arginine, and histidine are understood by those in the art to have functionally predictable effects when substituted. Amino acid substitutions also include replacement of amino acid residues with modified amino acid residues or chemically altered substitutes.

The present invention also encompasses nucleic acids which encode for such equivalent proteins and the embodiments thereof which encode for the human Mus81 proteins or murine Mus81 proteins. Specific modification can be made of codons used in the nucleic acids corresponding to the human Mus81 or murine Mus81 encoding genes of the invention such that the modified nucleic acids utilize codons preferred by the target host cell, while still encoding for the human Mus81 or murine Mus81 protein. This can be accomplished by conservative synonymous codon substitutions that reduce the number of less preferred codons and/or an increase in the number of preferred codons used by the target host cell The present invention also encompasses modified nucleic acids which incorporate, for example, internucleotide linkage modification, base modifications, sugar modification, nonradioactive labels, nucleic acid cross-linking, and altered backbones including PNAs (polypeptide nucleic acids).

The knowledge that Hmus81 acts as a checkpoint/repair protein and is most likely involved in DNA repair, allows for the use of the compounds of the invention in therapeutic treatment of diseases which involve abnormal DNA damage checkpoint/repair function, or that would advantageously inhibit DNA repair in a targeted cell. The present invention further provides for the use of the compounds of the present invention as therapeutics for the treatment of cancer. In one embodiment, inhibitors or agents which inhibit the function of the normal proteins and/or genes of the invention would be useful to sensitize cells for treatment with chemotherapeutics, radiation, DNA damaging agents, or replication inhibitors.

The present invention also encompasses methods for screening test compounds for efficacy in effecting the Mus81 mediated checkpoint/repair function of eukaryotic cells. These methods comprise contacting a test compound to eukaryotic cells, and detecting any change in mammalian Mus81 expression or function. Also encompassed are methods of screening wherein a compound is administered, and detection of change in Hmus81 or Mmus81 gene expression or function is accomplished by assaying for Hmus81 or Mmus81 mRNA production or by assaying for Hmus81 or Mmus81 protein expression. Methods for detection of changes in expression level of a particular gene are known in the art. In particular, the present invention allows for the screening of candidate substances for efficacy in modifying the mammalian Mus81 mediated DNA damage checkpoint/repair or DNA repair function by screening for any change in nuclease, phosphorylation or kinase activity of mammalian Mus81 protein. The compounds or substances identified by the assays of the invention, or compounds corresponding to such compounds or substances, can be used for the manufacture of pharmaceutical therapeutics.

Methods of identifying a chemical compound that modulates the Mus81 dependent cell cycle pathway are provided for as well. Such methods comprise administering the chemical compound to be tested to a host cell, and detecting the amount of mammalian Mus81 protein in said cell, and comparing the amount detected with that of a normal untreated cell. Further provided for is a method of identifying a chemical compound that modulates the Mus81 dependent cell cycle pathway, which method comprises administering the chemical compound to be tested to a biochemical mixture of Hmus81 protein and a suitable substrate, and detecting the level of Hmus81 protein activity in said mixture, and comparing the detected activity with that of a normal untreated biochemical mixture of Hmus81 protein. As shown in the examples below, isolated Hmus81 protein and suitable substrates can be measured in isolated chemical reactions.

In one embodiment, the present invention also provides for pharmaceutical compositions which comprise the Hmus81 protein, Hmus81 nucleic acid, or Hmus81 anti-sense nucleic acids. The therapeutic Hmus81 protein can be normally glycosylated, modified, or unglycosylated depending upon the desired characteristics for the protein. Similarly, Hmus81 protein includes the complete long or short protein, fusion product, or functional or immunogenic fragment thereof. Hmus81 nucleic acids include those encoding for the entire long or short protein, portions of the protein, fusion protein products, and fragments thereof. Also included are modified forms of nucleic acids including those incorporating substitute base analogs, modified bases, PNAs and those incorporating preferred codon usage. Anti-sense nucleic acids include complementary nucleic acids which can bind specifically to the targeted nucleic acids, having full, part or discontinuous segments of complementary nucleic acid which can be DNA, RNA or analog compounds thereof. In another embodiment, the present invention provides for compounds or substances identified as suitable for use as a therapeutic in pharmaceutical formulations by the assays of the invention. These pharmaceutical compositions can further include chemotherapeutic agents for the use in treating cancer, or be administered in a regimen coordinated with the administration of other anti-cancer therapies. The present invention, in one embodiment, encompasses methods for combined chemotherapy using the Hmus81 derived pharmaceuticals independently, and in combination with other chemotherapeutic agents, and in a second embodiment as admixtures with other anti-cancer therapeutics for single dose administration.

Similarly, murine Mus81 protein, or nucleic acids encoding for the protein can be used to modulate the cell cycle of murine or non-murine mammalian cells. Nucleic acids encoding for the murine Mus81 protein, can be used to produce murine Mus81 protein by recombinant means for use in pharmaceuticals, detection methods and kits, and assay systems in the same manner as human Mus81 protein.

The invention provides for a transgenic cell, transformed cell, tissue or organism comprising a transgene capable of expressing human Mus81 protein, which protein comprises the amino acid sequence illustrated in FIG. 1A (SEQ ID NO:2), FIG. 1B (SEQ ID NO:4), FIG. 1C (SEQ ID NO:8), FIG. 1D (SEQ ID NO:10), or a murine Mus81 protein, which protein comprises the amino acid sequence illustrated in FIG. 2A (SEQ ID NO:12), FIG. 2B (SEQ ID NO:14), FIG. 2C (SEQ ID NO:16), FIG. 2D (SEQ ID NO:18), or the amino acid sequence of a biologically active functional equivalent or bioprecursor or biologically active fragment therefor. And for the isolated protein produced by such transformed host cells.

BRIEF DESCRIPTION OF THE DRAWINGS

The invention may be better understood by reference to one or more of the following drawings in combination with the detailed description of specific embodiments, and claims presented herein.

FIG. 1 depicts nucleotide sequences of human Mus81 cDNA molecules and amino acid sequences of their translation products. FIG. 1A depicts the nucleotide sequence of a PCR product from cerebellum cDNA library encoding a 551 amino acid protein Hmus81(1) (SEQ ID NO: 1 and 2). FIG. 1B depicts the nucleotide sequence of IMAGE 128349 cDNA encoding a 455 amino acid protein Hmus81(2) (SEQ ID NO: 3 and 4). FIG. 1C depicts Sequence of a PCR product from cerebellum cDNA library encoding a 424 amino acid protein Hmus81(3) (SEQ ID NO: 7 and 8). FIG. 1D depicts a nucleotide sequence of a PCR product from cerebellum cDNA library encoding a 552 amino acid protein Hmus81(4) (SEQ ID NO: 9 and 10).

FIG. 2 depicts nucleic acid nucleotide sequences of mouse Mus81 cDNA molecules and amino acid sequences of their translation products. FIG. 2A depicts a nucleic acid encoding for Mmus81(1) and the amino acid sequence for the translated protein of 551 amino acids in length (SEQ ID NO: 11 and 12). FIG. 2B depicts a nucleic acid encoding for Mmus81(2) and the amino acid sequence for the translated protein of 424 amino acids in length (SEQ ID NO: 13 and 14). FIG. 2C depicts a nucleic acid encoding for Mmus81(3) and the amino acid sequence for the translated protein of 531 amino acids in length (SEQ ID NO: 15 and 16). FIG. 2D depicts a nucleic acid encoding for Mmus81(4) and the amino acid sequence for the translated protein of 521 amino acids in length (SEQ ID NO: 17 and 18).

FIG. 3 graphically presents an alignment of mouse (Mm) (Mmus81; SEQ ID NO:12), human (Hs) (Hmus81; SEQ ID NO:10), S. pombe (Sp) (Spmus81; SEQ ID NO:6), and S. cerevisiae (Sc) Mus81 (Scmus81; SEQ ID NO:5) amino acid sequences. Amino acids conserved in all proteins are highlighted in black and in two or more proteins in grey. Sequences underlined in red correspond to the conserved catalytic domain of the XPF family of endonucleases.

DETAILED DESCRIPTION OF THE INVENTION

Figure 4:
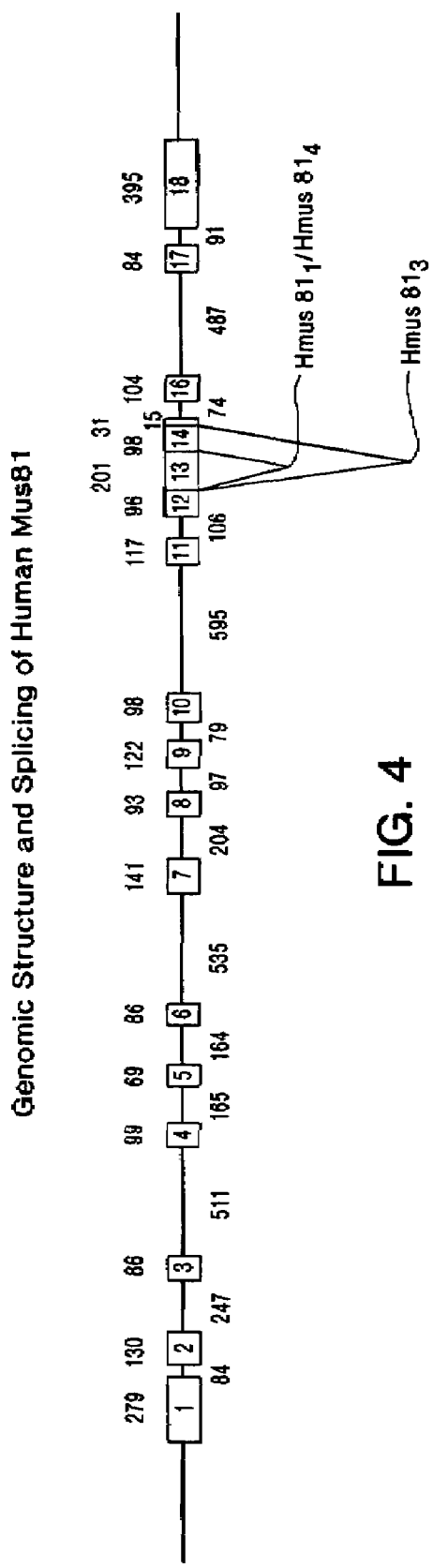
FIG. 4. Genomic structure and splicing variations of human Mus81. Solid line represents genomic sequence and boxes indicate positions of exons. Sizes of exons and introns (in bp) are indicated above and below the genomic fragment, respectively. Alternative splicing that occurs around exons 13 and 14 corresponds to Mus81$_1$, Mus81$_4$, and Mus81$_3$, is shown by thin lines. Mus81$_2$ utilizes all the identified exons.

The present invention, in one aspect, provides for isolated nucleic acids which encode for novel mammalian cell cycle check-point/repair proteins, such as human Mus81 proteins and murine Mus81 proteins and the like. The nucleic acids of the invention are useful for generating human Mus81 or murine Mus81 proteins using recombinant DNA techniques, for transforming target host cells as naked nucleic acid vectors, or when constructed in combination with nucleic acid regulatory elements such as promoters, enhancers, or supressors as expression vector constructs. Advantageously, the nucleic acid molecules according to the invention can be used as a medicament, or in the preparation of a medicament for modulating cell cycle checkpoint/repair functions of a target cell, for the treatment of cancer and other proliferative diseases.

The present invention also provides for isolated and/or recombinantly produced human and murine Mus81 proteins, and protein analogs. Recombinantly produced human Mus81 or murine Mus81 proteins of the invention can be used advantageously in vitro or in vivo for modulating the cell cycle and/or checkpoint/repair pathway of a targeted host cell. Isolated human Mus81 or murine Mus81 protein of the present invention may be utilized to generate antibodies which bind specifically to the human Mus81 protein and/or murine Mus81 protein, where such antibodies can be either polyclonal or monoclonal. Advantageously, the protein molecules according to the invention can be used as a medicament, or in the preparation of a medicament for modulating cell cycle checkpoint/repair functions of a target cell, for the treatment of cancer and other proliferative diseases.

Isolated recombinantly produced human and/or murine Mus81 proteins can also be used in combination with other proteins as in vitro biochemical systems for modeling enzymatic steps of an in vivo cell cycle checkpoint/repair pathway for testing and/or evaluating chemical or protein compounds for the ability to modulate the cell cycle checkpoint/repair mechanism associated with human Mus81 or murine Mus81 protein. A biochemical mixture of human Mus81 or murine Mus81 protein will comprise the isolated enzyme, appropriate ions and/or cofactors, and suitable substrate. A preferred biochemical mixture will comprise a suitable substrate which will detectably change or signal a change in state, when the enzymatic activity of the Mus81 protein has been applied to the substrate, for example by emission of energy, or fluorescent light, or an alteration in the wavelength of emitted light energy, or by a change in binding by a antibody molecule specific for a particular form of Mus81 protein.

The isolated nucleic acids of the invention, and the nucleotide sequence encoded by them, provide for isolated DNA, RNA, modified nucleotide analog, or labeled nucleic acid constructs which can mimic, complementarily bind to, and/or otherwise label nucleic acids comprising the same or highly related nucleotide sequences in nucleic acids in vitro or in vivo. It is envisioned that the nucleic acids of the invention can incorporate modified nucleotides and nucleic acid base analogs, which are known in the art (see for example Verma et al., 1998, "Modified Oligonucleotides" *Ann. Rev. Biochem.* 67: 99-134). The isolated nucleic acids of the present invention can be a biologically active antisense molecule, which is one capable of hybridizing to a target nucleic acid upon the complementary binding of nucleic acids and thereby modulate the expression of the targeted nucleic acid. Advantageously, the antisense molecule according to the invention can be used as a medicament, or in the preparation of a medicament for modulating cell cycle checkpoint/repair functions of a target cell, for the treatment of cancer and other proliferative diseases. Suitable biologically active antisense nucleic acids comprise modified nucleotide bases or the like for improving the stabilization of such nucleic acids or resistance to nucleases, such as (2'-O-(2-methoxy)ethyl (2'-MOE) modification of oligonucleotides (McKay et al., 1999, "Characterization of a potent and specific class of antisense oligonucleotide inhibitors of human PKC-alpha expression" *J. Biol. Chem.* 274:1715-1722). Preferred antisense nucleic acid molecules are at least 10 residues in length, preferably 20 residues in length, and are directed to a portion of the gene transcript that will result in the inhibition of translation of a functional protein from the gene transcript.

The present invention also advantageously provides for nucleotide sequences of at least approximately 15 nucleotides which are complementary to a contiguous portion of a nucleic acid according to the invention. These complementary sequences can be used as probes or primers to initiate replication, to detect the presence of nucleic acids having the nucleotide sequence of the invention, or to specifically amplify segments of the desired nucleic acid from a sample. Such complementary nucleotide sequences can be produced according to techniques well known in the art, such as by recombinant or synthetic means. The prepared primers, properly coordinated to specifically amplify a portion of a target nucleic acid in a sample may be used in diagnostic kits, or the like, for detecting the presence of a nucleic acid according to the invention. These tests generally comprise contacting the probe with the sample under hybridizing conditions and detecting for the presence of any duplex or triplex formation between the probe and any nucleic acid in the sample.

Advantageously, the nucleotide sequences embodying the invention can be produced using such recombinant or synthetic means, such as for example using PCR cloning mechanisms which generally involve making a pair of primers, which may be from approximately 15 to 50 nucleotides to a region of the gene which is desired to be cloned, bringing the primers into contact with mRNA, cDNA, or genomic DNA from a human cell, performing a polymerase chain reaction under conditions which bring about amplification of the desired region (and where necessary first performing a reverse transcription step), isolating the amplified region or fragment and recovering the amplified DNA. Advantageously, human allelic variants of the nucleic acid according to the invention can be obtained by for example, probing genomic DNA libraries from a range of individuals for example from different populations, and other genotyping techniques. Furthermore, nucleic acids and probes according to the invention may be used to sequence genomic DNA from patients, using techniques well known in the art, for example, the Sanger dideoxy chain termination method, which can advantageously ascertain any predisposition of a patient to certain proliferative disorders.

Specific modification of codons used in the nucleic acids corresponding to SEQ ID NO: 1, 3, 7, and 9 can be such that the modified nucleic acids utilize codons preferred by the target host cell, while still encoding for the Hmus81 protein. Similarly, the present invention encompasses specific modification of codons used in the nucleic acids corresponding to SEQ ID NO: 11, 13, 15, and 17 such that the modified nucleic acids utilize codons preferred by the target host cell, while still encoding for the Mmus81 protein. The present invention also encompasses modified nucleic acids which incorporate, for example, internucleotide linkage modification, base modifications, sugar modification, nonradioactive labels, nucleic acid cross-linking, and altered backbones including PNAs (polypeptide nucleic acids), as well as codon substitutions to reduce the number of less preferred codons and/or an increase in the number of preferred codons used by the target host cell (see Zhang et al., 1991, "Graphic analysis of codon usage strategy in 1490 human proteins" *Gene* 105(1):61-72; Zhang et al., 1993, "Low-usage codons in *Escherichia coli*, yeast, fruit fly and primates" *J. Protein Chemistry* 12(3):329-335).

According to one aspect of the present invention, there is provided a nucleic acid encoding Hmus81 protein having the amino acid residue sequence as illustrated as SEQ ID NO: 2, 4, 8, or 10, or encoding a functionally equivalent fragment, or bioprecursor of said protein. According to another aspect of the present invention, there is provided a nucleic acid encoding Mmus81 protein having the amino acid residue sequence as illustrated as SEQ ID NO: 12, 14, 16, or 18, or encoding a functionally equivalent fragment, or bioprecursor of said protein.

Preferably, the nucleic acid is a DNA molecule such as a genomic DNA molecule, and even more preferably a cDNA molecule. However, it may also be RNA. As is well known to those skilled in the art, due to the degeneracy of the triplet codon genetic code, the present nucleotide sequences can include substitutions therein yet which still encode the same amino acid residue sequence.

The nucleotide sequences defined herein are capable of hybridizing under low stringency conditions to nucleotide sequences derived from a nucleic acid of the invention, to identify homologs therefrom or alternatively to identify nucleotide sequences from other species.

The present nucleic acids can be incorporated into an expression vector and subsequently used to transform, transfect or infect a suitable host cell. In such an expression vector the nucleic acid according to the invention is operably linked to a control sequence, such as a suitable promoter or the like, ensuring expression of the proteins according to the invention in a suitable host cell. The expression vector can be a plasmid, cosmid, virus or other suitable vector. The expression vector and the host cell transfected, transformed or infected with the vector also form part of the present invention. Preferably, the host cell is a eukaryotic cell or a bacterial cell and even more preferably a mammalian cell or insect cell. Mammalian host cells are particularly advantageous because they provide the necessary post-translational modifications to the expressed proteins according to the invention, such as glycosylation or the like, which modifications confer optimal biological activity of said proteins, which when isolated can advantageously be used in diagnostic kits or the like.

The recombinant vectors of the invention generally comprise a Hmus81 gene or Mmus81 operatively positioned downstream from a promoter. The promoter is capable of directing expression of the human Mus81 or murine Mus81 encoding nucleic acid in a mammalian, e.g. human cell. Such promoters are thus "operative" in mammalian cells, e.g. human cells.

Expression vectors and plasmids embodying the present invention comprise one or more constitutive promoters, such as viral promoters or promoters from mammalian genes that are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β-actin promoter.

Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and such like. Promoters that are activated in response to exposure to ionizing radiation, such as fos, jun and erg-1, are also contemplated. The tetVP16 promoter that is responsive to tetracycline is a currently preferred example.

Tissue-specific promoters and/or regulatory elements will be useful in certain embodiments. Examples of such promoters that can be used with the expression vectors of the invention include promoters from the liver fatty acid binding (FAB) protein gene, specific for colon epithelial cells; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The construction and use of expression vectors and plasmids is well known to those of skill in the art. Virtually any mammalian cell expression vector can thus be used in connection with the genes disclosed herein.

Preferred vectors and plasmids are constructed with at least one multiple cloning site. In certain embodiments, the expression vector will comprise a multiple cloning site that is operatively positioned between a promoter and a human Mus81 or murine Mus81 encoding gene sequence. Such vectors can be used, in addition to uses in other embodiments, to create N-terminal or C-terminal fusion proteins by cloning a second protein-encoding DNA segment into the multiple cloning site so that it is contiguous and in-frame with the mammalian Mus81 encoding nucleotide sequence.

In other embodiments, expression vectors comprise a multiple cloning site that is operatively positioned downstream from the expressible human Mus81 or murine Mus81 encoding sequence. These vectors are useful, in addition to their uses, in creating C-terminal fusion proteins by cloning a second protein-encoding DNA segment into the multiple cloning site so that it is contiguous and in-frame with the human Mus81 or murine Mus81 encoding sequence.

Vectors and plasmids in which additional protein- or RNA-encoding nucleic acid segment(s) is(are) also present are, of course, also encompassed by the invention, irrespective of the nature of the nucleic acid segment itself.

A second reporter gene can be included within an expression vector of the present invention. The second reporter gene can be comprised within a second transcriptional unit. Suitable second reporter genes include those that confer resistance to agents such as neomycin, hygromycin, puromycin, zeocin, mycophenolic acid, histidinol and methotrexate.

Expression vectors can also contain other nucleotide sequences, such as IRES elements, polyadenylation signals, splice donor/splice acceptor signals, and the like.

Particular examples of suitable expression vectors are those adapted for expression using a recombinant adenoviral, recombinant adeno-associated viral (AAV) or recombinant retroviral system. Vaccinia virus, herpes simplex virus, cytomegalovirus, and defective hepatitis B viruses, amongst others, can also be used.

In one specific embodiment, the present invention encompasses isolated nucleic acids which encode for novel mammalian checkpoint/repair proteins. In another specific embodiment, the invention encompasses novel mammalian checkpoint/repair proteins derived from nucleic acids isolated from a human source called Hmus81 (human Mus81), and from a murine source called Mmus81 (murine Mus81).

Further provided by the present invention are isolated proteins having an amino acid residue sequence corresponding to that illustrated as SEQ ID NO: 2, 4, 8 or 10, or the amino acid sequence of a functionally equivalent fusion protein product, fragment or bioprecursor of said protein. Also provided by the present invention are isolated proteins having an amino acid sequence corresponding to that illustrated as SEQ ID NO: 12, 14 16 or 18, or the amino acid residue sequence of a functionally equivalent, fusion protein product, biologically active fragment or bioprecursor of said protein. Also envisioned is the use of such protein for the generation of antibodies, monoclonal or polyclonal capable of specifically binding to the amino acid sequences of these proteins or fragments thereof. As is well known to those of skill in the art, the proteins according to the invention can comprise conservative or semi-conservative substitutions, deletions or insertions wherein the protein comprises different amino acids than those disclosed in FIG. 1 and FIG. 2.

A protein of the invention can be in a substantially purified form, in which case it will generally comprise the polypeptide in a preparation in which more than 90%, e.g. 95%, 98%, or 99% of the polypeptide in the preparation is a polypeptide of the invention. Proteins of the invention can be modified, for example by the addition of histidine residues to assist their purification or by the addition of a signal sequence to promote their secretion from a cell. Proteins having at least 90% sequence identity, for example at least 95%, 98% or 99% sequence identity to the polypeptide protein depicted in SEQ ID NO: 2, 4, 8 or 10 may be proteins which are amino acid sequence variants, alleles, derivatives, or mutants of the protein depicted in SEQ ID NO: 2, 4, 8 or 10, and are also provided by the present invention. Similarly, proteins having at least 90% sequence identity, for example at least 95%, 98% or 99% sequence identity to the polypeptide protein depicted in SEQ ID NO: 12, 14, 16 or 18 can be proteins which are amino acid sequence variants, alleles, derivatives, or mutants of the protein depicted in SEQ ID NO: 12, 14, 16 or 18, and are also provided by the present invention.

The percentage identity of protein amino acid residue sequences can be calculated by using commercially available algorithms which compare a reference sequence (i.e. SEQ ID NO: 2, 4, 8, 10, 12, 14, 16, 18) with a query sequence. The following programs (provided by the National Center for Biotechnology Information, NCBI) may be used to determine homologies: BLAST, gapped BLAST, BLASTN and psi-BLAST, which may be used with default parameters. Use of either of the terms "homology" or "homologous" herein does not imply any necessary evolutionary relationship between compared sequences, in keeping with standard use of such terms as "homologous recombination" which merely requires that two nucleotide sequence are sufficiently similar to recombine under the appropriate conditions.

Another method for determining the best overall match between a nucleotide sequence or portion thereof, and a query sequence is the use of the FASTDB computer program based on the algorithm of Brutlag et al., (1990, "Improved sensitivity of biological sequence database searches" *Compt. Appl. Biosci.,* 6:237-245). The program provides a global sequence alignment. The result of such a global sequence alignment is expressed as percent identity. Suitable parameters used in a FASTDB search of a nucleotide sequence to calculate the degree of identity are known.

Where a query sequence is determined to have an identity to that of SEQ ID NO: 2, 4, 8 or 10 of at least 90%, said sequence being that of a protein retaining the same activity as Hmus81, such a sequence is encompassed by the present invention. Similarly, where a query sequence is determined to have an identity to that of SEQ ID NO: 12, 14, 16 or 18 of at least 90%, said sequence being that of a protein retaining the same activity as Mmus81, such a sequence is encompassed by the present invention.

Preferred fragments include those comprising an epitope of the proteins according to the invention. The epitopes can be determined using, for example, peptide scanning techniques as described in the art (see e.g. Geysen et. al., 1986, "A priori determination of a peptide which mimics a discontinuous antigenic determinant" *Mol. Immunol.,* 23; 709-715).

The polyclonal and monoclonal antibodies according to the invention can be produced according to techniques which are known to those skilled in the art (e.g. *Immunochemical Protocols,* 2nd. edition, Pound, J. D. ed., 1998, *Methods in Molecular Biology* Vol. 80, Humana Press, Totowa, N.J.). For example, polyclonal antibodies can be generated by inoculating a host animal, such as a mouse, rabbit, goat, pig, cow, horse, hamster, rat or the like, with a protein or epitope according to the invention and recovering the immune serum. The present invention also includes fragments of whole antibodies which maintain their binding activity, such as for example, Fv, F(ab') and F(ab')$_2$ fragments as well as single chain antibodies.

The nucleic acid and/or the proteins according to the invention can be included in a pharmaceutical composition together with a pharmaceutically acceptable carrier, diluent or excipient therefor. The pharmaceutical composition containing said nucleic acids according to the invention can, for example, be used in gene therapy. Such nucleic acids, according to the invention, can be administered naked, or packaged in protein capsules, lipid capsules, liposomes, membrane based capsules, virus protein, whole virus, cell vectors, bacterial cell hosts, altered mammalian cell hosts, or such suitable means for administration.

There is further provided by the present invention a method for detecting for the presence or absence of a nucleic acid according to the invention, in a biological sample, which method comprises, (a) bringing said sample into contact with a probe comprising a nucleic acid or probe according to the invention under hybridizing conditions, and (b) detecting for the presence of hybridization, for example, by the presence of any duplex or triplex formation between said probe and any nucleic acid present in said sample. Proteins according to the invention can also be detected by (a) contacting said sample with an antibody to an epitope of a protein according to the invention under conditions which allow for the formation of an antibody-antigen complex, (b) monitoring for the presence of any antigen-antibody complex.

Kits for detecting nucleic acids and proteins are also provided by the present invention. A kit for detecting for the presence of a nucleic acid according to the invention in a biological sample can comprise (a) means for contacting the sample with a probe comprising a nucleic acid or a probe according to the invention and means for detecting for the presence of any duplex or triplex formation between said probe and any nucleic acid present in the sample.

Likewise, a kit for detecting for the presence of a protein according to the invention in a biological sample can comprise (a) means for contacting said sample with an antibody to an epitope of a protein according to the invention under conditions which allow for the formation of an antibody-protein complex, and (b) means for monitoring said sample for the presence of any protein-antibody complex.

A further aspect of the present invention provides a method of determining whether a compound is an inhibitor or an activator of expression or activity of the proteins of the mammalian cell cycle checkpoint/repair pathway. The method comprises contacting a cell expressing the proteins in said pathway with said compound and comparing the level of expression of any of the proteins of the checkpoint/repair pathway of said cell against a cell which has not been contacted with said compound. Any compounds identified can then advantageously be used as a medicament or in the preparation of a medicament for treating cancer or proliferative disorders. Alternatively, the compounds can be included in a pharmaceutical composition together with a pharmaceutically acceptable carrier, diluent or excipient therefor. Any compound identified as, or any compound corresponding to a compound identified as an inhibitor of the cell checkpoint/repair pathway can be included in a pharmaceutical composition according to the invention together with a cytotoxic agent, such as a DNA damaging chemotherapeutic agent, and a pharmaceutically acceptable carrier diluent or excipient therefor. Thus, the cell cycle checkpoint/repair inhibitor can enhance the chemotherapeutic effect of cytotoxic agents used in, for example, anti-cancer therapy.

There is also provided by the present invention a method for screening candidate substances for anti-cancer therapy, which method comprises (a) providing a protein according to the present invention exhibiting kinase activity together with a substrate for said protein under conditions such that the kinase will act upon the substrate, (b) bringing the protein and substrate into contact with a candidate substance, (c) measuring the degree of any increase or decrease in the kinase activity of the protein, (d) selecting a candidate substance which provides a decrease or increase in activity. Such a candidate substance can also be used as a medicament, or in the preparation of a medicament for the treatment of cancer or other such proliferative cell disorders.

The present invention thus provides inter alia, for therapeutic compositions comprising (i) Hmus81 protein, fusion protein product, or biologically active fragments thereof, (ii) nucleic acids encoding for Hmus81 protein, fusion protein or fragments thereof, (iii) expression vector constructs having an expressible nucleic acid encoding for Hmus81 protein, fusion protein, or fragments thereof, (iv) anti-sense nucleic acids which correspond to the complement of nucleic acids encoding for Hmus81 protein, (v) modified Hmus81 proteins, (vi) antibodies that specifically bind to a portion of an Hmus81 protein, (vii) transformed host cells capable of expressing Hmus81 protein, fusion protein, or fragments thereof, and (viii) therapeutic agents identified by screening for the ability to bind to and/or affect the activity of Hmus81 protein.

The present invention also provides for therapeutic compositions comprising (i) Mmus81 protein, fusion protein product, or biologically active fragments thereof, (ii) nucleic acids encoding for Mmus81 protein, fusion protein or fragments thereof, (iii) expression vector constructs having an expressible nucleic acid encoding for Mmus81 protein, fusion protein, or fragments thereof, (iv) anti-sense nucleic acids which correspond to the complement of nucleic acids encoding for Mmus81 protein, (v) modified Mmus81 proteins, (vi) antibodies that specifically bind to a portion of an Mmus81 protein, (vii) transformed host cells capable of expressing Mmus81 protein, fusion protein, or fragments thereof, and (viii) therapeutic agents identified by screening for the ability to bind to and/or affect the activity of Mmus81 protein.

Therapeutic compositions of the present invention can combine mixtures of two or more species of Mus81 protein, nucleic acid encoding such protein, antibodies to such protein, or inhibitors of the nucleic acid transcripts of such proteins.

A therapeutic composition of the present invention can be utilized to make a pharmaceutical preparation for the treatment of an individual in need of modulation of the DNA checkpoint/repair mediated by the activity of Hmus81. Another aspect of the present invention is the use of a therapeutic composition of the present invention in the formulation of a pharmaceutical preparation for the treatment of an individual in need of anti-neoplastic treatment. It is further envisioned that a therapeutic composition of the present invention is useful in the formulation of a pharmaceutical preparation in combination with at least one other anti-neoplastic agent for the treatment of an individual in need of anti-neoplastic treatment.

Therapeutic compositions, or pharmaceutical formulations containing such therapeutic compositions, can be used to treat an individual in need of a treatment which involves the Hmus81 mediated activity of targeted cells. Illustrative are treatment for neoplastic conditions, comprising contacting a cell of the individual in need of such treatment with at least one therapeutic composition of the invention. Such therapeutic methods can include the administration of one or more therapeutic composition sequentially, simultaneously, or in combination with other therapeutics for treating a neoplastic condition.

As would be understood by one of skill in the art, many variations and equivalents to the compositions of the present invention are easily obtained and generated through the application of routine methods known in the art using the teaching of the present invention.

Many of the methods and materials for carrying out the basic molecular biology manipulations as described in the examples below are known in the art, and can be found in such references as Sambrook et al., *Molecular Cloning*, 2nd edition, Cold Spring Harbor Laboratory Press (1989); Berger et al., *Guide to Molecular Cloning Techniques, Methods in Enzymology*, Vol. 152, Academic Press, Inc., (1987); Davis et al., *Basic Methods in Molecular Biology*, Elsevier Science Publishing Co., Inc. (1986); Ausubel et al., *Short Protocols in Molecular Biology*, 2nd ed., John Wiley & Sons, (1992); Goeddel *Gene Expression Technology, Methods in Enzymology*, Vol. 185, Academic Press, Inc., (1991); Guthrie et al., Guide to Yeast Genetics and Molecular Biology, Methods in Enzymology, Vol. 194, Academic Press, Inc., (1991); McPherson et al., PCR Volume 1, Oxford University Press, (1991); McPherson et al., PCR Volume 2, Oxford University Press, (1995); Richardson, C. D. ed., *Baculovirus Expression Protocols, Methods in Molecular Biology*, Vol. 39, Humana Press, Inc. (1995).

The invention in its several aspects can be more readily understood with reference to the following examples.

EXAMPLE 1

Human Mus81 (Hmus81) Cloning

Oligonucleotide primers Hmus81FW (GACATGGCG-GCCCCGGTCCG) (SEQ ID NO: 21) and Hmus81REV (GACTCAGGTCAAGGGGCCGTAG) (SEQ ID NO: 22) corresponding to the 5' (ATGGCGGCCCCGGTCCG) (SEQ ID NO: 19) and 3' (CTACGGCCCCTTGACCTGA) (SEQ ID NO: 20) ends of the putative human Mus81 ORF were used to amplify DNA products from a Marathon-Ready human cerebellum cDNA library (Clontech, Palo Alto Calif.) by polymerase chain reaction (PCR). PCR was done with Pfu polymerase and the following reaction conditions: 95° C. for 30", 68° C. for 30", 72° C. for 1-30" (35×). The resulting DNA products were cloned into the pCR2.1-TOPO plasmid as recommended by the manufacturer (Invitrogen, Carlsbad Calif.) and the DNA sequenced.

Oligonucleotide primers corresponding to the 5' and 3' ends of Hmus81, from a putative ORF constructed using the identified yeast sequences were used to amplify sequences from a human cerebellum cDNA library. A 1653 nucleotide sequence was obtained which encodes a 551 amino acid protein (SEQ ID NO: 2) with significant similarity to the yeast Mus81 sequences (SEQ ID NO: 5). A longer 1857 nucleotide sequence encodes for a shorter variant of Hmus81 that is a 455 amino acid protein (SEQ ID NO: 4). This results from the presence of a stop codon within a DNA insert from position 1274 to 1474 of the nucleotide sequence (SEQ ID NO: 25).

EXAMPLE 2

Mouse Mus81 Cloning

Oligonucleotide primers RJH030 (GAGACTCTGAAG-GAGCCAG) (SEQ ID NO: 23) and RJH031 (GCTAAAAG-GCTAGCCAGCC) (SEQ ID NO: 24) corresponding to sequences flanking the 5' and 3' ends of the putative mouse Mus81 ORF were used to amplify DNA products from a Marathon-Ready mouse brain cDNA library (Clontech) by PCR. The following conditions were used: 95° C. for 60", 60° C. for 60", 72° C. for 2'30" (35×). The resulting PCR products were cloned into the pCR2.1-TOPO plasmid (Invitrogen) and the DNA sequenced.

The human cDNA sequences were used to search for homologous mouse sequences in the public databases. Several ESTs with significant homology to the 5' and 3' ends of the human sequence were identified. This resulted in the amplification of several sequences (probably representing splicing variants) encoding proteins from 424 to 551 amino acids (FIG. 2).

The translation products of the human and mouse cDNAs have significant similarity to the yeast Mus81 amino acid sequences. The longest human (Hmus81$_4$) and mouse (Mmus81$_1$) translation products are 17-20% identical and 30-40% similar to the yeast proteins. No other mammalian proteins had high similarity with the yeast proteins indicating that this had identified the closest homologues. The mouse sequence is 81% identical and 87% similar to the human protein. Alignment of the mammalian and yeast proteins demonstrates that there is similarity throughout, with more highly conserved regions in the central and C-terminal regions of the proteins (FIG. 3). The conserved central region is found in the XPF family of endonucleases and corresponds to the catalytic site (Aravind et al., "Conserved domains in DNA repair protein and evolution of repair systems" *Nucleic Acids Res* 27(5): 1223-1242, 1999).

EXAMPLE 3

Northern Blot Hybridisation

Human multiple tissue and cancer cell line blots (Clontech) were hybridized with a 1.7 kb probe corresponding to human Mus81 cDNA using the QuickHyb method as described by the manufacturer (Clontech). The blots were washed at high stringency (0.1×SSC, 0.1% SDS, 50° C., 2×20 min) and signals were detected by autoradiography.

Figure 6:
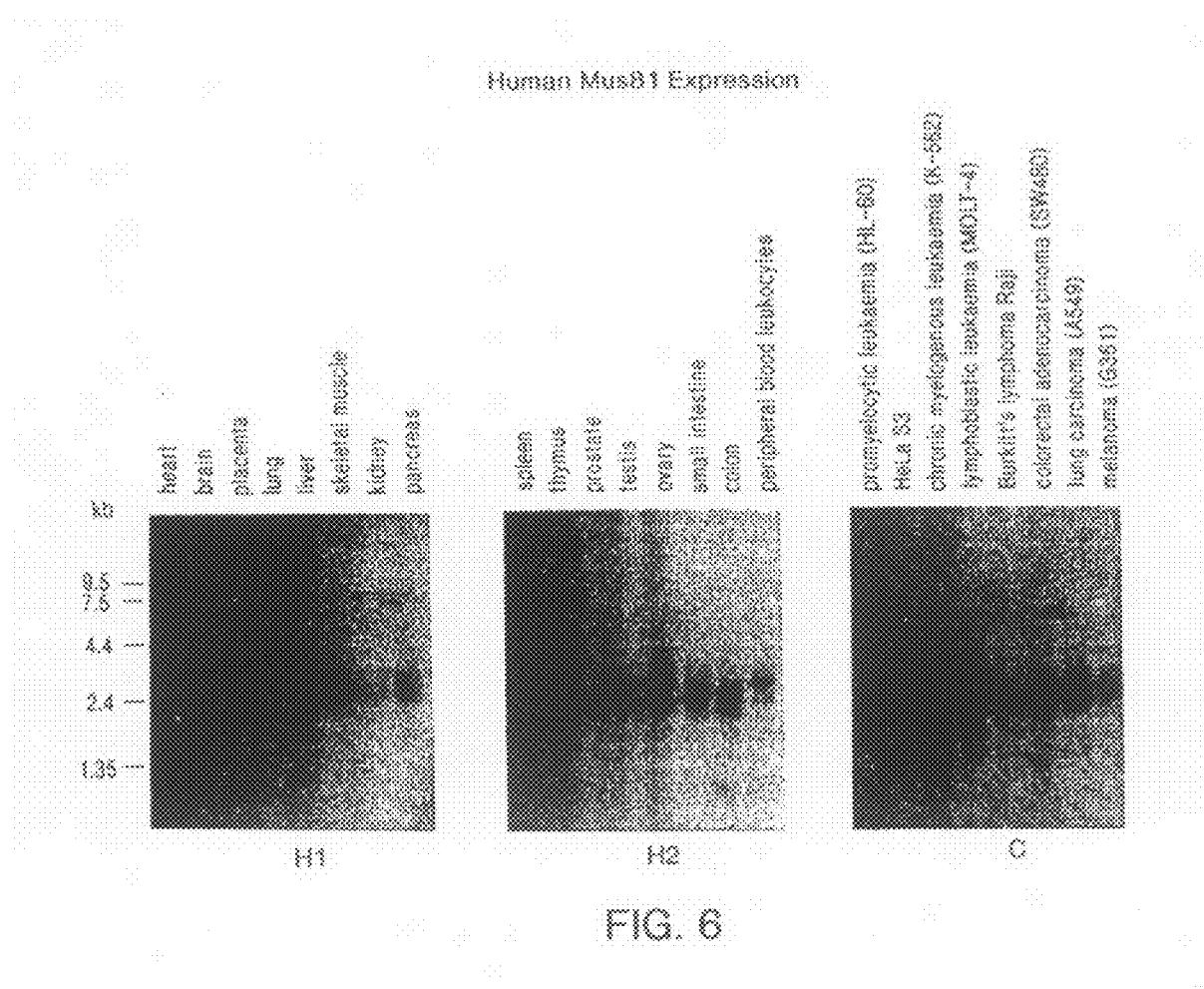
FIG. 6. Northern blot analysis of human Mus81. Human tissues (H1 and H2) and cancer cell lines (C).

Northern blot analysis using the Hmus81 cDNA as probe demonstrated that specific transcripts of approximately 2.5-3.0 kb were present in most human tissues with lower levels in lung, liver and kidney (FIG. 6).

EXAMPLE 4

Identification of a Cds1 FHA Domain-binding Protein

A yeast two-hybrid screen was employed using the *S. pombe* Cds1 FHA domain as bait and a *S. pombe* cDNA library as prey. Transformants that grew in the selection conditions for interaction between the bait and prey proteins were isolated and tested in secondary screens for specificity of interaction. One of the transformants that was isolated from this screen contained a cDNA sequence that encoded a 572 amino acid hypothetical protein (PID g2213548). The amino acid sequences encoded by the *S. pombe* ORF SPCC4G3.05c (Spmus81) (SEQ ID NO:6) and *S. cerevisiae* ORF YDR386W (ScMus81) (SEQ ID NO:5) were compared and alignment of the translation products of the yeast and human sequences for amino acid sequence comparison was performed with the program CLUSTALW.

The translation product of this *S. pombe* ORF (mus81$^+$) was found to have significant homology to the *S. cerevisiae* hypothetical protein encoded by ORF YDR386w (25% identity, 42% similarity). This protein has been annotated as Mus81 in the *Saccharomyces* Genome Database and is reported to be in a complex with the DNA repair protein Rad54. A null mutant is reported to be viable, but defective in meiosis and sensitive to the DNA damaging agents MMS and UV light. The genomic copy of *S. pombe* mus81$^+$ was tagged at the 3' end with three tandem copies of the haemoinfluenza HA epitope through site-directed recombination.

Antibodies directed against the HA epitope detected polypeptides from an asynchronous culture which migrated through SDS-PAGE with a mobility of approximately 65-70 kDa. The calculated predicted molecular weight being about 65 kDa.

The presence of multiple polypeptides demonstrates that the protein can be post-translationally modified, possibly by phosphorylation. The proportion of slower migrating polypeptides in asynchronous cultures was increased by treatment of the cells with hydroxyurea, a ribonucleotide reductase inhibitor that causes a cell cycle arrest in S-phase.

This shows that the post-translational modification is cell cycle regulated, and may be checkpoint dependent. The increased modification of Mus81 was not observed in Cds1 and Rad3 checkpoint mutant strains, but did occur in a rad54 mutant strain. The physical interaction between Cds1 and Mus81 was confirmed in vivo by co-immunoprecipitation of the two proteins.

Inactivation of Mus81 makes fission yeast more sensitive to UV irradiation. This is also observed in yeast strains that are defective for the two repair pathways that account for all detectable repair of UV induced damage (nucleotide excision repair and UV excision repair). This suggests that Mus81 is required for tolerating UV damage.

In order to determine whether the product encoded by this gene is involved in checkpoint/repair responses, a S. pombe strain was generated in which the entire ORF for mus81 was deleted by site-directed recombination. This mutant strain had increased sensitivity to UV irradiation, but appeared to have an intact checkpoint/repair response in the presence of DNA damage.

EXAMPLE 5

Interaction between Human Mus81 and Cds1

The $Hmus81_1$ ORF was cloned into the mammalian transient expression vector pYC1HA (Fu et al., "TNIK, a novel member of the germinal center kinase family that activates the c-Jun N-terminal kinase pathway and regulates the cytoskeleton" *J. Biol. Chem.* 274(43):30729-30737, 1999) immediately downstream of and in frame with the HA epitope tag. Similarly, the human Cds1 ORF was cloned into the pYC1FLAG (Fu et al., supra 1999) expression vector downstream of and in frame with the FLAG epitope. Plasmid DNA was used to transfect HEK293 cells using Superfect reagent as described by the manufacturer (Qiagen). After 24 hours, the cells were collected in lysis buffer (1% NP40, 50 mM Tris HCl pH 7.5, 150 mM NaCl, 1 mM DTT) supplemented with Pefabloc®SC and Complete™ protease inhibitors as recommended by the manufacturer (Boehringer Mannheim). The lysates were cleared of debris by centrifugation at 10000 g for 15 min. (4° C.).

Cleared supernatants from cells transiently expressing epitope-tagged proteins were incubated several hours at 4° C. with agarose bead-linked antibodies directed against the HA (Santa Cruz Biotechnologies) or FLAG (OctA-probe™, Santa Cruz Biotechnologies) epitope. The agarose beads were then washed 3 times with lysis buffer, resuspended in SDS denaturing buffer and incubated at 95° C. for 5 min. Supernatants and immunoprecipitates were resolved by SDS-PAGE and transferred to PVDF membranes. The membranes were blocked with TTBS (150 mM NaCl, 100 mM Tris-HCl pH7.5, 0.1% Tween 20) containing 5% skimmed milk. For detection of HA-tagged Mus81 protein, the blots were incubated for two hours at room temperature with horseradish peroxidase conjugated anti-HA antibodies (Santa Cruz Biotechnologies) diluted to 1:1000 in TTBS containing 0.1% milk. For detection of FLAG-tagged Cds1, blots were incubated with anti-FLAG® M2 antibody (Sigma) diluted to 1:3000 in TTBS. The blot washed with TTBS and then incubated for 1 hour at room temperature with horseradish peroxidase conjugated anti-mouse Ig antibody diluted to 1:3000 in TTBS. Finally, the blots were washed with TTBS and signals detected using the ECL-Plus chemoluminescence detection system as described by the manufacturer (Amersham Pharmacia Biotech).

Figure 8:
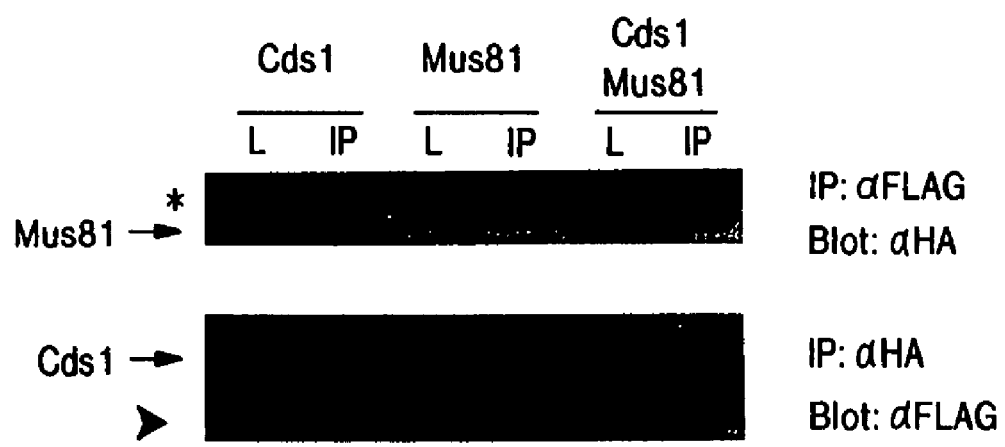
FIG. 8. Co-immunoprecipitation of human Mus81 and Cds1. Western blots of lysates (L) and immunoprecipitates (IP) from cells expressing tagged forms of Mus81 and Cds1 separately and together. Bands corresponding to Mus81 and Cds1 are indicated with arrows. Bands corresponding to a protein that cross-reacts with the HA antibody in the upper panel indicated by an asterisk. Immunoglobulin heavy chains in the lower panel are indicated by an arrowhead.

In order to determine whether human Mus81 and Cds1 are capable of interacting, the proteins were tagged with the HA and FLAG epitopes, respectively, and expressed transiently in mammalian cells alone or in combination. Cell lysates were prepared from the transfected cells and immunoprecipitations were carried out with antibodies against the epitope tags. The resulting immunoprecipitates were subjected to western blot analysis with the reciprocal antibody. The HA antibodies recognized a 65 kDa protein, the expected size for the tagged version of human Mus81, only in lysates from cells transfected with the Mus81 construct. Similarly, the FLAG antibodies recognized a 65 kDa protein corresponding to tagged Cds1 only in lysates from cells expressing Cds1-FLAG (FIG. 8). Mus81 was also detected in precipitates obtained with the FLAG antibody from lysates of cells transfected with both Cds1 and Mus81. However, Mus81 was not present in precipitates from cells expressing only Mus81 or Cds1. Conversely, Cds1 was only detected in precipitates obtained with the HA antibody from cells expressing both tagged proteins. These results indicate that the human Mus81 and Cds1 proteins are capable of interacting in mammalian cells. This suggests that the Hmus81 protein is involved in UV DNA damage repair.

The present invention identifies the human and mouse homologues of the yeast Mus81 protein, which are involved in UV damage tolerance and interacts with the FHA domain of fission yeast Cds1. Human Mus81 is present as various splicing isoforms and is expressed in most human tissues and cancer cell lines. Analysis of a Mus81-GFP fusion protein suggests that it is predominantly nuclear while co-immunoprecipitation of tagged forms of human Mus81 and Cds1 indicate that they form a complex in mammalian cells.

EXAMPLE 6

Genomic Structure and Chromosomal Localization of Human Mus81

The human cDNAs were used to identify contiguous genomic sequences containing Mus81 in the public databases. Comparison of the genomic sequence confirmed that the various cDNA forms corresponded to different splice variants. Examination of the results identified 18 exons encoding Mus81 sequences within a 5.8 kb genomic region (FIG. 4). The splicing differences in the cDNAs identified occurred in the region encompassing exons 13 and 14. The nucleic acid encoding for human $Mus81_2$ (SEQ ID NO:3) was composed of all of the exons identified. The nucleic acid encoding for human $Mus81_1$ (SEQ ID NO: 1) did not contain exon 13 and the nucleic acid encoding for human $Mus81_3$ (SEQ ID NO: 7) was lacking exons 13 and 14. Splicing of the nucleic acid encoding for human $Mus81_4$ (SEQ ID NO: 9) was identical to that found in the nucleic acid encoding for human $Mus81_1$ (SEQ ID NO: 1) except that it contained three additional nucleotides (CAG) at the 5'end of exon 14 due to utilization of an alternative splice acceptor site. Splicing of all introns utilized the consensus donor and acceptor sites.

Fluorescence in situ Hybridisation (FISH) analysis was carried out using standard procedures. Briefly, human lymphocytes isolated from blood were synchronized by culturing in the presence of 0.18 mg/ml BrdU. The BrdU washed off to release the block and the cells were cultured for 6 hours prior to harvesting and fixation. FISH detection was carried out with a Mus81 cDNA probe labelled with biotinylated dATP. Chromosomal localization was determined by comparison of FISH signals to DAPI banding pattern.

Figure 5A:
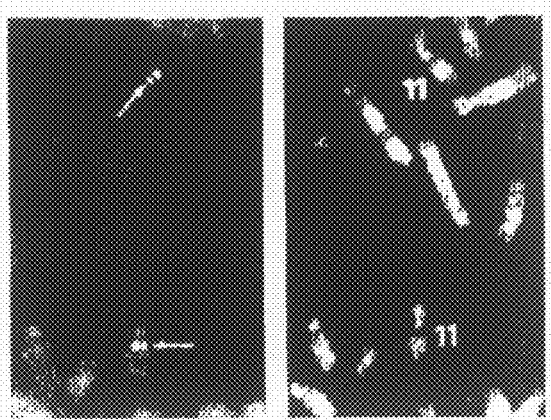
FIG. 5. Chromosomal localization of human Mus81 by FISH analysis. (A) Chromosome metaphase spread labelled with a fluorescent Mus81 cDNA probe (left panel) and corresponding DAPI staining (right panel). (B) Idiogram of chromosome 11 with location of Hybridisation signal from 10 representative metaphase spreads.
Figure 5B:
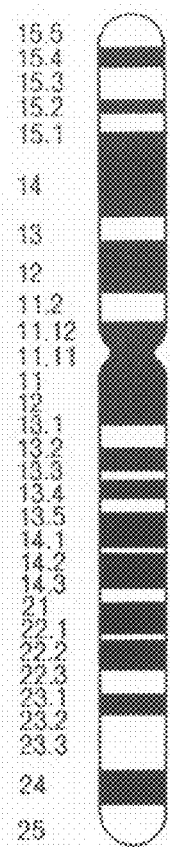

FISH analysis using human Mus81 cDNA as a probe resulted in staining of a single pair of chromosomes at 11q13 in 70 out of 100 mitotic spreads (FIG. 5). This localization was confirmed by the previous assignment of a public EST (WI-18484), which is identical to part of the Mus81 sequence, to chromosome 11 on the WICGR radiation hybrid map.

EXAMPLE 7

Expression and Intracellular Localization of Human Mus81

The human Mus81₄ cDNA was cloned downstream and in frame with the green fluorescent protein (GFP) encoding open reading frame gene (ORF) in a retrovirus expression vector. The retrovirus expression vector is chosen to allow for the regulated expression of proteins of interest, and in a preferred embodiment allows fusion of the protein of interest to the GFP or modified GFP for visualization of expression. It is also possible to express both the Mus81 protein and GFP protein as separate proteins from the same expression vector.

Commercially available vectors suitable for expression of Mus81 protein include and are not limited to, for example, pRevTRE (Clontech) which are derived from the pLNCX (Clontech) retroviral expression vector (Gossen, M. & Bujard, H., 1992, "Tight control of gene expression in mammalian cells by tetracycline-responsive promoters" *PNAS (USA)* 89:5547-5551), or GFP fusion protein expressing retroviral expression vectors pLEGFP-N1 and pLEGFP-C1 (Clontech).

The Human Mus81-GFP expressing retrovirus vector was used to infect A549 lung carcinoma cells containing an integrated copy of the tTA transactivator for regulated expression of the fusion protein. The cells were grown to allow expression of the fusion protein, and visualized by fluorescence microscopy three days after infection.

Figure 7:
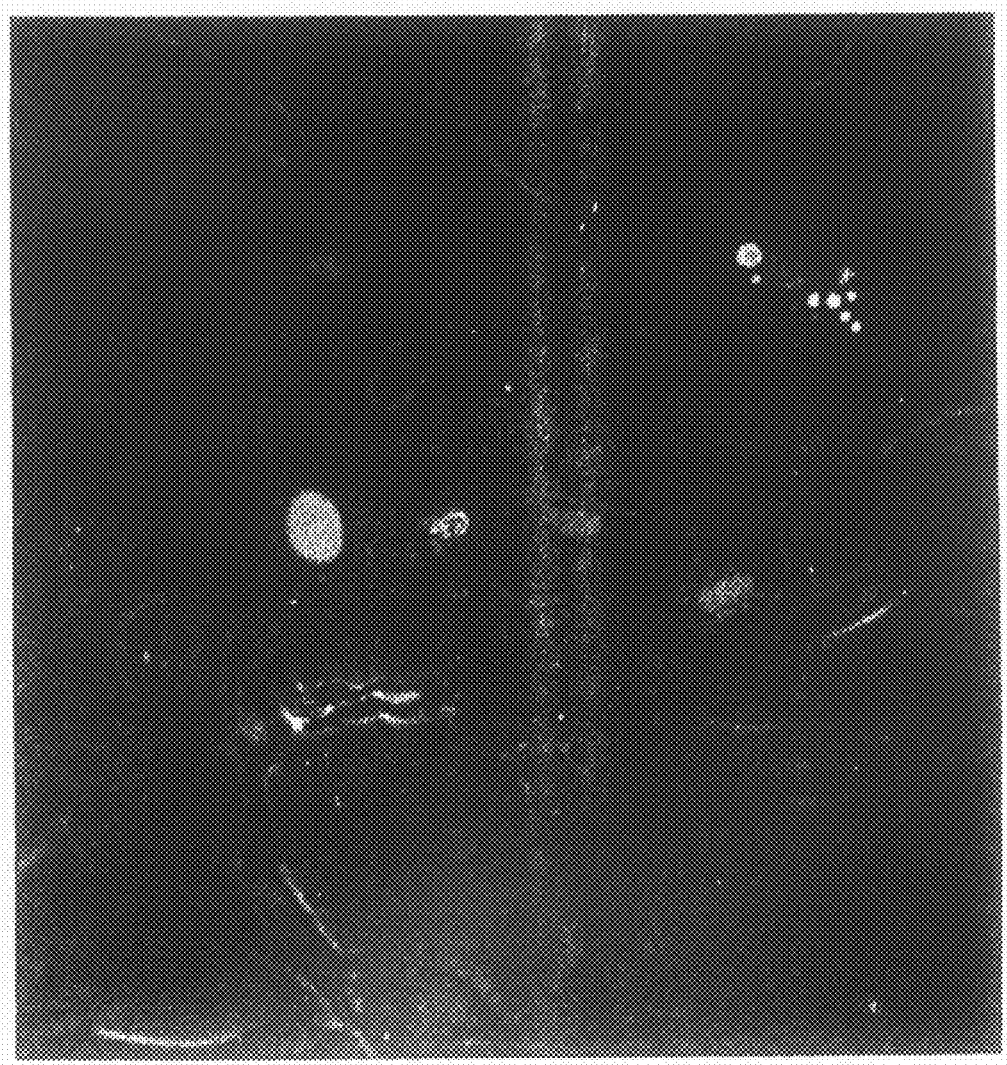
FIG. 7. Cellular localization of a Mus81-GFP (GFP: Green Fluorescent Protein e.g. from *Aequorea victoria*) fusion protein. A549 cells infected with a retrovirus expressing a Hmus81-GFP fusion at 3 days after induction.

Human Mus81 was expressed as a fusion with the GFP protein in A549 cells. Fluorescence was detected primarily in the nuclei of these cells (FIG. 7). The nuclear localization of Hmus81 is in agreement with its role in DNA repair associated functions.

The invention, having been fully described in many of its aspects and claimed herein can be made and executed without undue experimentation by one of skill in the art according to the teaching herein. While the compositions and methods of this invention have been described by way of example above, it will be apparent to those of skill in the art that many variations and modifications can be applied to the compositions and methods described herein without departing from the concept, spirit and scope of the invention.

---

We claim:

1. An isolated human Mus81 protein, said protein comprising the amino acid sequence selected from the group of SEQ ID NO: 2, SEQ ID NO: 4, SEQ ID NO: 8, and SEQ ID NO: 10.

2. A fusion protein comprising the human Mus81 protein of claim 1.

3. The fusion protein of claim 2 comprising said human Mus81 protein and GFP.

4. An isolated murine Mus81 protein, said protein comprising the amino acid sequence selected from the group of SEQ ID NO: 12, SEQ ID NO: 14, SEQ ID NO: 16, and SEQ ID NO: 18.

5. A fusion protein comprising the murine Mus81 protein of claim 4.

6. The fusion protein of claim 5 comprising said murine Mus81 protein and GFP.

* * * * *